United States Patent
Labadie et al.

(10) Patent No.: US 10,053,451 B2
(45) Date of Patent: Aug. 21, 2018

(54) HETEROCYCLIC ESTROGEN RECEPTOR MODULATORS AND USES THEREOF

(71) Applicant: Genentech, Inc., South San Francisco, CA (US)

(72) Inventors: Sharada Labadie, Sunnyvale, CA (US); Jun Liang, Palo Alto, CA (US); Daniel Fred Ortwine, San Ramon, CA (US); Xiaojing Wang, Foster City, CA (US); Birong Zhang, Union City, CA (US); Nicholas D. Smith, San Diego, CA (US); Steven P. Govek, San Diego, CA (US); Mehmet Kahraman, La Jolla, CA (US); Andiliy G. Lai, San Diego, CA (US); Johnny Y. Nagasawa, San Diego, CA (US); Simon Charles Goodacre, Harlow (GB); Nicholas Charles Ray, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/164,102

(22) Filed: May 25, 2016

(65) Prior Publication Data

US 2016/0347742 A1   Dec. 1, 2016

Related U.S. Application Data

(60) Provisional application No. 62/166,360, filed on May 26, 2015.

(51) Int. Cl.
| | | |
|---|---|---|
| *C07D 405/14* | (2006.01) | |
| *A61K 31/497* | (2006.01) | |
| *A61K 31/397* | (2006.01) | |
| *C07D 491/052* | (2006.01) | |
| *A61K 31/4162* | (2006.01) | |
| *C07D 405/12* | (2006.01) | |
| *A61K 31/4439* | (2006.01) | |
| *A61K 31/416* | (2006.01) | |
| *C07D 405/04* | (2006.01) | |

(52) U.S. Cl.
CPC .......... *C07D 405/14* (2013.01); *A61K 31/397* (2013.01); *A61K 31/416* (2013.01); *A61K 31/4162* (2013.01); *A61K 31/4439* (2013.01); *A61K 31/497* (2013.01); *C07D 405/04* (2013.01); *C07D 405/12* (2013.01); *C07D 491/052* (2013.01)

(58) Field of Classification Search
CPC .................................................. C07D 405/14
USPC .................................................. 514/210.19
See application file for complete search history.

(56) References Cited

U.S. PATENT DOCUMENTS

| | | |
|---|---|---|
| 5,407,947 A | 4/1995 | Bryant |
| 6,060,503 A | 5/2000 | Labrie |
| 6,262,270 B1 | 7/2001 | Draper |
| 7,399,767 B2 | 7/2008 | Zhang et al. |
| 8,299,112 B2 | 10/2012 | Smith et al. |
| 8,455,534 B2 | 6/2013 | Smith et al. |
| 8,703,810 B2 | 4/2014 | Kahraman et al. |
| 9,078,871 B2 | 7/2015 | Kahraman et al. |
| 9,187,460 B2 | 11/2015 | Smith et al. |
| 9,193,714 B2 | 11/2015 | Smith |
| 2003/0207380 A1 | 6/2003 | Saito et al. |
| 2004/0034017 A1 | 2/2004 | Kuenzer |
| 2004/0259915 A1 | 12/2004 | Kanojia |
| 2008/0221125 A1* | 9/2008 | Zhang ................. C07D 405/04 514/255.05 |
| 2012/0071535 A1 | 3/2012 | Smith et al. |
| 2013/0116232 A1 | 5/2013 | Kahraman |
| 2013/0231333 A1 | 9/2013 | Smith et al. |
| 2015/0105403 A1 | 4/2015 | Smith et al. |
| 2015/0258080 A1 | 9/2015 | Hager |
| 2015/0258099 A1 | 9/2015 | Hager |
| 2016/0175284 A1 | 6/2016 | Labadie |

FOREIGN PATENT DOCUMENTS

| | | | |
|---|---|---|---|
| WO | 2004/091488 A2 | 10/2004 | |
| WO | 2015/082990 A1 | 6/2011 | |
| WO | 2011/156518 A2 | 12/2011 | |
| WO | WO2011156518 A2 * | 12/2011 | ........... A61K 31/453 |
| WO | 2012/037410 A2 | 3/2012 | |
| WO | 2012/037411 A2 | 3/2012 | |
| WO | 2013/056178 A3 | 4/2013 | |
| WO | 2013/090829 A1 | 6/2013 | |
| WO | 2013/090836 A1 | 6/2013 | |
| WO | WO-2013090836 A1 * | 6/2013 | ........... C07D 311/58 |

(Continued)

OTHER PUBLICATIONS

Govek et al., "Optimization of an indazole series of selective estrogen receptor degraders: Tumor regression in a tamoxifen-resistant breast cancer xenograft" Bioorg Med Chem Lett. 25(22):5163-7 ( 2015).

(Continued)

*Primary Examiner* — Yong Chu

(74) *Attorney, Agent, or Firm* — Kevin M. Clark

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

10 Claims, No Drawings

(56) References Cited

FOREIGN PATENT DOCUMENTS

| WO | 2013/142266 A1 | 9/2013 |
| WO | 2014/151899 A1 | 9/2014 |
| WO | 2014/205136 A1 | 12/2014 |
| WO | 2015/136016 A2 | 9/2015 |
| WO | 2015/136017 A1 | 9/2015 |
| WO | 2016/097071 A1 | 6/2016 |
| WO | 2016/097073 A1 | 6/2016 |

OTHER PUBLICATIONS

ISR for PCT/EP2016/061733 (2016).

Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 (2015).

Nareshkumar Jain et al., "Identification and Structure-Activity Relationships of Chromene-Derived Selective Estrogen Receptor Modulators for Treatment of Postmenopausal Symptoms" Journal of Medicinal Chemistry 52(23):7544-7569 (Apr. 14, 2009).

* cited by examiner

HETEROCYCLIC ESTROGEN RECEPTOR MODULATORS AND USES THEREOF

CROSS REFERENCE TO RELATED APPLICATIONS

This non-provisional application filed under 37 CFR § 1.53(b), claims the benefit under 35 USC § 119(e) of U.S. Provisional Application Ser. No. 62/166,360 filed on 26 May 2015, which is incorporated by reference in entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions.

There is a need for new ER-α targeting agents that have activity in the setting of metastatic disease and acquired resistance (Jordan, V. (2003) J. Med. Chem. 46:883-908; Jordan, V. (2003) J. Med. Chem. 46:1081-1111; Riggs B. (2003) New Eng. J. Med. 348:618-629). Chromene-type selective estrogen receptor modulators have been described (Jain et al (2009) J. Med. Chem. 52:7544-7569; WO 2011/156518, U.S. Pat. No. 8,703,810; WO 2013/090829; WO 2013/090836; WO 2014/025138; WO 2014/205136; US 2006/0020018; U.S. Pat. No. 7,399,767; WO 2006/078834; WO 2006/042409; WO 2001/054699; WO 2001/026651; WO 2001/001969; WO 1999/063974; WO 1996/026201; U.S. Pat. No. 6,060,503).

SUMMARY OF THE INVENTION

In one aspect, presented herein are compounds of Formulas (I)-(X), or a pharmaceutically acceptable salt, solvate, or prodrug thereof, that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, compounds of Formulas (I)-(X), or a pharmaceutically acceptable salt, solvate, or prodrug thereof, are useful for the treatment of ER-related diseases or conditions including, but not limited to, ER-α dysfunction associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis), uterine diseases (e.g., leiomyoma, uterine leiomyoma, endometrial hyperplasia, endometriosis), and reproductive defects (age of menarche, endometriosis, infertility).

In one aspect, described herein are compounds of Formulas (I)-(X), pharmaceutically acceptable salts, solvates, metabolites and prodrugs thereof. Compounds of Formulas (I)-(X) are estrogen receptor modulators, estrogen receptor antagonists, or estrogen receptor degraders. In some embodiments, the compound of Formulas (I)-(X) is an estrogen receptor antagonist as well as an estrogen receptor degrader or displays minimal or no estrogen receptor agonist activity. In some embodiments, in the context of treating cancers, the compound of Formulas (I)-(X) may offer improved therapeutic activity characterized by complete or longer-lasting tumor regression, a lower incidence or rate of development of resistance to treatment, and/or a reduction in tumor invasiveness.

Throughout the specification, groups and substituents thereof can be chosen by one skilled in the field to provide stable moieties and compounds.

An aspect of the invention is a pharmaceutical composition comprising a therapeutically effective amount of a compound of Formulas (I)-(X), or a pharmaceutically acceptable salt, or solvate thereof.

An aspect of the invention is a method of treating an estrogen receptor dependent or estrogen receptor mediated disease or condition in mammal comprising administering to the mammal a therapeutically effective amount of a compound of Formulas (I)-(X), or a pharmaceutically acceptable salt, or solvate thereof, wherein estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects. The estrogen receptor dependent or estrogen receptor mediated disease or condition is selected from bone cancer, breast cancer, lung cancer, colorectal cancer, endometrial cancer, prostate cancer, ovarian cancer, and uterine cancer.

An aspect of the invention is a method of treating hormone receptor positive metastatic breast cancer in a postmenopausal woman with disease progression following antiestrogen therapy comprising administering to the woman an estrogen receptor degrading compound of Formulas (I)-(X), or a pharmaceutically acceptable salt, or solvate thereof.

An aspect of the invention is a method of treating a hormonal dependent benign or malignant disease of the breast or reproductive tract in a mammal comprising administering to the mammal an effective amount of a compound of Formulas (I)-(X), or a pharmaceutically acceptable salt, or solvate thereof.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group is saturated. The alkyl moiety may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, and the like.

The term "alkylene" refers to a divalent alkyl radical. Any of the above mentioned monovalent alkyl groups may be an alkylene by abstraction of a second hydrogen atom from the alkyl. Typical alkylene groups include, but are not limited to, —$CH_2$—, —$CH(CH_3)$—, —$C(CH_3)_2$—, —$CH_2CH_2$—, and the like.

An "alkenyl" group refers to a branched or straight chain alkyl group as defined above, except that at least one double bond exists between two carbon atoms.

An "alkynyl" group refers to a branched or straight chain alkyl group as defined above, except that at least one triple bond exists between two carbon atoms.

An "alkoxy" group refers to a (alkyl)O— group, where alkyl is as defined herein.

The term "alkylamine" refers to the —$N(alkyl)_xH_y$ group, where x and y are selected from the group x=1, y=1 and x=2, y=0.

The term "aromatic" refers to a planar ring having a delocalized π-electron system containing 4n+2π electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1, 1-diyl, cyclobutan-1, 1-diyl, cyclopentan-1, 1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro (F), chloro (Cl), bromo (Br) or iodo (I).

The term "fluoroalkyl" refers to an alkyl in which one or more hydrogen atoms are replaced by a fluorine atom. In one aspect, a fluoroalkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached (or C-linked) or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

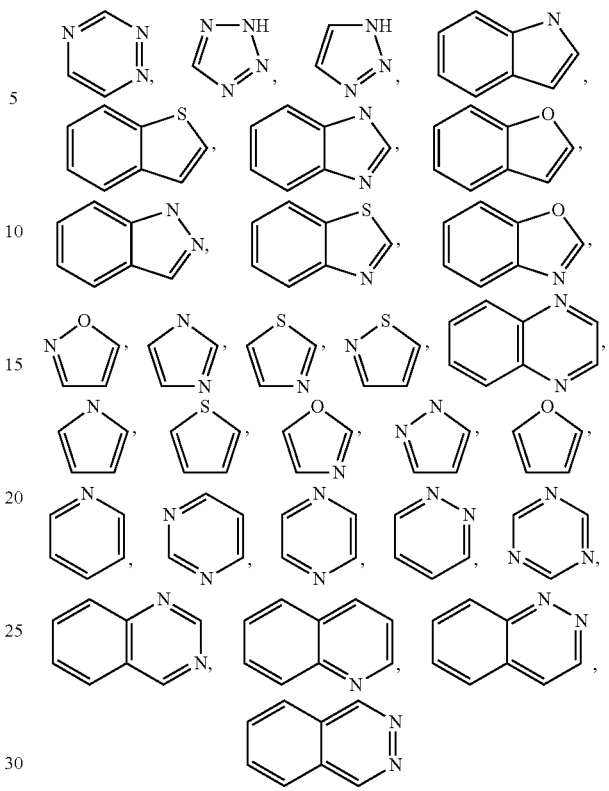

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group can be a monoradical or a diradical (i.e., a heteroarylene group).

A "heterocycloalkyl" or "heteroalicyclic" group refers to a cycloalkyl group that includes at least one heteroatom selected from nitrogen, oxygen and sulfur. The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formulas (I)-(X), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%. In some embodiments, a degrader as described herein lowers steady state estrogen receptor levels by at least 95%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that might occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formulas (I)-(X), or a pharmaceutically acceptable salt thereof, and a co-agent, are both administered to a patient simultaneously in the form of a single entity or dosage. The term "non-fixed combination" means that the active ingredients, e.g. a compound of Formulas (I)-(X), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Estrogen Receptor

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that are estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women, which have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Given the central role of ER-α in breast cancer development and progression, compounds disclosed herein are useful in the treatment of breast cancer, either alone or in combination with other agent agents that can modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used in the treatment of an estrogen receptor dependent or estrogen receptor mediated disease or condition in mammal.

In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects.

In some embodiments, the estrogen receptor dependent or estrogen receptor mediated disease or condition is selected from bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, maj or depressive disorder, psychosis, age of menarche, endometriosis, and infertility.

In some embodiments, compounds disclosed herein are used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naïve.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal. In some embodiments, compounds disclosed herein are used in the treatment of uterine fibroids in a mammal.

Heterocyclic Estrogen Receptor Compounds

In one aspect, provided herein is a compound of Formula (I), or a pharmaceutically acceptable salt, solvate, metabolite or prodrug thereof:

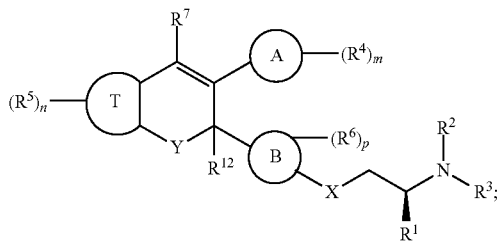

Formula (I)

wherein:

Y is —O—, —S—, or —NR$^{13}$—; R$^{13}$ is H, —C(=O)R$^{10}$, substituted or unsubstituted C$_1$-C$_6$alkyl, substituted or unsubstituted C$_1$-C$_6$fluoroalkyl, or substituted or unsubstituted C$_1$-C$_6$heteroalkyl;

X is —O—, —S—, —CH$_2$—, —NH— or —N(C$_1$-C$_6$alkyl)-;

ring A is phenyl, naphthyl, monocyclic heteroaryl or bicyclic heteroaryl;

ring B is phenyl or a monocyclic heteroaryl;

ring T is a fused phenyl, a fused monocyclic heteroaryl, or a fused bicyclic heteroaryl;

wherein at least one of ring A, ring B or ring T is heteroaryl;

R$^1$ is H, F, C$_1$-C$_4$alkyl, or C$_1$-C$_4$fluoroalkyl;

R$^2$ is selected from H and R$^{10}$;

R$^3$ is selected from —C(=O)R$^{10}$, —C(=O)OR$^{10}$, —C(=O)NHR$^{10}$, —S(=O)$_2$R$^{10}$, and R$^{10}$;

or

R$^2$ and R$^3$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;

each R$^4$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

each R$^5$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

each R$^6$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

R$^7$ is H, halogen, CN, substituted or unsubstituted C$_1$-C$_6$alkyl, or substituted or unsubstituted C$_1$-C$_6$fluoroalkyl;

each R$^9$ is independently selected from H, —C(=O)R$^{10}$, —C(=O)OR$^{10}$, —C(=O)NHR$^{10}$, substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl); or each R$^{10}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl);

R$^{12}$ is H, or C$_1$-C$_4$alkyl;

m is 0, 1, 2, 3, 4 or 5;

n is 0, 1, 2, 3 or 4; and p is 0, 1, 2, 3 or 4.

Exemplary embodiments of Formula I compounds include wherein ring T is a fused pyrrolyl, fused imidazolyl, fused pyrazolyl, fused triazolyl, fused oxazolyl, fused thiazolyl, fused thiophenyl, or fused furanyl.

Exemplary embodiments of Formula I compounds include wherein the compound has the structure of Formula (II):

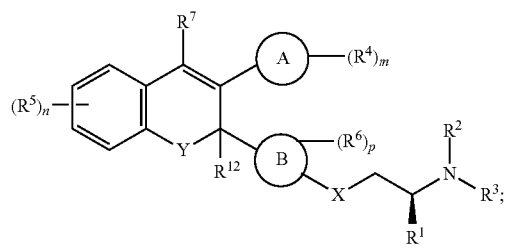

Formula (II)

wherein:

ring A is phenyl, naphthyl, monocyclic heteroaryl or bicyclic heteroaryl;

ring B is phenyl or a monocyclic heteroaryl;

wherein at least one of ring A, or ring B is heteroaryl.

Exemplary embodiments of Formula I compounds include wherein the compound has the structure of Formula (III):

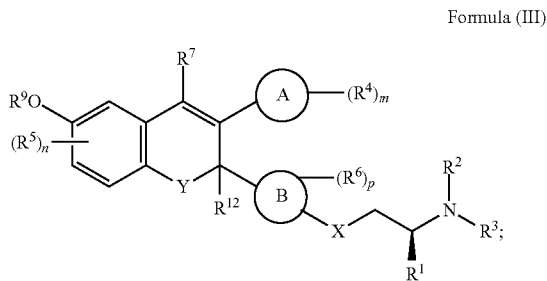

Formula (III)

wherein:
ring A is phenyl, naphthyl, monocyclic heteroaryl or bicyclic heteroaryl;
ring B is phenyl or a monocyclic heteroaryl;
wherein at least one of ring A, or ring B is heteroaryl; and n is 0, 1, 2, or 3.

Exemplary embodiments of Formula I compounds include wherein the compound has the structure of Formula (IV):

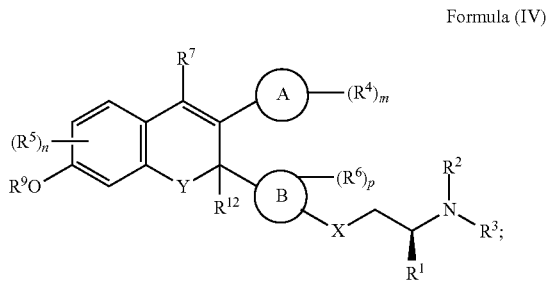

Formula (IV)

wherein:
ring A is phenyl, naphthyl, monocyclic heteroaryl or bicyclic heteroaryl; and
ring B is phenyl or a monocyclic heteroaryl;
wherein at least one of ring A, or ring B is heteroaryl; and n is 0, 1, 2, 3 or 4.

Exemplary embodiments of Formula I compounds include wherein the compound has the structure of Formula (V):

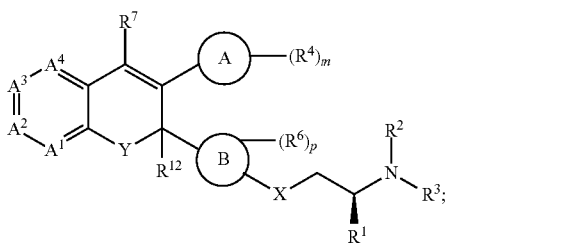

Formula (V)

wherein:
each of $A^1$, $A^2$, $A^3$, $A^4$ is independently CH, $CR^5$ or N;
each $R^5$ is independently selected from H, halogen, —CN, —OH, —$OR^9$, —$SR^9$, —S(=O)$R^{10}$, —S(=O)$_2R^{10}$, —NHS(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl; or two $R^5$ on adjacent carbon atoms are taken together with the carbon atoms to which they are attached to form a substituted or unsubstituted 5 or 6 membered heteroaryl;

ring A is phenyl, naphthyl, monocyclic heteroaryl or bicyclic heteroaryl; and ring B is phenyl or a monocyclic heteroaryl.

Exemplary embodiments of Formula V compounds include wherein $A^1$ is N; each of $A^2$, $A^3$, $A^4$ is CH or $CR^5$;
$A^2$ is N; each of $A^1$, $A^3$, $A^4$ is CH or $CR^5$;
$A^3$ is N; each of $A^1$, $A^2$, $A^4$ is CH or $CR^5$;
$A^4$ is N; each of $A^1$, $A^2$, $A^3$ is CH or $CR^5$;
$A^1$ and $A^4$ are N; each of $A^2$, and $A^3$ is CH or $CR^5$; or
each of $A^1$, $A^2$, $A^3$, $A^4$ is CH or $CR^5$.

Exemplary embodiments of Formula I compounds include wherein the compound has the structure of Formula (VIa), Formula (VIb), or Formula (VIc):

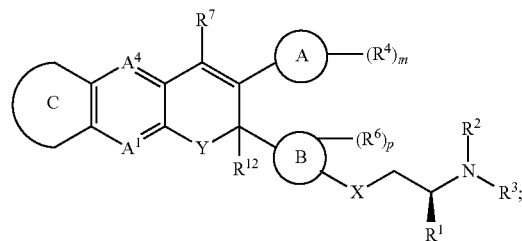

Formula (VIa)

wherein:
each of $A^1$ and $A^4$ is independently CH, $CR^5$ or N; and
ring C is a fused substituted or unsubstituted 5- or 6-membered heteroaryl;

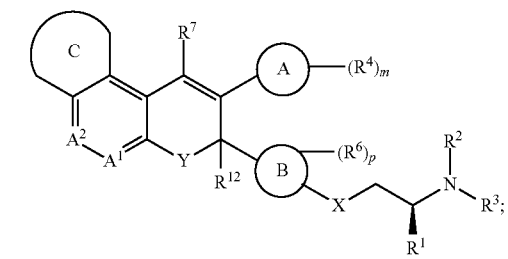

Formula (VIb)

wherein:
each of $A^1$ and $A^2$ is independently CH, $CR^5$ or N; and
ring C is a fused substituted or unsubstituted 5- or 6-membered heteroaryl; or Formula (VIc)

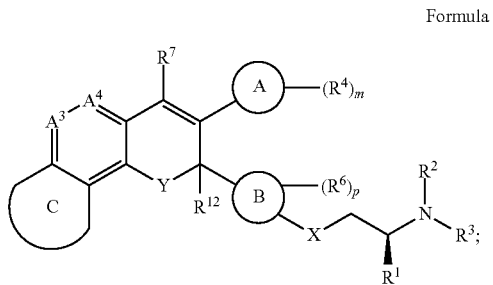

wherein:

each of $A^3$ and $A^4$ is independently CH, $CR^5$ or N; and ring C is a fused substituted or unsubstituted 5- or 6-membered heteroaryl or ring C is a fused pyrrolyl, fused imidazolyl, fused pyrazolyl, or fused triazolyl; or wherein each of $A^1$, $A^2$, $A^3$, and $A^4$ is CH or $CR^5$.

Exemplary embodiments of Formula I compounds include wherein:

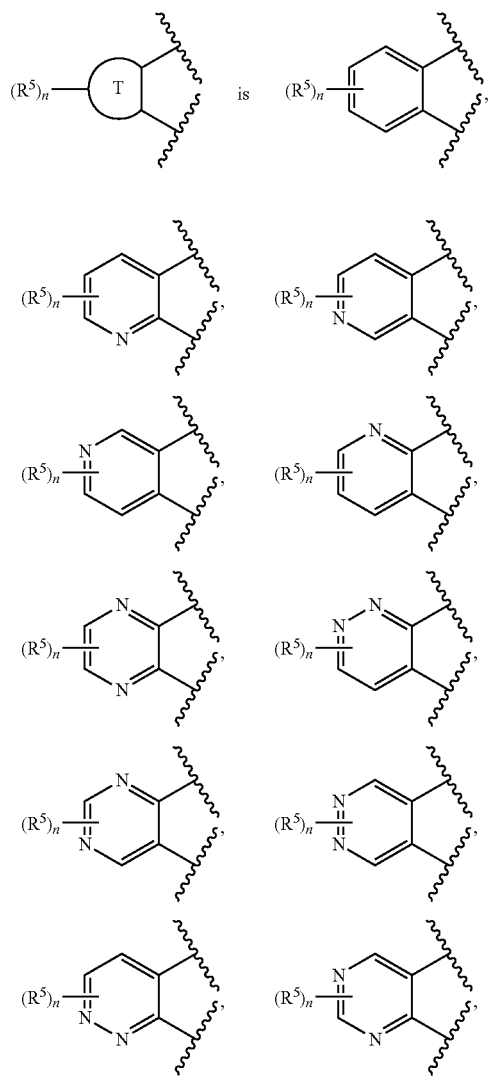

Exemplary embodiments of Formula I compounds include wherein:

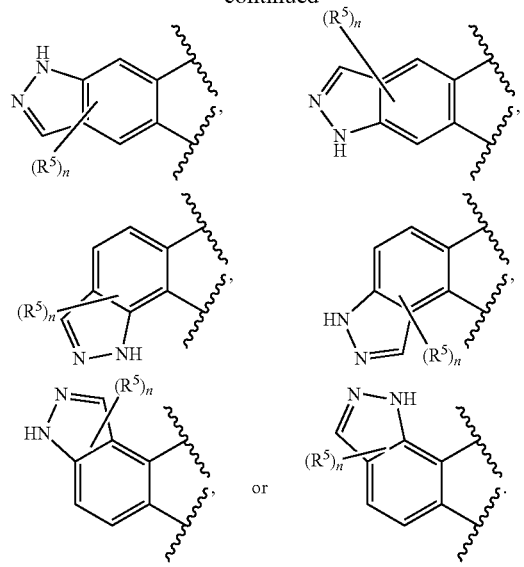

Exemplary embodiments of Formula I compounds include wherein:

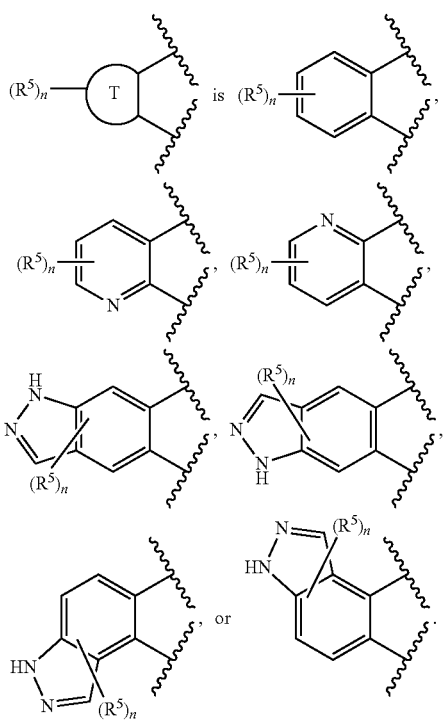

Exemplary embodiments of Formula I compounds include wherein:

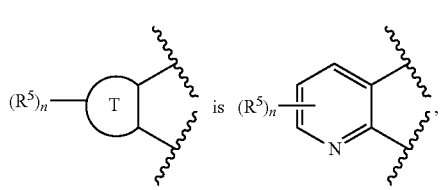

-continued

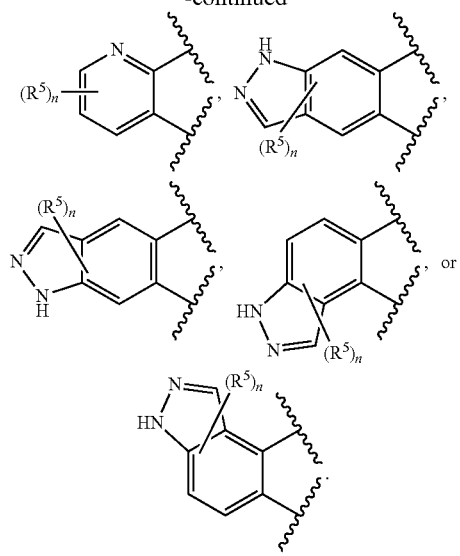

Exemplary embodiments of Formula I compounds include wherein:

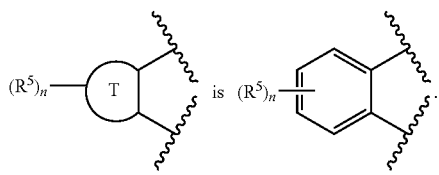

Exemplary embodiments of Formula I compounds include a pharmaceutically acceptable salt, or solvate thereof, wherein ring A is pyrrolyl, imidazolyl, pyrazolyl, triazolyl, tetrazolyl, oxazolyl, thiazolyl, isoxazolyl, isothiazolyl, oxadiazolyl, thiadiazolyl, thiophenyl, furanyl, phenyl, pyridinyl, pyridazinyl, pyrazinyl, pyrimidinyl, indolyl, indazolyl, benzimidazolyl, benzotriazolyl, benzoxazolyl, benzthiazolyl, quinolinyl, isoquinolinyl, cinnolinyl, phthalazinyl, quinazolinyl, or quinoxalinyl.

Exemplary embodiments of Formula I compounds include wherein ring A is pyrrolyl, imidazolyl, pyrazolyl, triazolyl, oxazolyl, thiazolyl, thiophenyl, furanyl, phenyl, pyridinyl, pyridazinyl, pyrazinyl, pyrimidinyl, indazolyl, benzimidazolyl, benzotriazolyl, or benzoxazolyl.

Exemplary embodiments of Formula I compounds include wherein

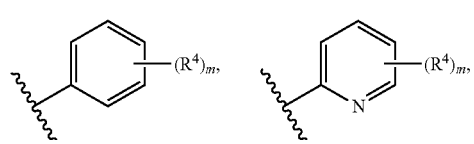

is:

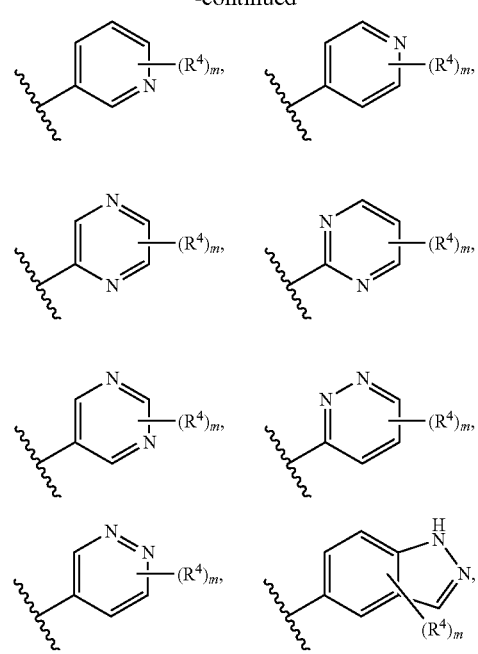

Exemplary embodiments of Formula I compounds include wherein

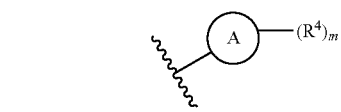

is:

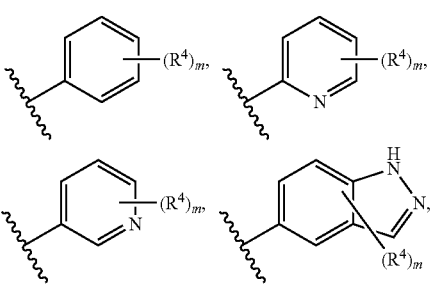

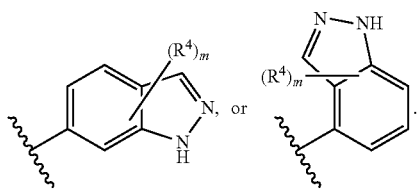
Exemplary embodiments of Formula I compounds include wherein
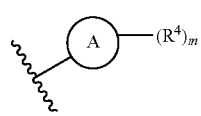
is:
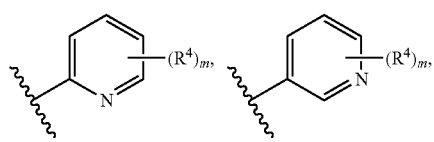
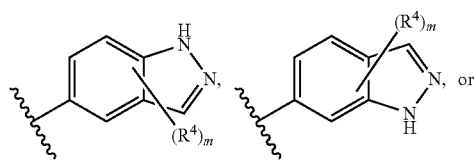
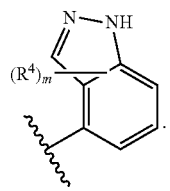
Exemplary embodiments of Formula I compounds include wherein
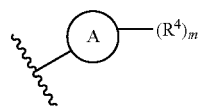
is:
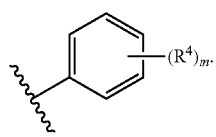
Exemplary embodiments of Formula I compounds include wherein
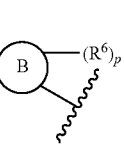
is:
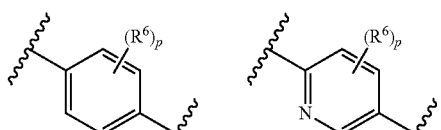
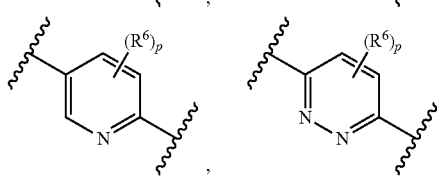
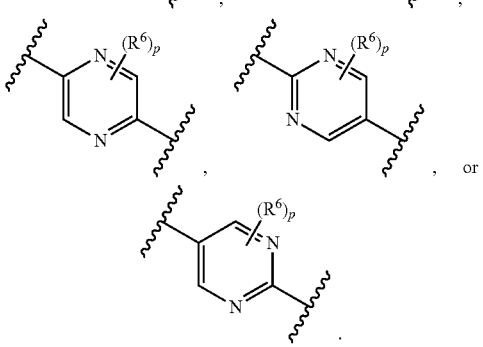
Exemplary embodiments of Formula I compounds include wherein
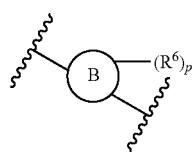
is:
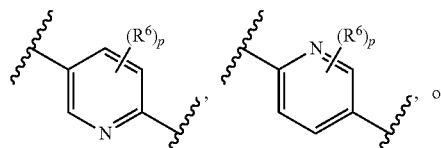
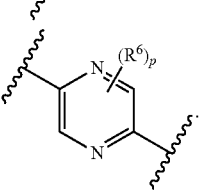

Exemplary embodiments of Formula I compounds include wherein ring A is phenyl; and

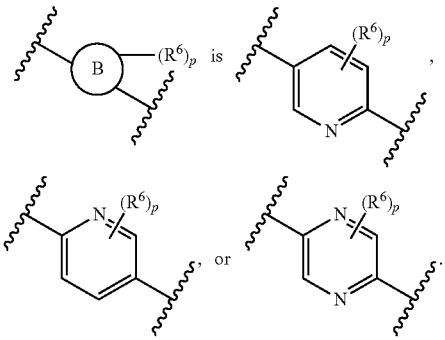

Exemplary embodiments of Formula I compounds include wherein ring A is pyrrolyl, imidazolyl, pyrazolyl, triazolyl, tetrazolyl, oxazolyl, thiazolyl, thiophenyl, furanyl, pyridinyl, pyridazinyl, pyrazinyl, pyrimidinyl, indazolyl, benzimidazolyl, benzotriazolyl, or benzoxazolyl; and

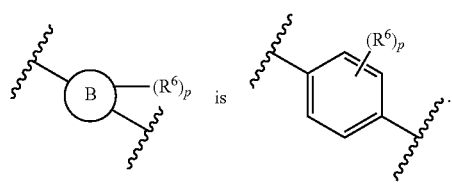

Exemplary embodiments of Formula I compounds include wherein ring A is phenyl; and

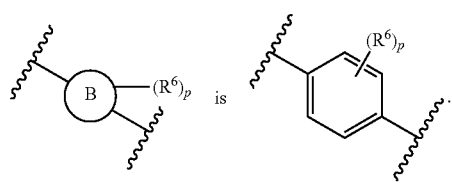

Exemplary embodiments of Formula I compounds include wherein:
$R^1$ is H, or $C_1$-$C_4$ alkyl;
$R^2$ and $R^3$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;
each $R^4$ is independently selected from H, halogen, —CN, —OH, —$OR^9$, —$SR^9$, —S(=O)$R^{10}$, —S(=O)$_2R^{10}$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
each $R^5$ is independently selected from H, halogen, —CN, —OH, —$OR^9$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
each $R^6$ is independently selected from H, halogen, —CN, —OH, $C_1$-$C_6$alkyl, $C_1$-$C_6$fluoroalkyl, $C_1$-$C_6$fluoroalkoxy, and $C_1$-$C_6$alkoxy;
$R^7$ is H, —$CH_3$ or —$CF_3$;
$R^{12}$ is H; and
Y is —O—, —S—, or N—$R^{13}$.

Exemplary embodiments of Formula I compounds include wherein:
$R^1$ is H or $C_1$-$C_4$alkyl;
$R^7$ is H, —$CH_3$ or —$CF_3$;
$R^{12}$ is H;
Y is —O—, or —S—; and
X is —O—, —S—, or —$CH_2$—.

Exemplary embodiments of Formula I compounds include wherein:
$R^2$ and $R^3$ are taken together with the N atom to which they are attached to form a substituted or unsubstituted monocyclic $C_2$-$C_6$ heterocycloalkyl, a substituted or unsubstituted bicyclic $C_5$-$C_{10}$ heterocycloalkyl, a substituted or unsubstituted monocyclic $C_1$-$C_5$heteroaryl, or a substituted or unsubstituted bicyclic $C_5$-$C_{10}$heteroaryl; or
$R^2$ and $R^3$ are taken together with the N atom to which they are attached to form a substituted or unsubstituted monocyclic heterocycloalkyl, a substituted or unsubstituted bicyclic heterocycloalkyl or a substituted or unsubstituted monocyclic heteroaryl.

Exemplary embodiments of Formula I compounds include wherein:
$R^2$ and $R^3$ are taken together with the N atom to which they are attached to form a substituted or unsubstituted monocyclic heterocycloalkyl; or
$R^2$ and $R^3$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted morpholinyl, substituted or unsubstituted piperazinyl, substituted or unsubstituted 3-azabicyclo[3.1.0]hexan-3-yl, substituted or unsubstituted 3-azabicyclo[3.2.0]heptan-3-yl, substituted or unsubstituted octahydrocyclopenta[c]pyrrolyl, substituted or unsubstituted octahydro-1H-isoindolyl, substituted or unsubstituted isoindolinyl, substituted or unsubstituted pyrazolyl, substituted or unsubstituted triazolyl, substituted or unsubstituted pyrrolyl, a substituted or unsubstituted imidazolyl, or substituted or unsubstituted isoindolyl.

Exemplary embodiments of Formula I compounds include wherein:
$R^2$ and $R^3$ are taken together with the N atom to which they are attached to form a substituted or unsubstituted azetidinyl, substituted or unsubstituted pyrrolidinyl, substituted or unsubstituted piperidinyl, or substituted or unsubstituted azepanyl.

Exemplary embodiments of Formula I compounds include wherein:
$R^1$ is H or —$CH_3$;
$R^2$ and $R^3$ are taken together with the N atom to which they are attached to form substituted or unsubstituted azetidinyl or substituted or unsubstituted pyrrolidinyl;
$R^7$ is —$CH_3$; and
$R^{12}$ is H.

Exemplary embodiments of Formula I compounds include wherein:
$R^1$ is H or —$CH_3$;
$R^2$ and $R^3$ are taken together with the N atom to which they are attached to form

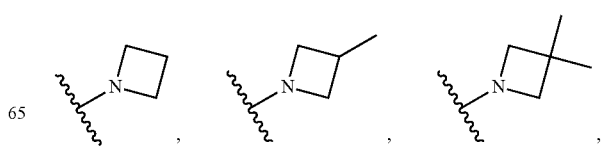

-continued
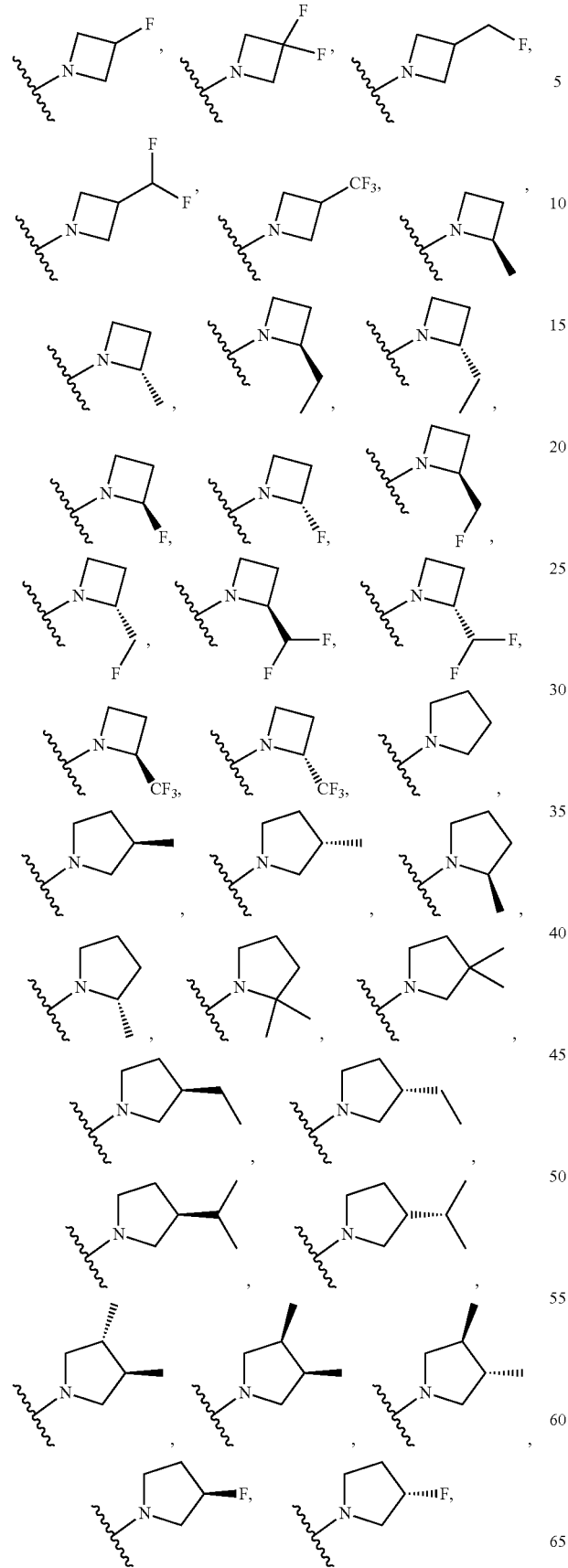
-continued
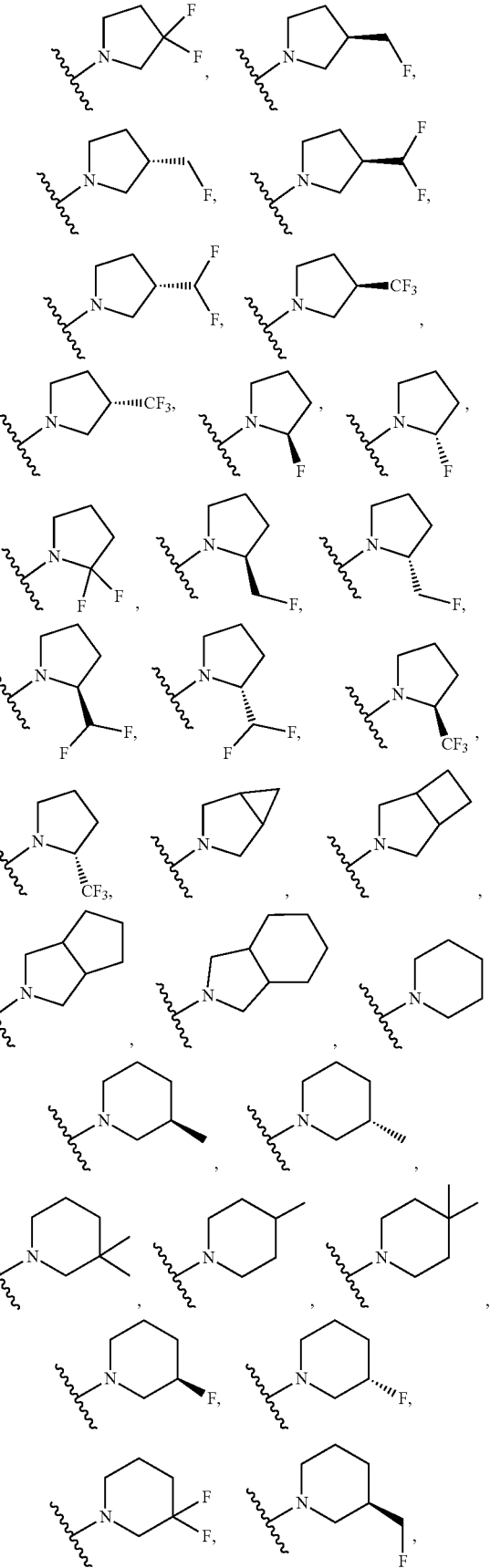

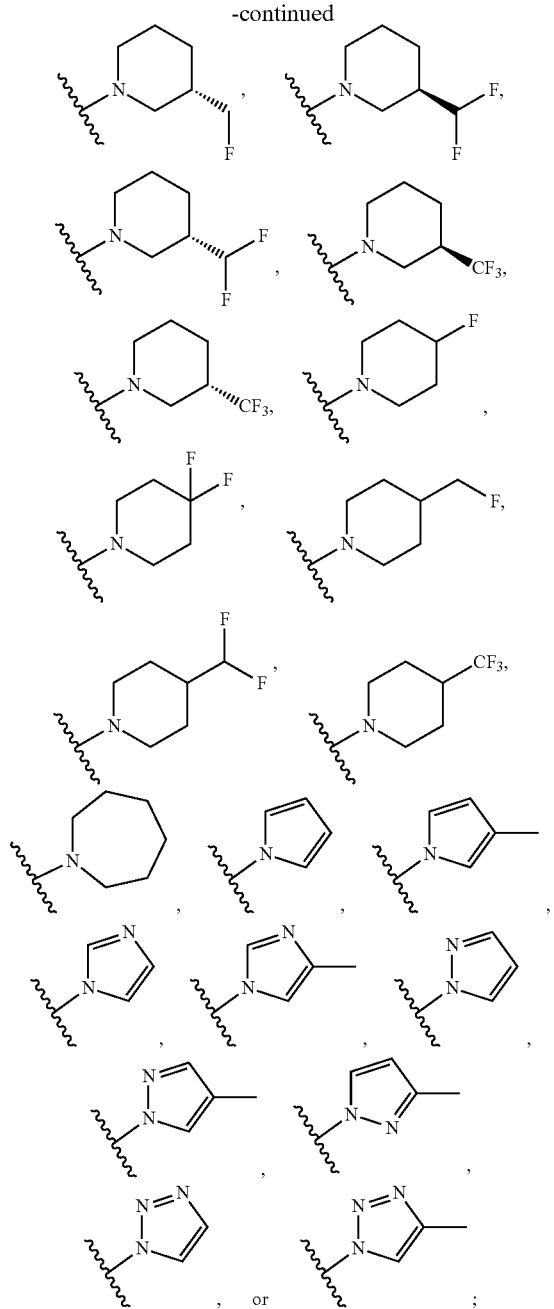

R[7] is —CH₃ or —CF₃; and
R[12] is H.
Exemplary embodiments of Formula I compounds include wherein:
  Y is —O— or —S—; and
  X is —O—, —S—, or —CH₂—.
Exemplary embodiments of Formula I compounds include wherein:
  Y is —O—.
Exemplary embodiments of Formula I compounds include wherein:
  X is —O—.
Exemplary embodiments of Formula I compounds include wherein:
  Y is —O—; and
  X is —O—.

Exemplary embodiments of Formula I compounds include wherein the compound of Formula (I) has the structure of Formula (VII), or a pharmaceutically acceptable salt, or solvate thereof:

Formula (VII)

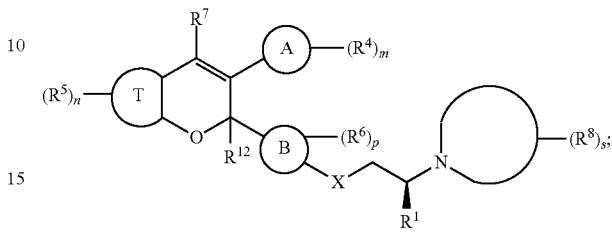

wherein:

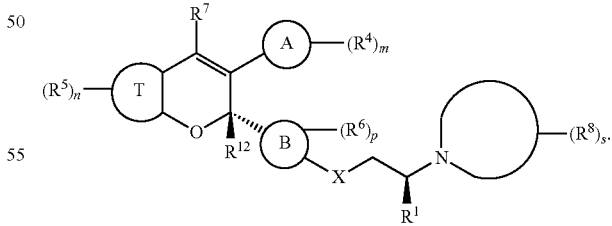

is a heterocycloalkyl or a heteroaryl;
  each R[8] is independently selected from F, Cl, —CN, —OH, —OR[9], —SR[9], —S(=O)R[10], —S(=O)₂R[10], substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$ alkoxy, and substituted or unsubstituted $C_1$-$C_6$ heteroalkyl;
  or R[8] is taken together with R[1] along with the intervening atoms joining R[8] to R[1] to form a 5-, 6-, or 7-membered ring; and
  s is 0, 1, 2, 3 or 4.
Exemplary embodiments of Formula (VII) compounds include wherein the compound has the structure of Formula (VIII):

Formula (VIII)

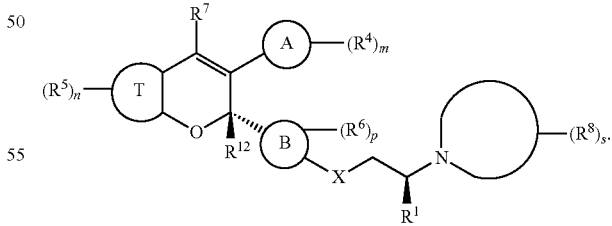

Exemplary embodiments of Formula (VII) compounds include wherein:
  R[1] is H or $C_1$-$C_4$alkyl;
  ring A is pyrrolyl, imidazolyl, pyrazolyl, triazolyl, oxazolyl, thiazolyl, thiophenyl, furanyl, pyridinyl, pyridazinyl, pyrazinyl, pyrimidinyl, phenyl, indazolyl, benzimidazolyl, benzotriazolyl, or benzoxazolyl;

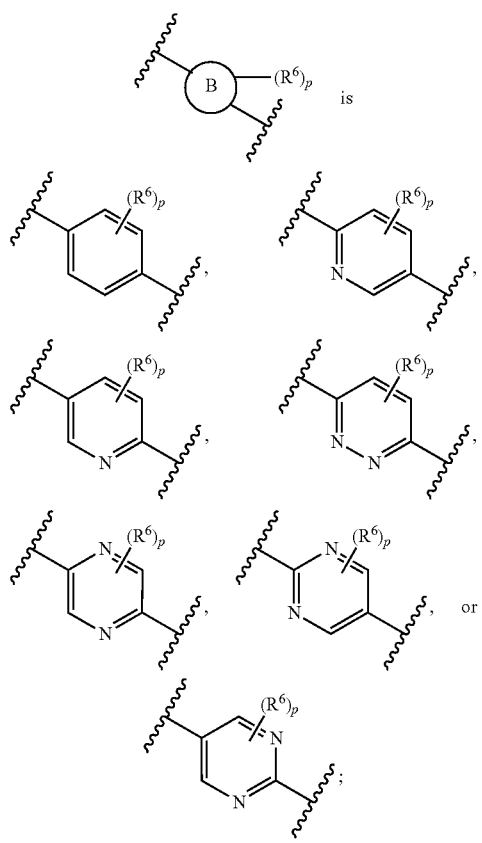

each R[4] is independently selected from H, halogen, —CN, —OH, —OR[9], —SR[9], —S(=O)R[10], —S(=O)$_2$R[10], $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each R[5] is independently selected from H, halogen, —OH, —OR[9], —SR[9], —S(=O)R[10], —S(=O)$_2$R[10], $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$heteroalkyl;

each R[6] is independently selected from H, halogen, —OH, $C_1$-$C_4$alkyl, $C_1$-$C_4$fluoroalkyl, $C_1$-$C_4$ fluoroalkoxy, and $C_1$-$C_4$ alkoxy;

R[7] is $C_1$-$C_4$ alkyl or $C_1$-$C_4$ fluoroalkyl;

X is —O—, —S—, or —CH$_2$—; and p is 0, 1, or 2.

Exemplary embodiments of Formula (VII) compounds include wherein:

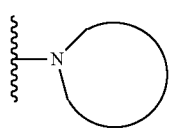

is azetidinyl, pyrrolidinyl, piperidinyl, azepanyl, morpholinyl, piperazinyl, 3-azabicyclo[3.1.0]hexan-3-yl, 3-azabicyclo[3.2.0]heptan-3-yl, octahydrocyclopenta[c]pyrrolyl, octahydro-1H-isoindolyl, isoindolinyl, pyrazolyl, triazolyl, pyrrolyl, imidazolyl, or isoindolyl; and each R[8] is independently selected from F, Cl, —OH, CN, $C_1$-$C_4$alkyl, $C_1$-$C_4$ fluoroalkyl, $C_1$-$C_4$ fluoroalkoxy, $C_1$-$C_4$ alkoxy, and $C_1$-$C_4$ heteroalkyl.

Exemplary embodiments of Formula (VII) compounds include wherein:

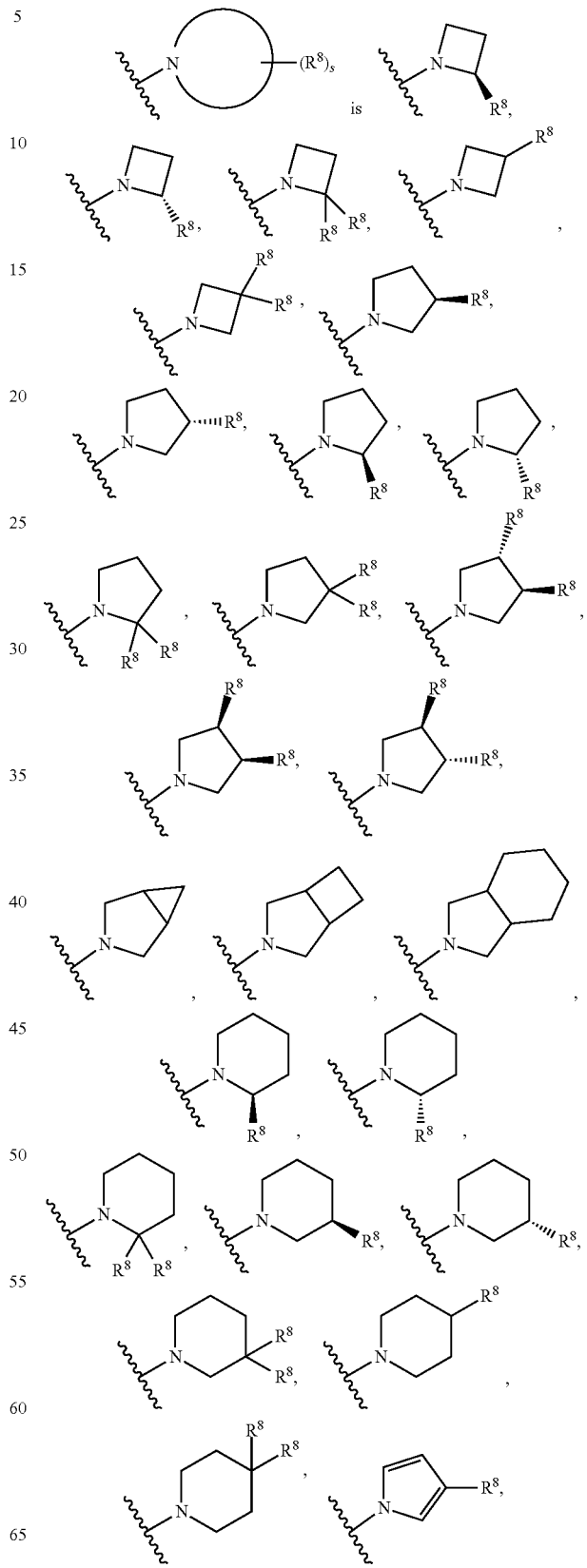

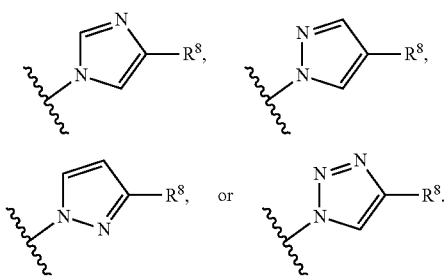

Exemplary embodiments of Formula (VII) compounds include wherein:

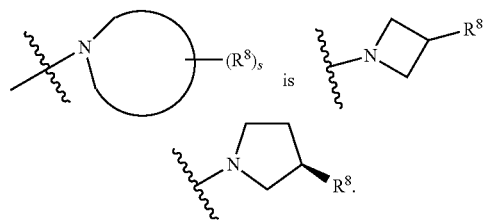

Exemplary embodiments of Formula (VII) compounds include wherein each $R^8$ is independently selected from H, F, Cl, —OH, —$CH_3$, —$CH_2CH_3$, —$CH(CH_3)_2$, —$CH_2F$, —$CHF_2$, —$CF_3$, —$CH_2CH_2F$, —$CH_2CHF_2$, —$CH_2CF_3$, —$OCF_3$, —$OCH_2CF_3$, —$OCH_3$, —$OCH_2CH_3$, —$CH_2OCH_3$, —$CH_2OCH_2CH_3$, and —$CH_2OH$.

Exemplary embodiments of Formula (VII) compounds include wherein each $R^8$ is independently selected from H, F, —$CH_3$, and —$CH_2F$.

Exemplary embodiments of Formula (VII) compounds include wherein each $R^8$ is independently selected from F, —$CH_3$, and —$CH_2F$.

Exemplary embodiments of Formula (VII) compounds include wherein:

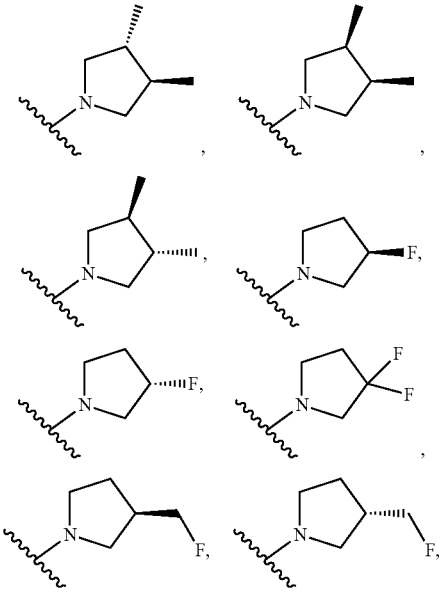

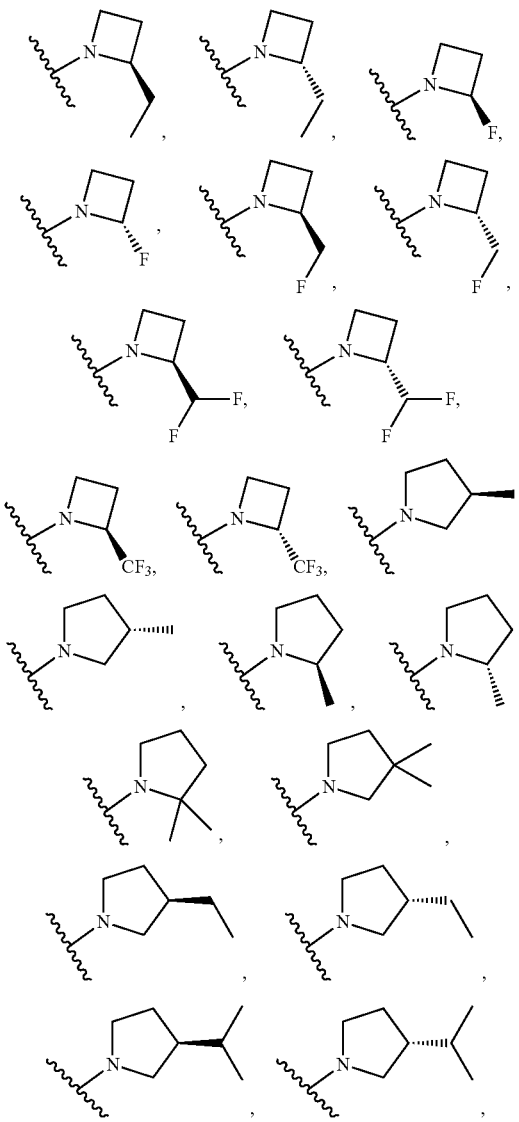

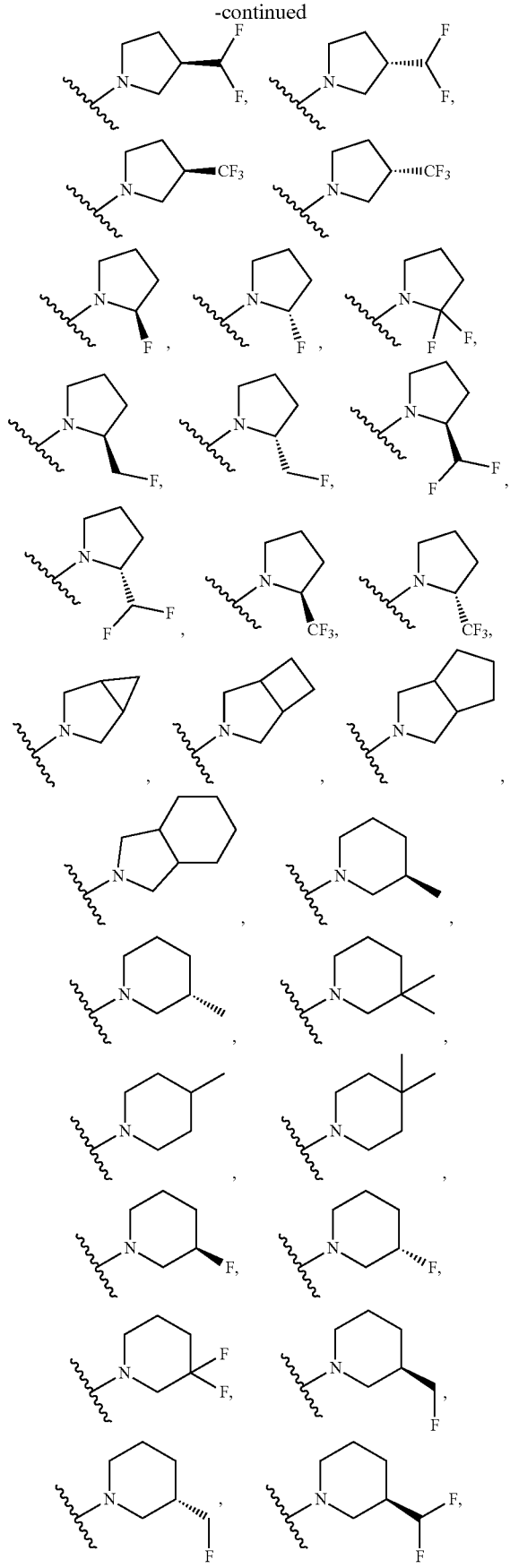
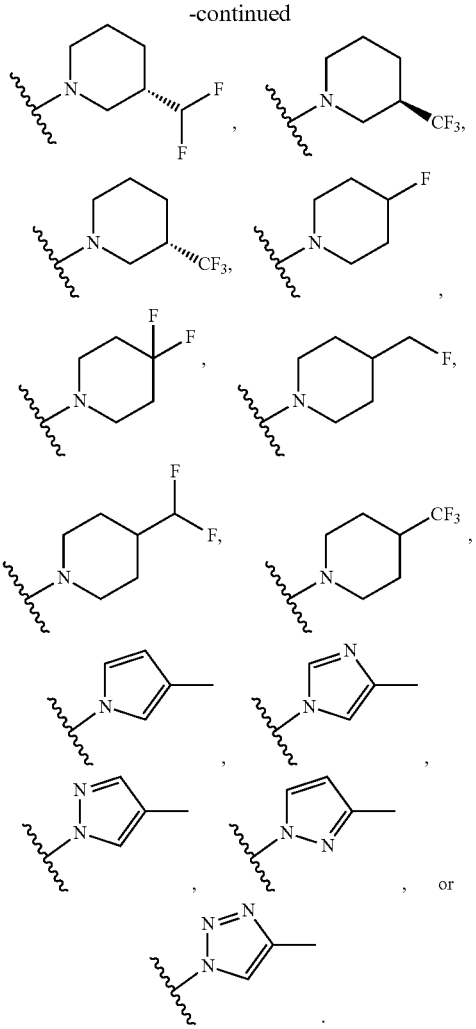
Exemplary embodiments of Formula (VII) compounds include wherein:
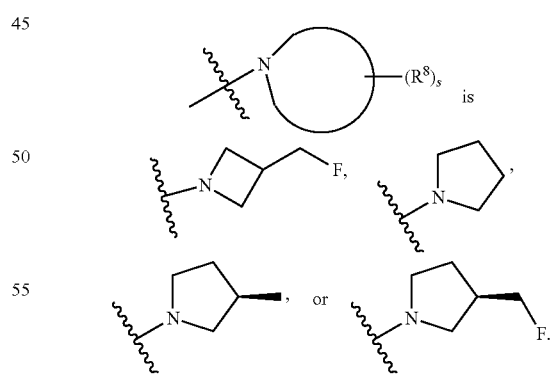
Exemplary embodiments of Formula (VII) compounds include wherein:
$R^1$ is H or —$CH_3$;
$R^7$ is —$CH_3$ or —$CF_3$;
$R^{12}$ is H;
X is —O—, —S—, or —$CH_2$—; and
p is 0, 1, or 2.

In one aspect, provided herein is a compound of Formula (IX), or a pharmaceutically acceptable salt, or solvate thereof:

Formula (IX)

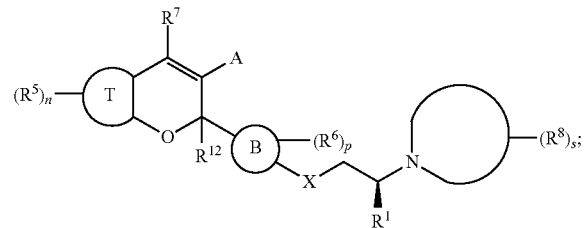

wherein:

X is —O—, —S—, —CH₂—, —NH— or —N(C₁-C₆alkyl)-;

A is substituted or unsubstituted $C_1$-$C_6$ alkyl, substituted or unsubstituted $C_2$-$C_6$alkenyl, or substituted or unsubstituted $C_2$-$C_6$ alkynyl;

ring B is phenyl or a monocyclic heteroaryl;

ring T is a fused phenyl, a fused monocyclic heteroaryl, or a fused bicyclic heteroaryl;

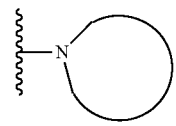

is a heterocycloalkyl ring;

each $R^8$ is independently selected from F, Cl, —CN, —OH, —OR⁹, —SR⁹, —S(=O)R¹⁰, —S(=O)₂R¹⁰, substituted or unsubstituted $C_1$-$C_6$alkyl, substituted or unsubstituted $C_1$-$C_6$fluoroalkyl, substituted or unsubstituted $C_1$-$C_6$ fluoroalkoxy, substituted or unsubstituted $C_1$-$C_6$ alkoxy, and substituted or unsubstituted $C_1$-$C_6$ heteroalkyl;

or $R^8$ is taken together with $R^1$ along with the intervening atoms joining $R^8$ to $R^1$ to form a 5-, 6-, or 7-membered ring;

s is 0, 1, 2, 3 or 4;

$R^1$ is H, F, $C_1$-$C_4$alkyl, or $C_1$-$C_4$fluoroalkyl;

each $R^5$ is independently selected from H, halogen, —CN, —OH, —OR⁹, —SR⁹, —S(=O)R¹⁰, —S(=O)₂R¹⁰, —NHS(=O)₂R¹⁰, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^6$ is independently selected from H, halogen, —CN, —OH, —OR⁹, —SR⁹, —S(=O)R¹⁰, —S(=O)₂R¹⁰, —NHS(=O)₂R¹⁰, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^7$ is H, halogen, CN, substituted or unsubstituted $C_1$-$C_6$alkyl, or substituted or unsubstituted $C_1$-$C_6$fluoroalkyl;

each $R^9$ is independently selected from H, —C(=O)R¹⁰, —C(=O)OR¹⁰, —C(=O)NHR¹⁰, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$ alkylene-(substituted or unsubstituted $C_3$-$C_{10}$ cycloalkyl), —$C_1$-$C_2$ alkylene-(substituted or unsubstituted $C_2$-$C_{10}$ heterocycloalkyl), —$C_1$-$C_2$ alkylene-(substituted or unsubstituted aryl), and —$C_1$-$C_2$ alkylene-(substituted or unsubstituted heteroaryl);

$R^{12}$ is H, or $C_1$-$C_4$ alkyl;

n is 0, 1, 2, 3 or 4; and p is 0, 1, 2, 3 or 4.

Exemplary embodiments of Formula (IX) compounds include wherein A is substituted or unsubstituted $C_1$-$C_6$ alkyl or $C_2$-$C_6$ alkenyl.

Exemplary embodiments of Formula (IX) compounds include wherein:

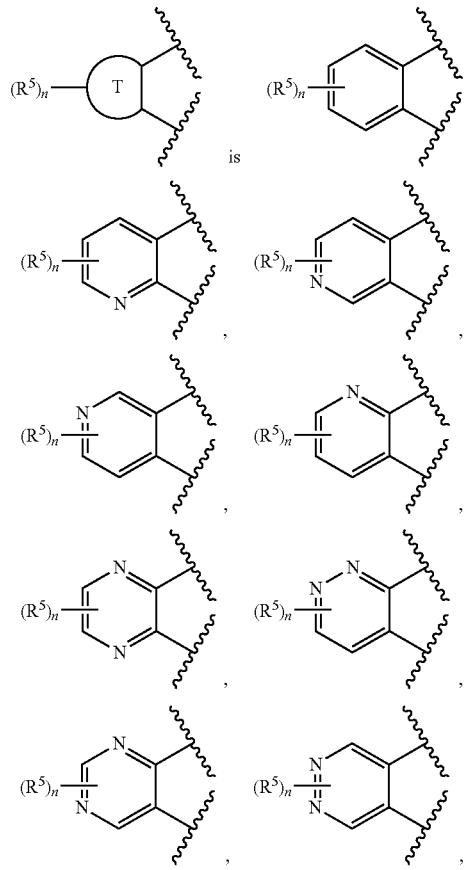

is

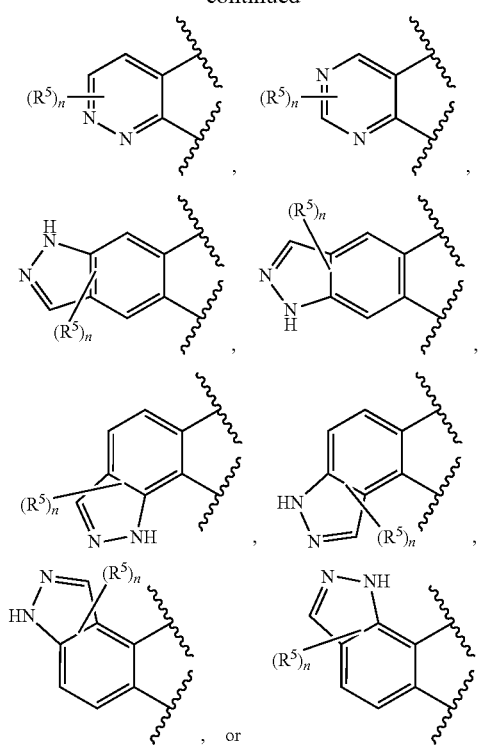

, or .

Exemplary embodiments of Formula (IX) compounds include wherein:

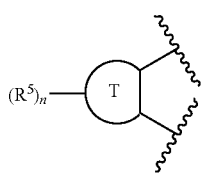

is:

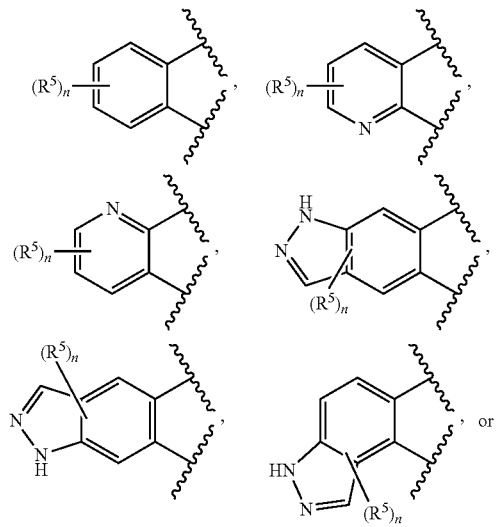

, or

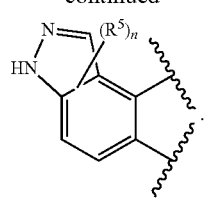

Exemplary embodiments of Formula (IX) compounds include wherein:

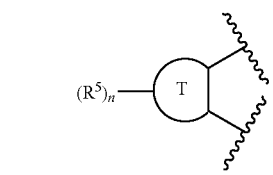

is:

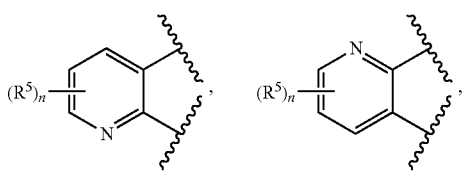

, or .

Exemplary embodiments of Formula (IX) compounds include wherein:

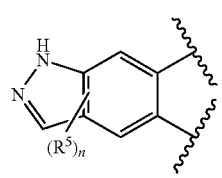 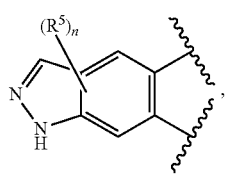

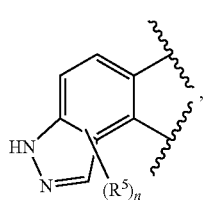 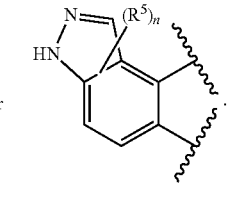

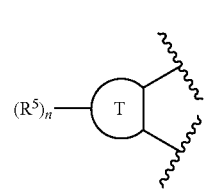 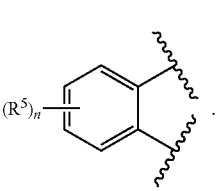

, or .

Exemplary embodiments of Formula (IX) compounds include wherein:

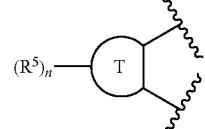 is 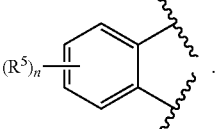 .

In one aspect, provided herein is a compound of Formula (X), or a pharmaceutically acceptable salt, or solvate thereof:

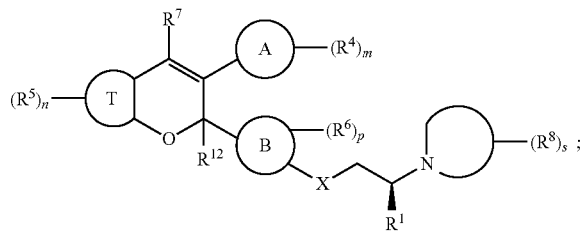

Formula (X)

wherein:

X is —O—, —S—, —CH$_2$—, —NH— or —N(C$_1$-C$_6$alkyl)-;

ring A is cycloalkyl or heterocycloalkyl;

ring B is phenyl or a monocyclic heteroaryl;

ring T is a fused phenyl, a fused monocyclic heteroaryl, or a fused bicyclic heteroaryl;

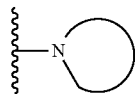

is a heterocycloalkyl ring;

each R$^8$ is independently selected from F, Cl, —CN, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

or R$^8$ is taken together with R$^1$ along with the intervening atoms joining R$^8$ to R$^1$ to form a 5-, 6-, or 7-membered ring;

s is 0, 1, 2, 3 or 4;

R$^1$ is H, F, C$_1$-C$_4$alkyl, or C$_1$-C$_4$fluoroalkyl;

each R$^4$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

each R$^5$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

each R$^6$ is independently selected from H, halogen, —CN, —OH, —OR$^9$, —SR$^9$, —S(=O)R$^{10}$, —S(=O)$_2$R$^{10}$, —NHS(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

R$^7$ is H, halogen, CN, substituted or unsubstituted C$_1$-C$_6$alkyl, or substituted or unsubstituted C$_1$-C$_6$fluoroalkyl;

each R$^9$ is independently selected from H, —C(=O)R$^{10}$, —C(=O)OR$^{10}$, —C(=O)NHR$^{10}$, substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl); or each R$^{10}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl);

R$^{12}$ is H, or C$_1$-C$_4$alkyl;

m is 0, 1, 2, 3, or 4;

n is 0, 1, 2, 3 or 4; and p is 0, 1, 2, 3 or 4.

Exemplary embodiments of Formula (IX) compounds include wherein:

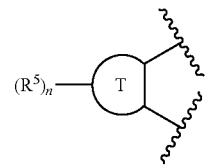

is:

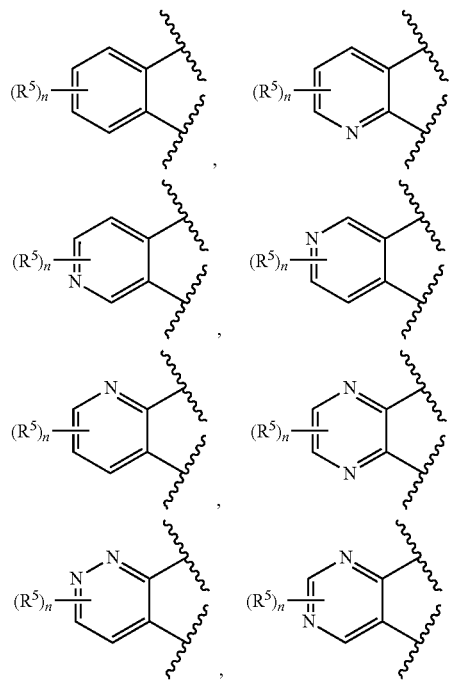

,

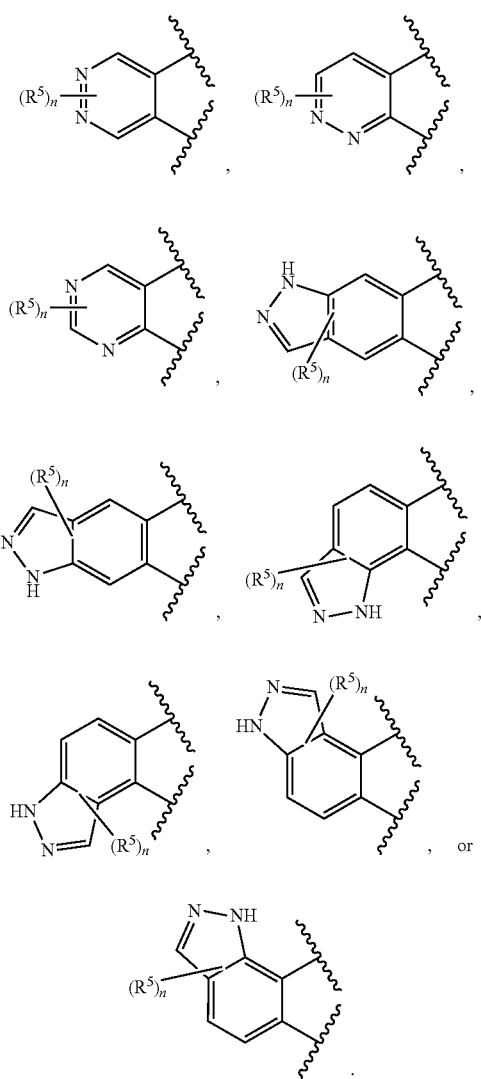
Exemplary embodiments of Formula (IX) compounds include wherein:
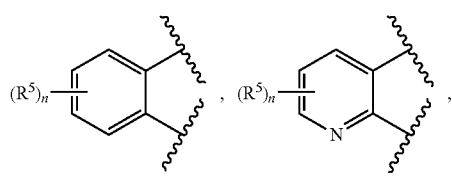
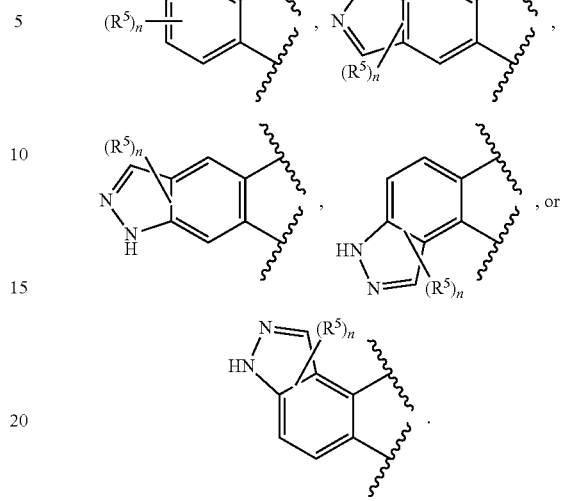
Exemplary embodiments of Formula (IX) compounds include wherein:
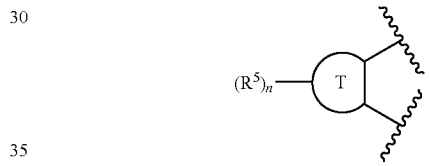
is:
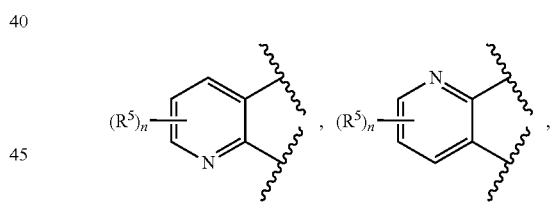
Exemplary embodiments of Formula (IX) compounds include wherein the compound has the structure of Formula (Xa):

Formula (Xa)

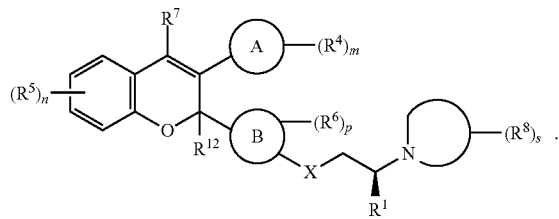

Exemplary embodiments of Formula (X) compounds include wherein the compound has the structure of Formula (Xb):

Formula (Xb)

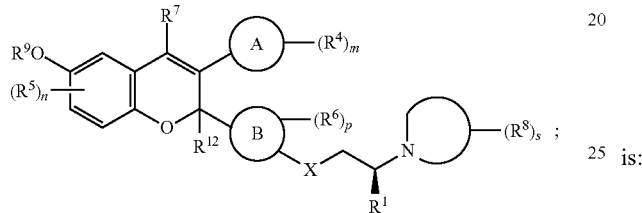

wherein n is 0, 1, 2, or 3.

Exemplary embodiments of Formula (X) compounds include wherein the compound has the structure of Formula (Xc):

Formula (Xc)

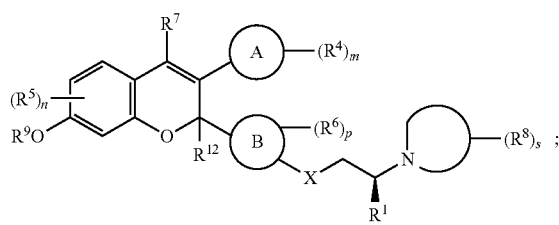

wherein n is 0, 1, 2, or 3.

Exemplary embodiments of Formula (IX) and (IX) compounds include wherein ring A is cycloalkyl.

Exemplary embodiments of Formula (IX) and (IX) compounds include wherein:

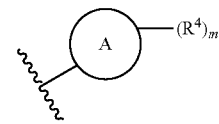

is:

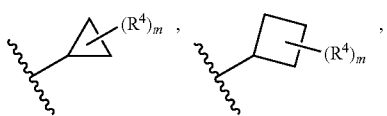

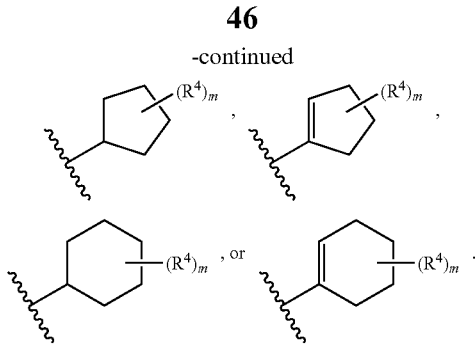

Exemplary embodiments of Formula (IX) and (IX) compounds include wherein

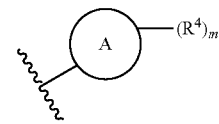

is:

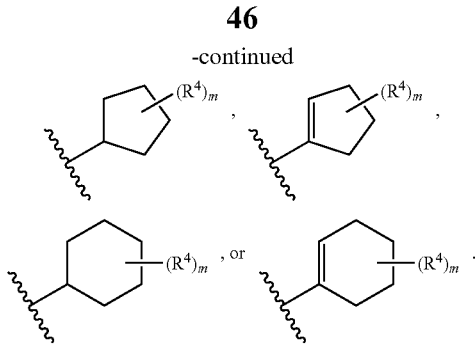

Exemplary embodiments of Formula (IX) and (IX) compounds include wherein ring A is heterocycloalkyl.

Exemplary embodiments of Formula (IX) and (IX) compounds include wherein

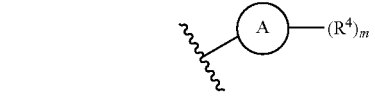

is:

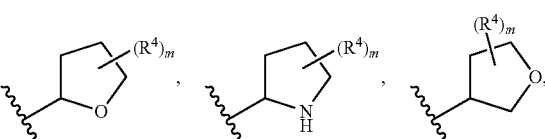

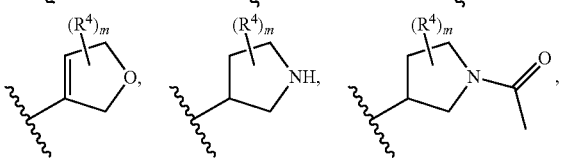

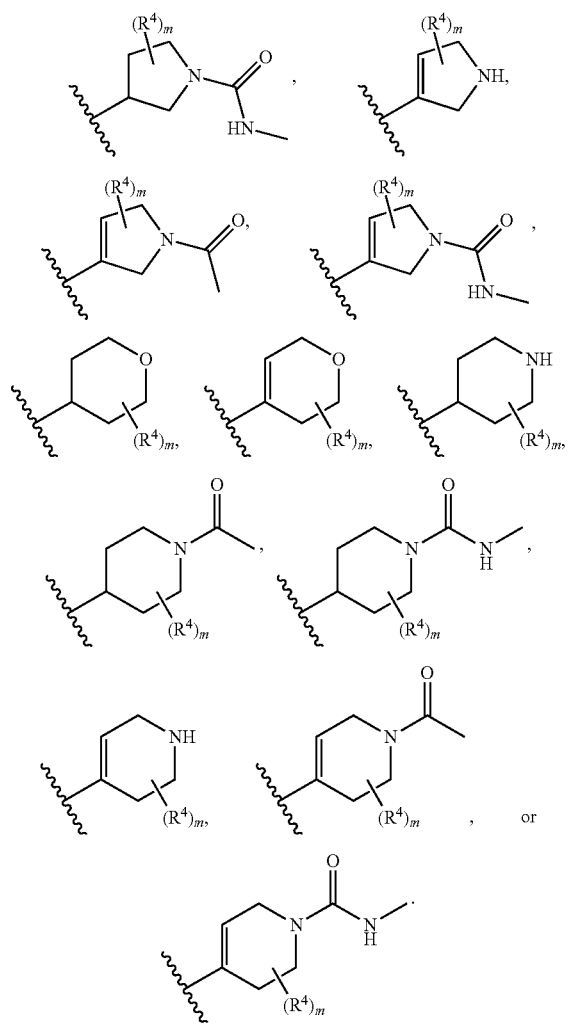
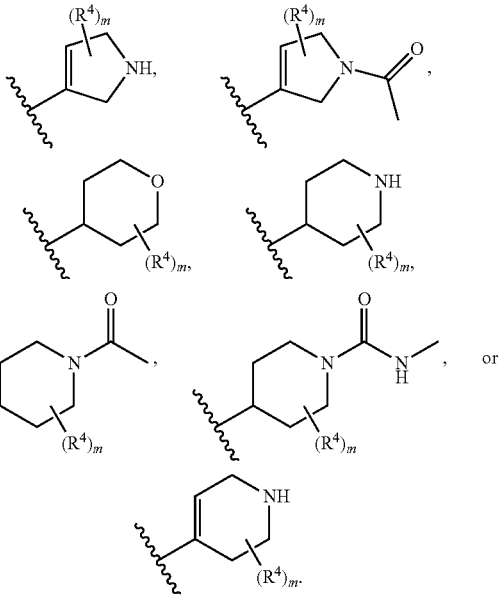
Exemplary embodiments of Formula (IX) and (IX) compounds include wherein
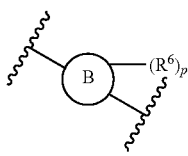
is:
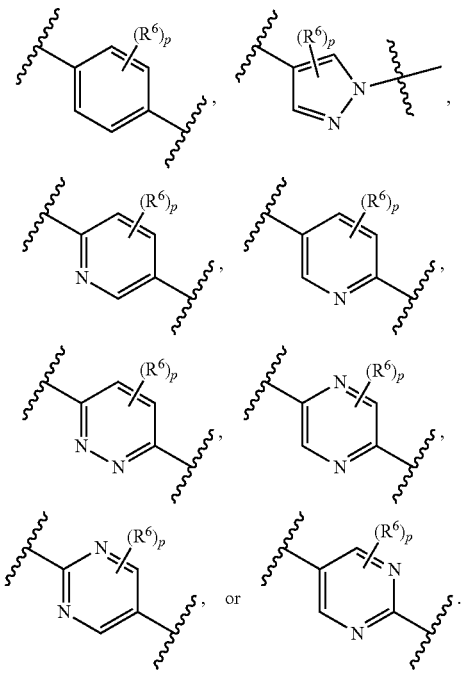
Exemplary embodiments of Formula (IX) and (IX) compounds include wherein
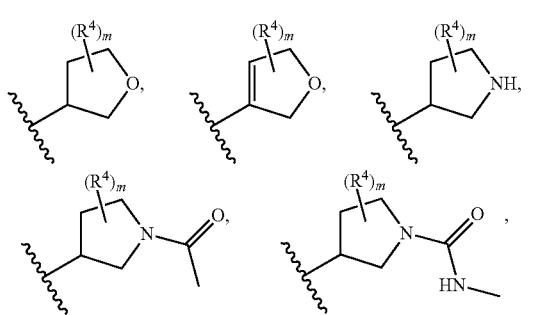
is:

Exemplary embodiments of Formula (IX) and (IX) compounds include wherein
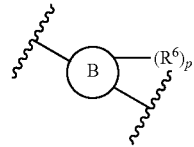
is:
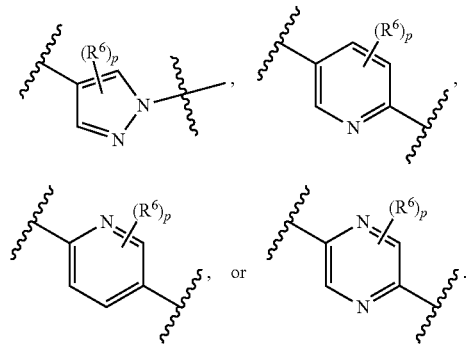
Exemplary embodiments of Formula (IX) and (IX) compounds include wherein:
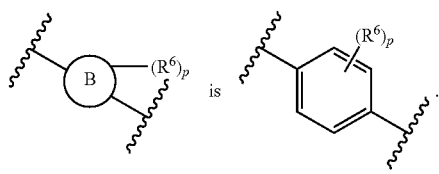
Exemplary embodiments of Formula (IX and IX) compounds include wherein
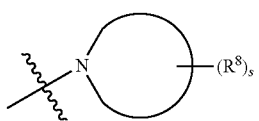
is:
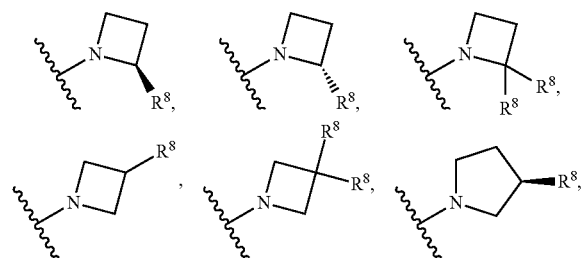
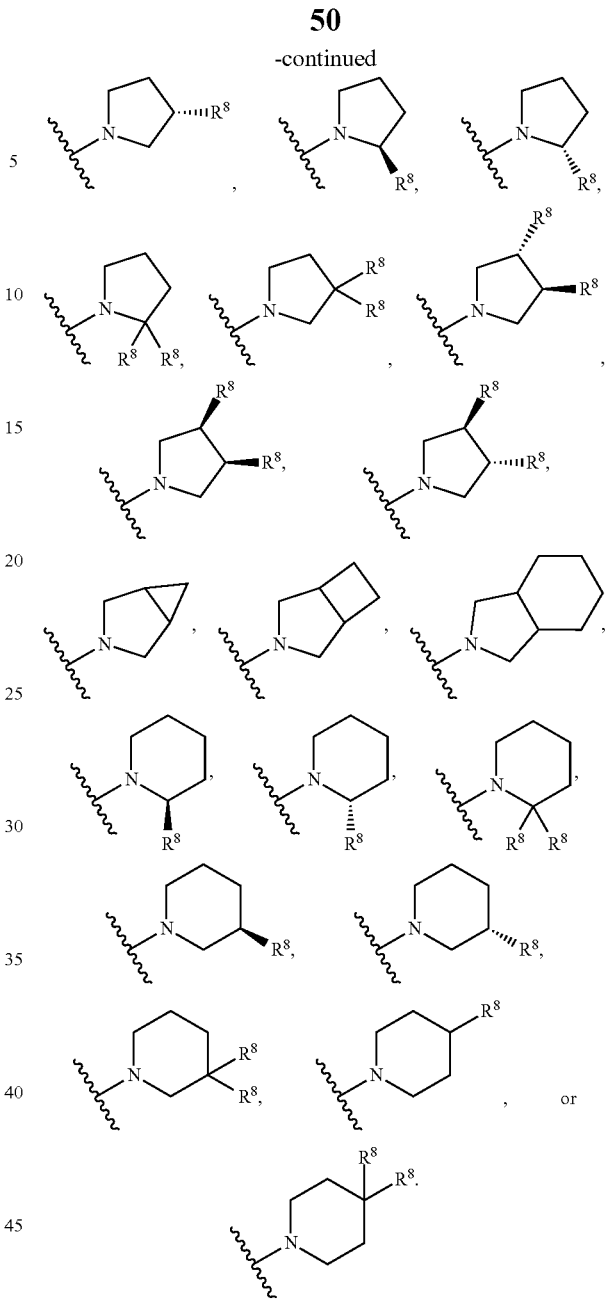
Exemplary embodiments of Formula (IX) and (IX) compounds include wherein:
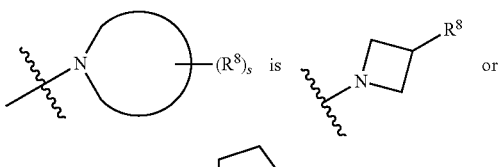
Exemplary embodiments of Formula (IX) and (IX) compounds include wherein:

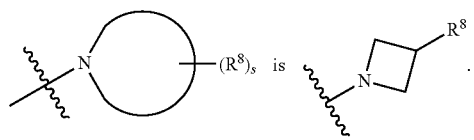

Exemplary embodiments of Formula (IX) and (IX) compounds include wherein:

each $R^8$ is independently selected from H, F, Cl, —OH, —CH$_3$, —CH$_2$CH$_3$, —CH(CH$_3$)$_2$, —CH$_2$F, —CHF$_2$, —CF$_3$, —CH$_2$CH$_2$F, —CH$_2$CHF$_2$, —CH$_2$CF$_3$, —OCF$_3$, —OCH$_2$CF$_3$, —OCH$_3$, —OCH$_2$CH$_3$, —CH$_2$OCH$_3$, —CH$_2$OCH$_2$CH$_3$, and —CH$_2$OH.

Exemplary embodiments of Formula (IX) and (IX) compounds include wherein:

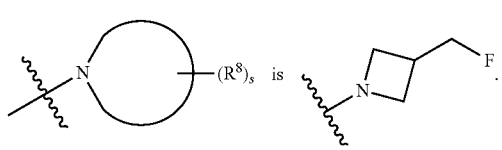

Exemplary embodiments of Formula (IX) and (IX) compounds include wherein:

$R^1$ is H, or $C_1$-$C_4$ alkyl;

each $R^4$ is independently selected from H, halogen, —CN, —OH, —OR$^9$, —SR$^9$, —S(=O)R$^{10}$, —S(=O)$_2$R$^{10}$, $C_1$-$C_6$ alkyl, $C_1$-$C_6$ fluoroalkyl, $C_1$-$C_6$ fluoroalkoxy, $C_1$-$C_6$ alkoxy, and $C_1$-$C_6$ heteroalkyl;

each $R^5$ is independently selected from H, halogen, —CN, —OH, —OR$^9$, $C_1$-$C_6$ alkyl, $C_1$-$C_6$ fluoroalkyl, $C_1$-$C_6$ fluoroalkoxy, $C_1$-$C_6$ alkoxy, and $C_1$-$C_6$ heteroalkyl;

each $R^6$ is independently selected from H, halogen, —CN, —OH, $C_1$-$C_6$ alkyl, $C_1$-$C_6$ fluoroalkyl, $C_1$-$C_6$ fluoroalkoxy, and $C_1$-$C_6$ alkoxy;

$R^7$ is H, —CH$_3$ or —CF$_3$; and $R^{12}$ is H.

Exemplary embodiments of Formula (IX) and (IX) compounds include wherein:

$R^1$ is H or —CH$_3$;

$R^7$ is H or —CH$_3$;

$R^{12}$ is H; and

X is —O—, —S—, or —CH$_2$—.

Exemplary embodiments of Formula (IX) and (IX) compounds include wherein $R^1$ is H.

Exemplary embodiments of Formula (IX) and (IX) compounds include wherein $R^7$ is —CH$_3$.

Exemplary embodiments of Formula (IX) and (IX) compounds include wherein $R^{12}$ is H.

Exemplary embodiments of Formula (IX) and (IX) compounds include wherein X is O.

Any combination of the groups described above for the various variables is contemplated herein. Throughout the specification, groups and substituents thereof are chosen by one skilled in the field to provide stable moieties and compounds.

In some embodiments, compounds of Formulas (I)-(X) have one of the following structures:

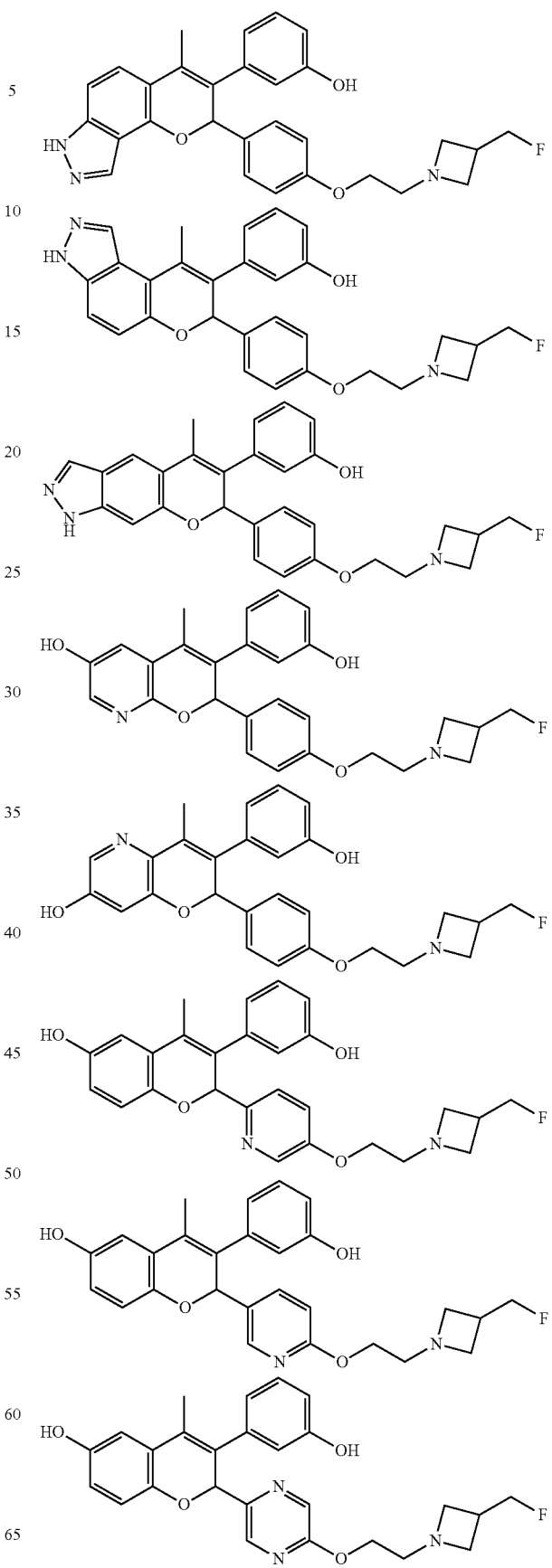

53
-continued
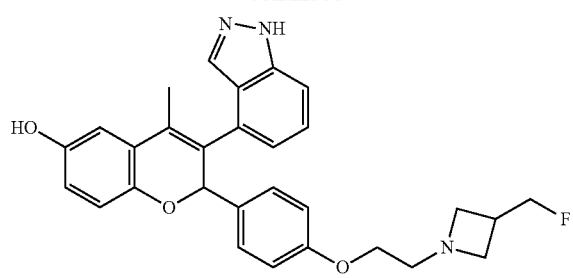
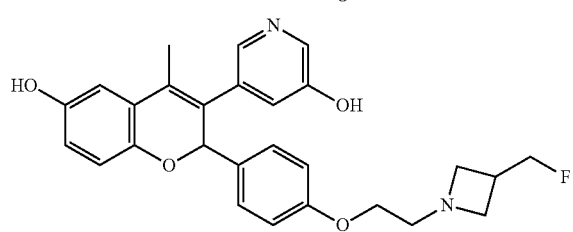
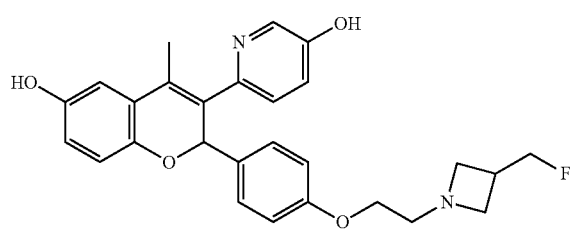
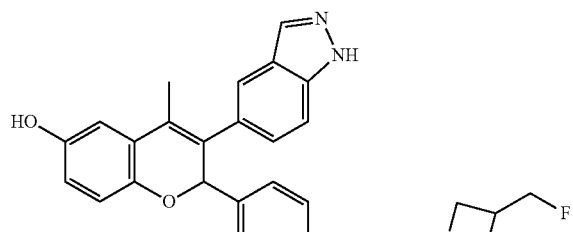
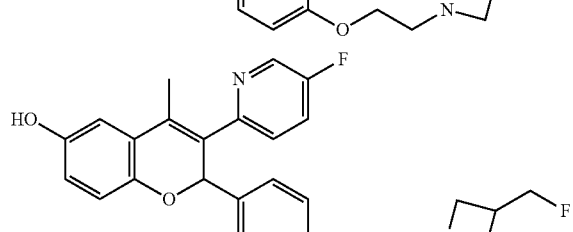
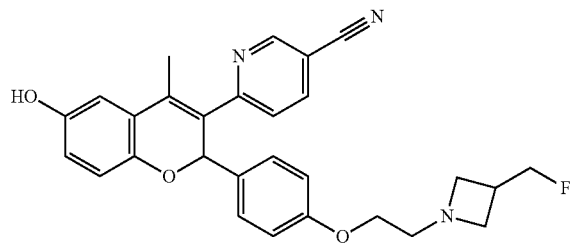
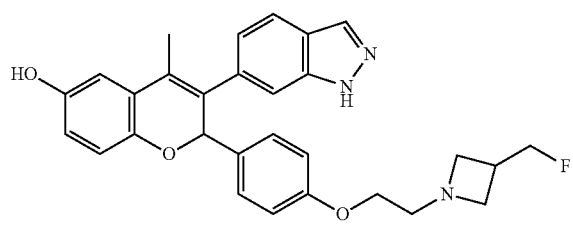
54
-continued
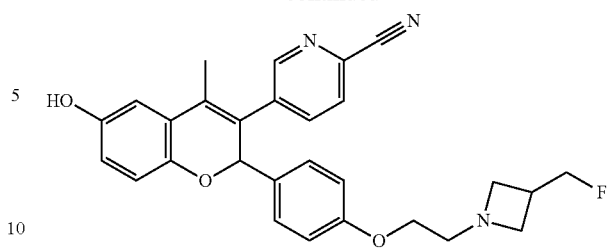
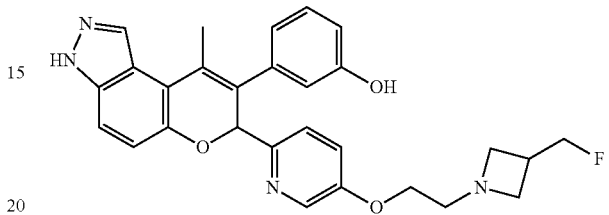
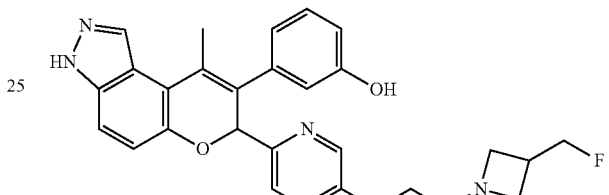
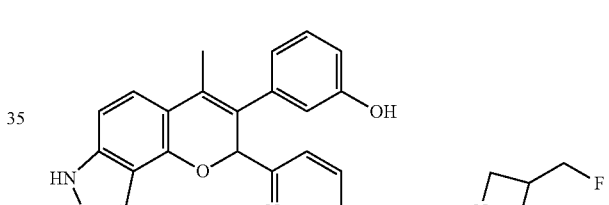
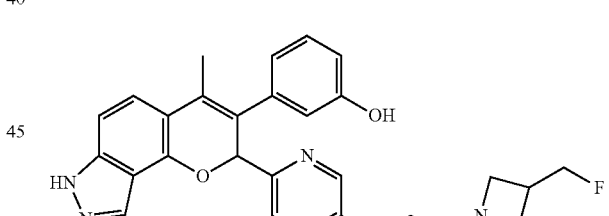
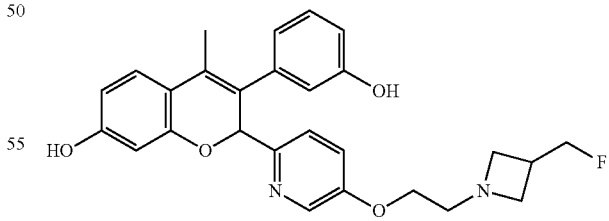
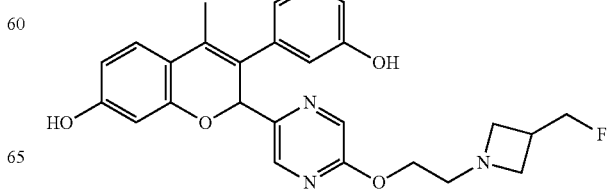

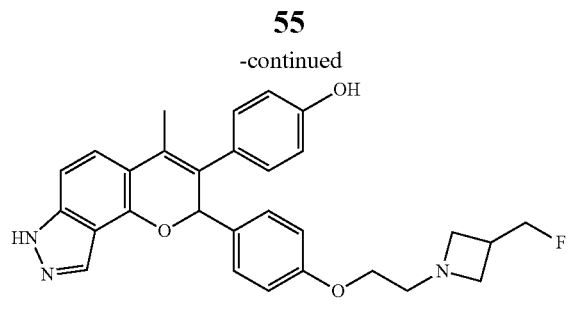
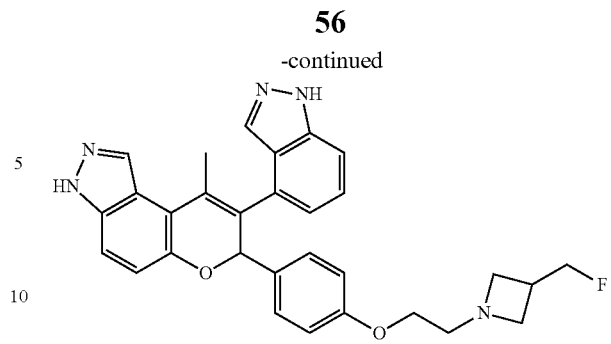
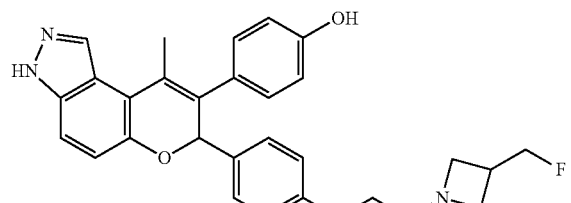
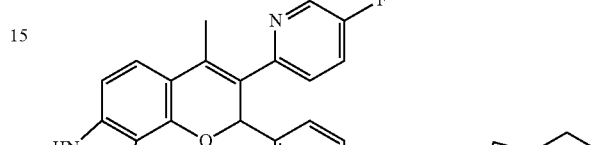
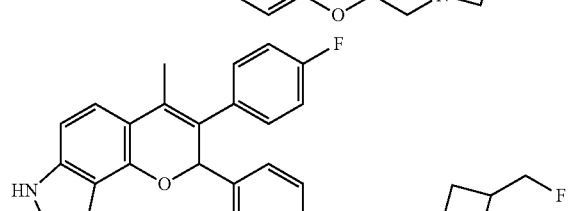
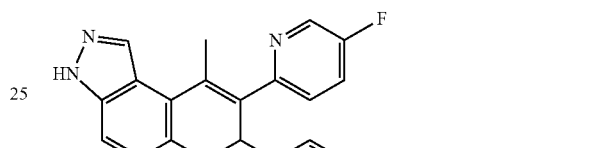
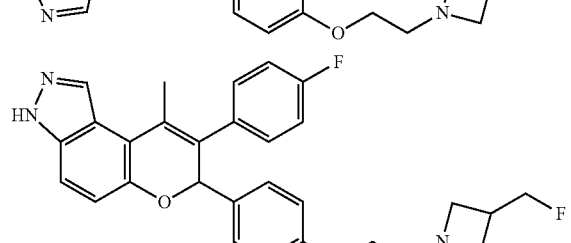
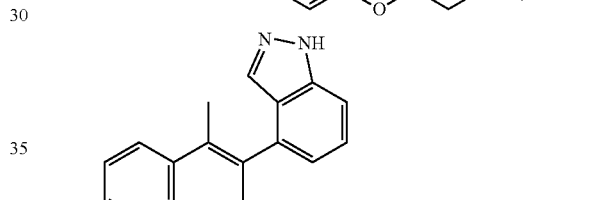
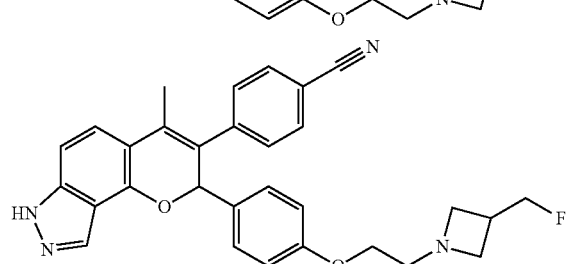
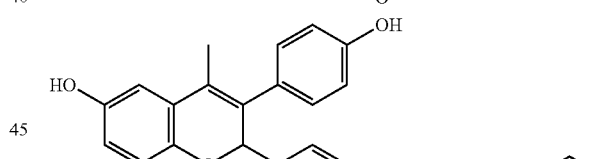
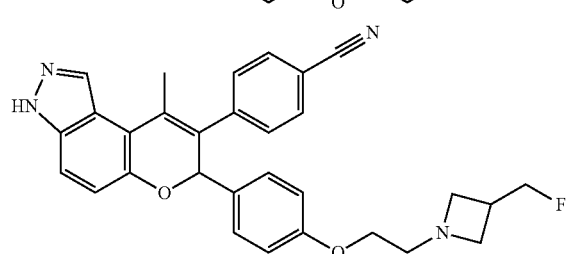
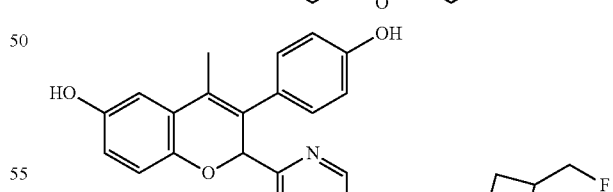
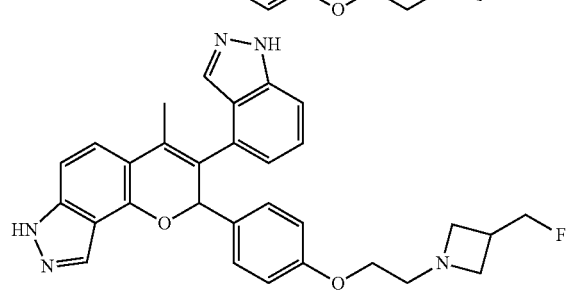
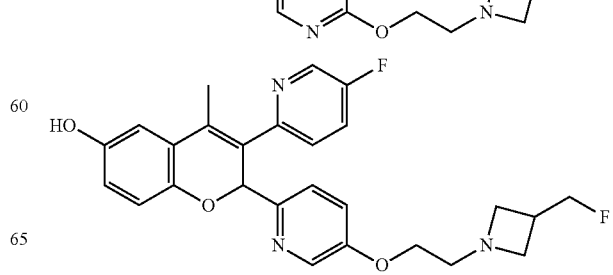

57
-continued
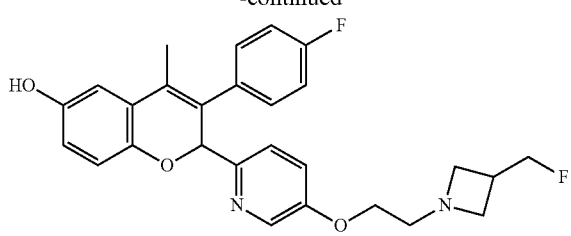
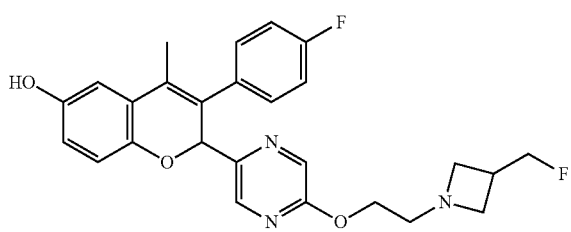
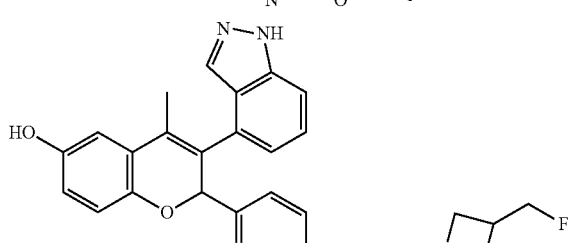
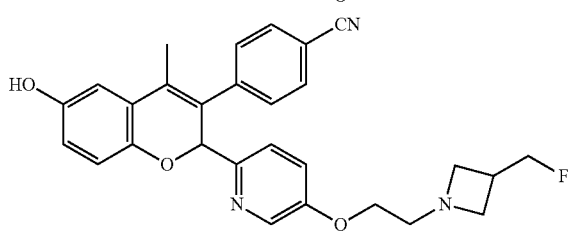
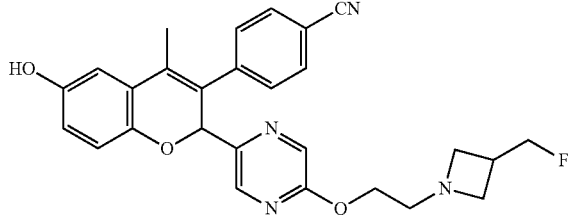
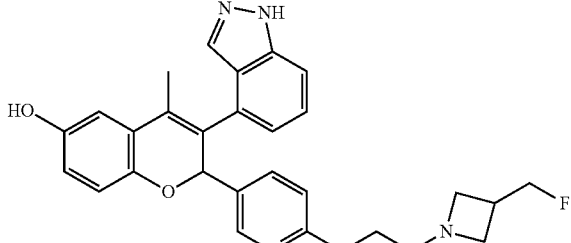
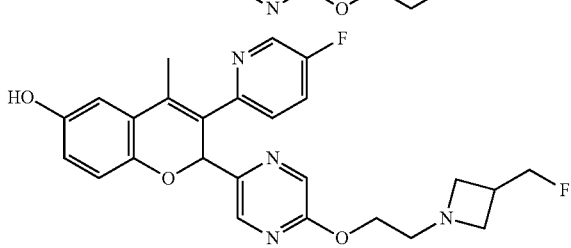
58
-continued
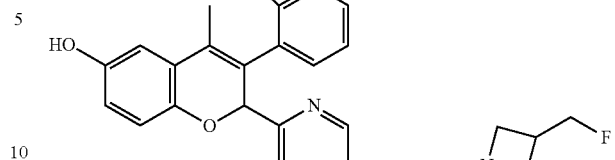
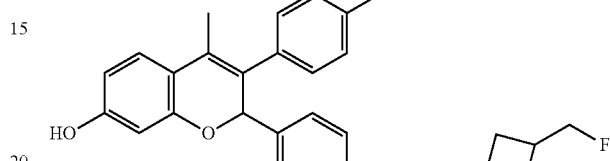
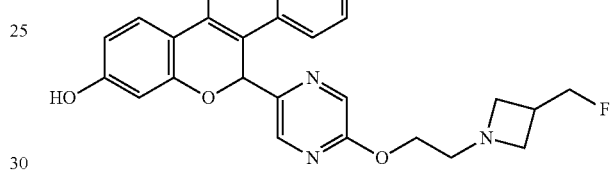
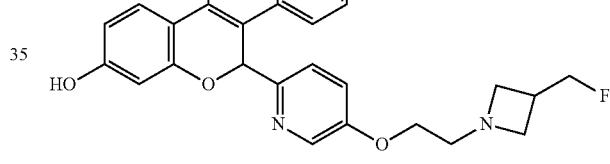
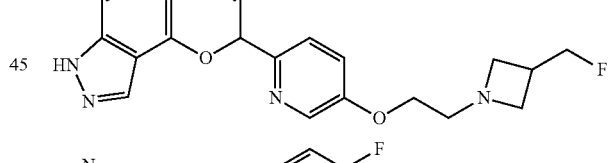
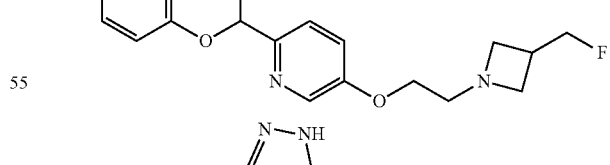
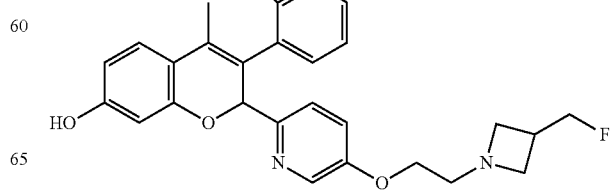

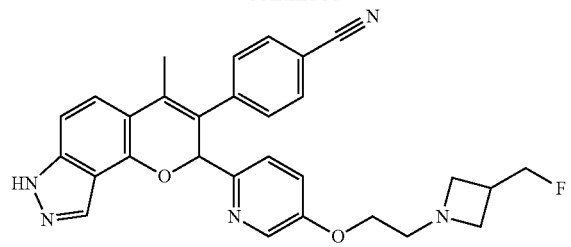
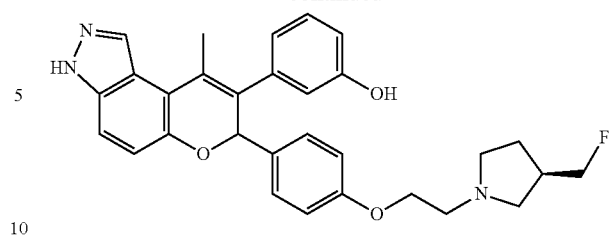

61
-continued
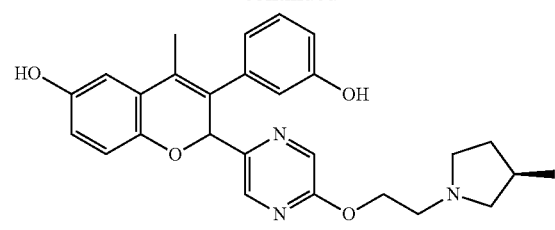
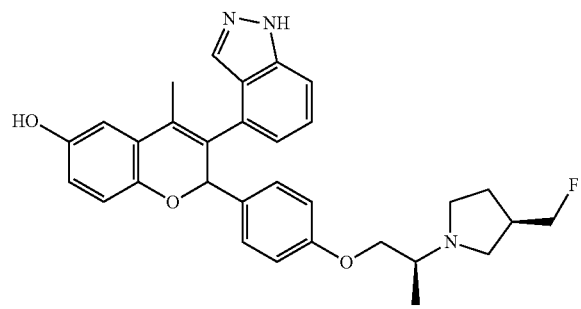
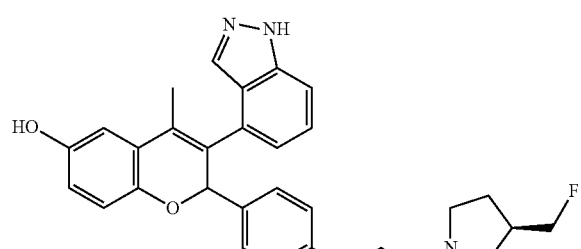
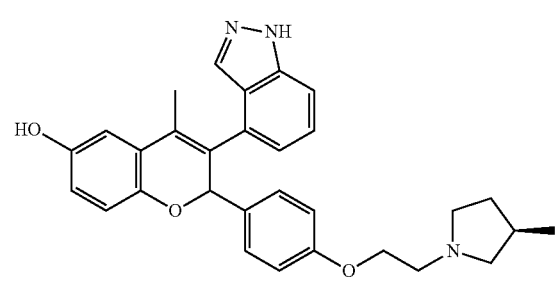
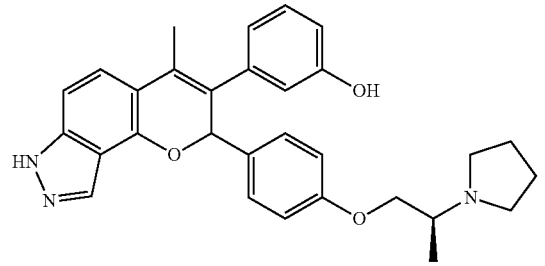
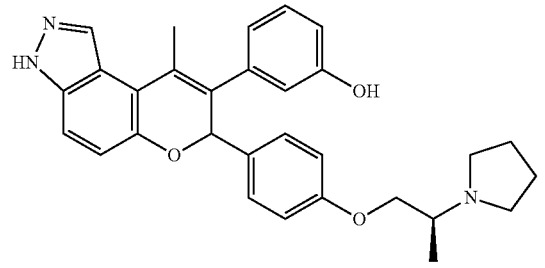
62
-continued
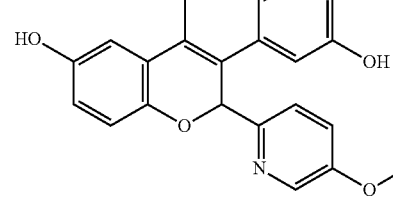
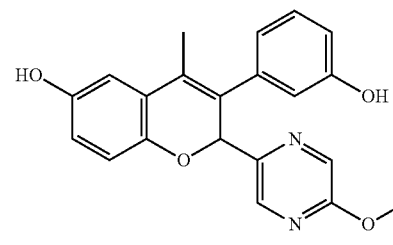
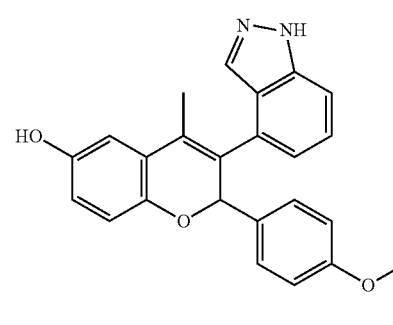
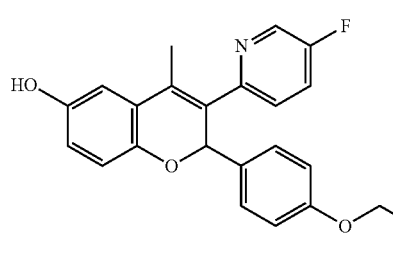
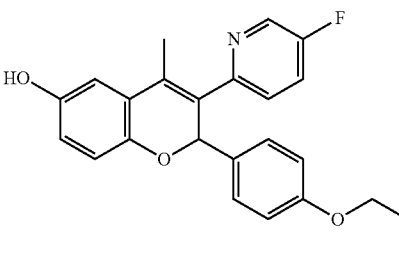
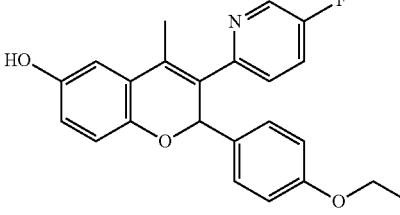

-continued
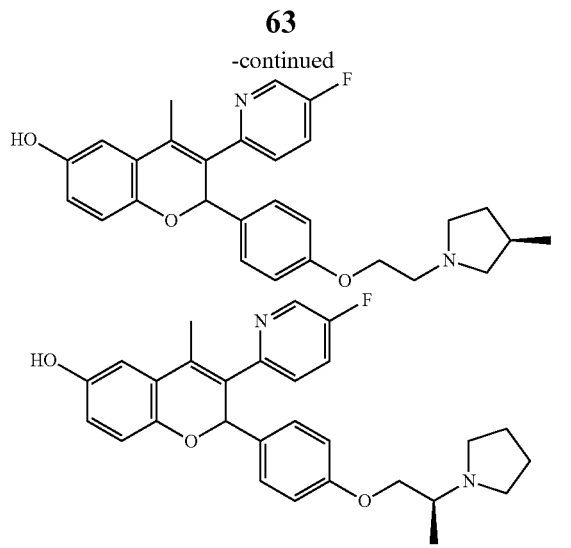
TABLE 1
Exemplary compounds of Formulas (I)-(X)
| Example | Structure | Name | LCMS [M + H]+ |
|---|---|---|---|
| 1 | 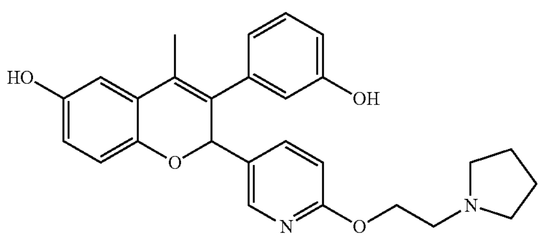 | 3-(3-Hydroxyphenyl)-4-methyl-2-(6-(2-(pyrrolidin-1-yl)ethoxy)pyridin-3-yl)-2H-chromen-6-ol | 445.7 |
| 2 | 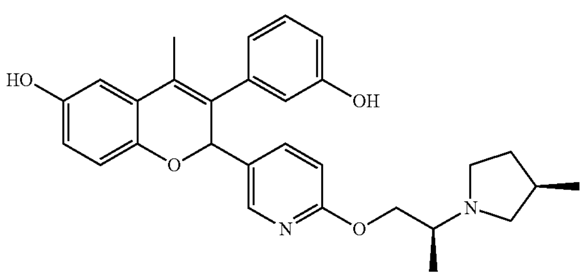 | 3-(3-Hydroxyphenyl)-4-methyl-2-(6-((S)-2-((R)-3-methylpyrrolidin-1-yl)propoxy)pyridin-3-yl)-2H-chromen-6-ol | 473.7 |
| 3 | 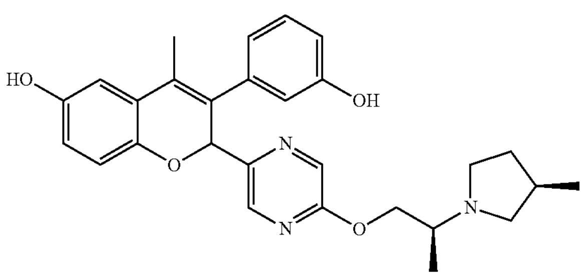 | 3-(3-Hydroxyphenyl)-4-methyl-2-(5-((S)-2-((R)-3-methylpyrrolidin-1-yl)propoxy)pyrazin-2-yl)-2H-chromen-6-ol | 474.7 |

TABLE 1-continued

Exemplary compounds of Formulas (I)-(X)

| Example | Structure | Name | LCMS [M + H]⁺ |
|---|---|---|---|
| 4 | 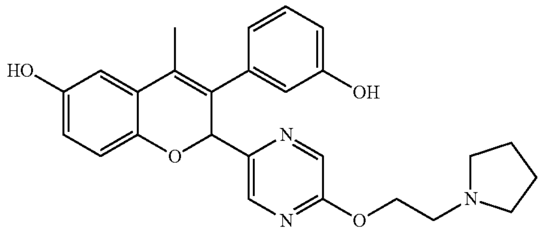 | 3-(3-Hydroxyphenyl)-4-methyl-2-(5-(2-(pyrrolidin-1-yl)ethoxy)pyrazin-2-yl)-2H-chromen-6-ol | 446.7 |
| 5 | 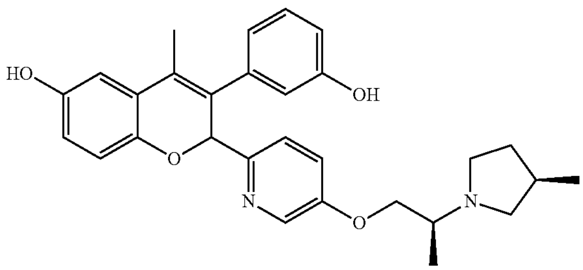 | 3-(3-Hydroxyphenyl)-4-methyl-2-(5-((S)-2-((R)-3-methylpyrrolidin-1-yl)propoxy)pyridin-2-yl)-2H-chromen-6-ol | 473.7 |
| 6 | 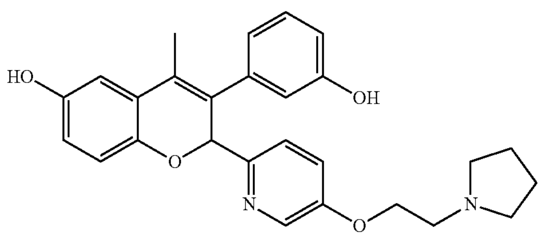 | 3-(3-Hydroxyphenyl)-4-methyl-2-(5-(2-(pyrrolidin-1-yl)ethoxy)pyridin-2-yl)-2H-chromen-6-ol | 445.6 |
| 7 | 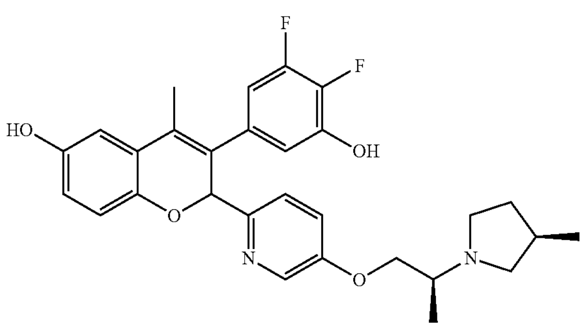 | 3-(3,4-Difluoro-5-hydroxyphenyl)-4-methyl-2-(5-((S)-2-((R)-3-methylpyrrolidin-1-yl)propoxy)pyridin-2-yl)-2H-chromen-6-ol | 509.1 |
| 8 | 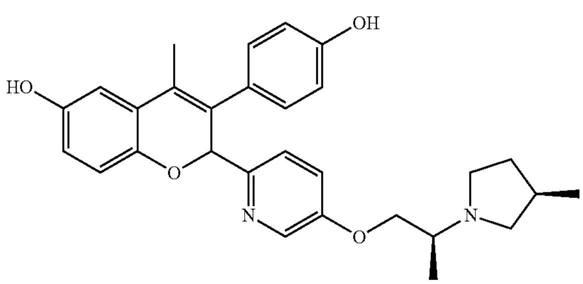 | 3-(4-Hydroxyphenyl)-4-methyl-2-(5-((S)-2-((R)-3-methylpyrrolidin-1-yl)propoxy)pyridin-2-yl)-2H-chromen-6-ol | 473.2 |

TABLE 1-continued

Exemplary compounds of Formulas (I)-(X)

| Example | Structure | Name | LCMS [M + H]+ |
|---|---|---|---|
| 9 | 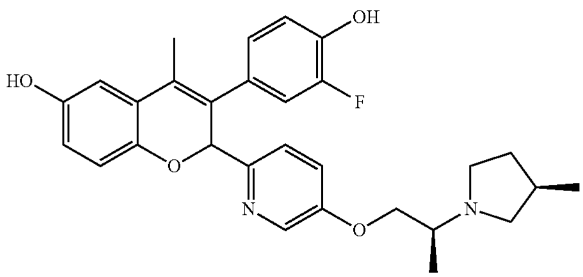 | 3-(3-Fluoro-4-hydroxyphenyl)-4-methyl-2-(5-((S)-2-((R)-3-methylpyrrolidin-1-yl)propoxy)pyridin-2-yl)-2H-chromen-6-ol | 491.1 |
| 10 | 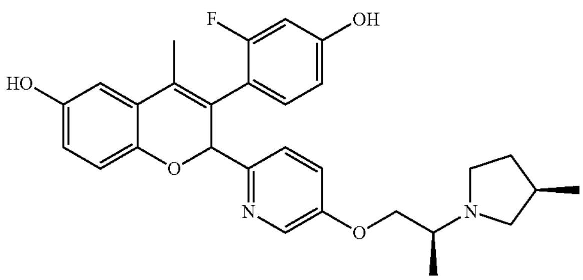 | 3-(2-Fluoro-4-hydroxyphenyl)-4-methyl-2-(5-((S)-2-((R)-3-methylpyrrolidin-1-yl)propoxy)pyridin-2-yl)-2H-chromen-6-ol | 491.1 |
| 11 | 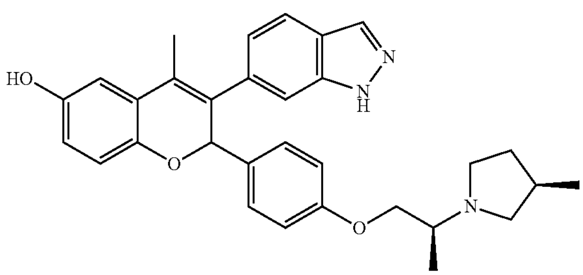 | 3-(1H-Indazol-6-yl)-4-methyl-2-(4-((S)-2-((R)-3-methylpyrrolidin-1-yl)propoxy)phenyl)-2H-chromen-6-ol | 496.1 |
| 12 | 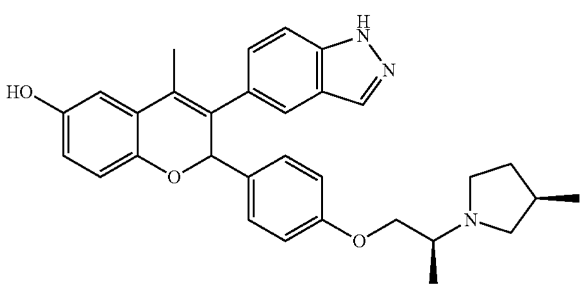 | 3-(1H-Indazol-5-yl)-4-methyl-2-(4-((S)-2-((R)-3-methylpyrrolidin-1-yl)propoxy)phenyl)-2H-chromen-6-ol | 496.1 |
| 13 | 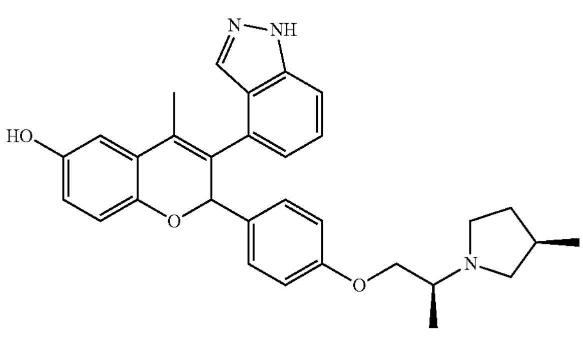 | 3-(1H-Indazol-4-yl)-4-methyl-2-(4-((S)-2-((R)-3-methylpyrrolidin-1-yl)propoxy)phenyl)-2H-chromen-6-ol | 496.2 |

TABLE 1-continued

Exemplary compounds of Formulas (I)-(X)

| Example | Structure | Name | LCMS [M + H]⁺ |
|---|---|---|---|
| 14 | 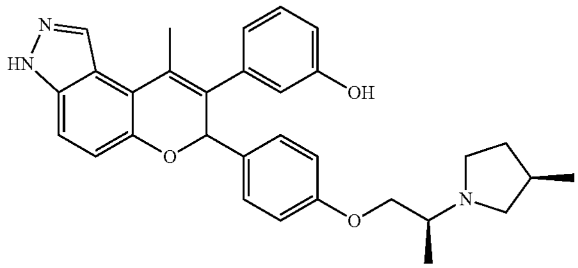 | 3-(9-Methyl-7-(4-((S)-2-((R)-3-methylpyrrolidin-1-yl)propoxy)phenyl)-3,7-dihydropyrano[3,2-e]indazol-8-yl)phenol | 496.0 |
| 15 | 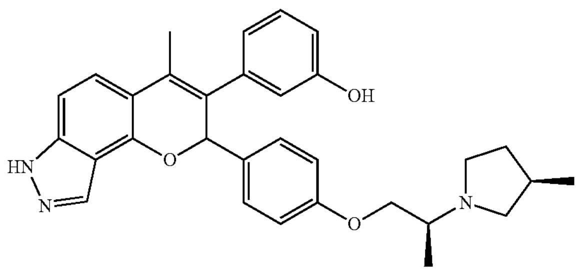 | 3-(4-Methyl-2-(4-((S)-2-((R)-3-methylpyrrolidin-1-yl)propoxy)phenyl)-2,7-dihydropyrano[2,3-e]indazol-3-yl)phenol | 496.1 |
| 16 | 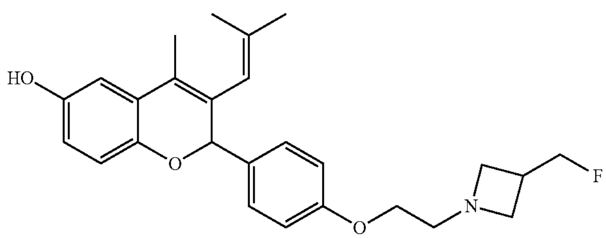 | 2-[4-[2-[3-(Fluoromethyl)azetidin-1-yl]ethoxy]phenyl]-4-methyl-3-(2-methylprop-1-enyl)-2H-chromen-6-ol | 424.3 |
| 17 | 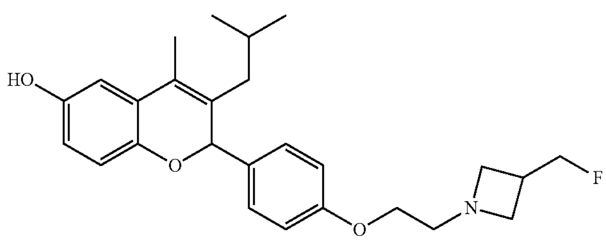 | 2-(4-(2-(3-(Fluoromethyl)azetidin-1-yl)ethoxy)phenyl)-3-isobutyl-4-methyl-2H-chromen-6-ol | 448.3 |
| 18 | 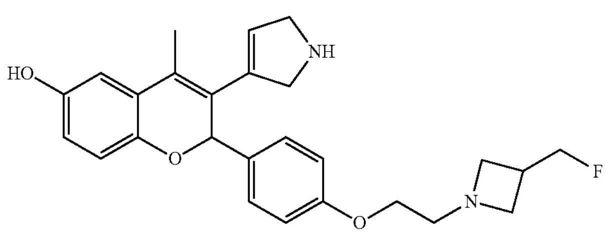 | 3-(2,5-dihydro-1H-pyrrol-3-yl)-2-(4-(2-(3-(fluoromethyl)azetidin-1-yl)ethoxy)phenyl)-4-methyl-2H-chromen-6-ol | 434.3 |
| 19 | 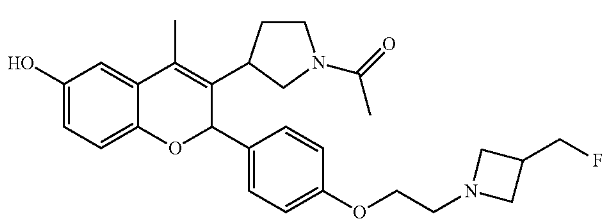 | 1-(3-(2-(4-(2-(3-(Fluoromethyl)azetidin-1-yl)ethoxy)phenyl)-6-hydroxy-4-methyl-2H-chromen-3-yl)pyrrolidin-1-yl)ethanone | 481.3 |

TABLE 1-continued

Exemplary compounds of Formulas (I)-(X)

| Example | Structure | Name | LCMS [M + H]+ |
|---|---|---|---|
| 20 | 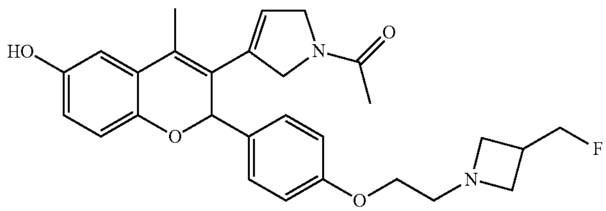 | 1-(3-(2-(4-(2-(3-(Fluoromethyl)azetidin-1-yl)ethoxy)phenyl)-6-hydroxy-4-methyl-2H-chromen-3-yl)-2,5-dihydro-1H-pyrrol-1-yl)ethanone | 479.3 |
| 21 | 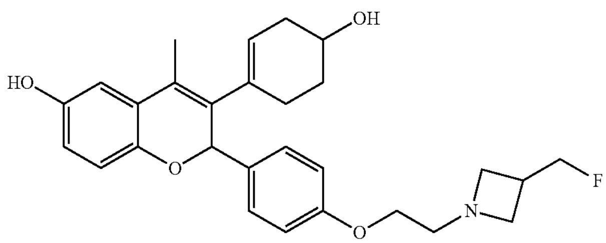 | 2-(4-(2-(3-(Fluoromethyl)azetidin-1-yl)ethoxy)phenyl)-3-(4-hydroxycyclohex-1-en-1-yl)-4-methyl-2H-chromen-6-ol | 466.3 |
| 22 | 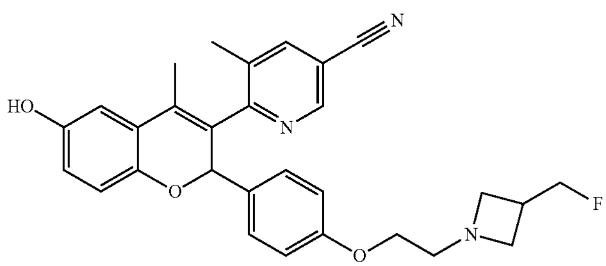 | 2-{4-[2-(3-Fluoromethyl-azetidin-1-yl)-ethoxy]-phenyl}-4-methyl-3-(3-methyl-5-cyano-pyridin-2-yl)-2H-chromen-6-ol | 486.2 |
| 23 | 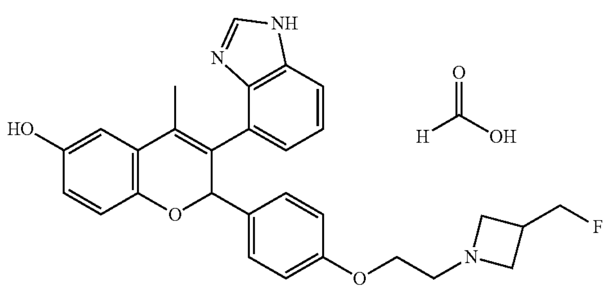 | 3-(1H-benzo[d]imidazol-4-yl)-2-(4-(2-(3-(fluoromethyl)azetidin-1-yl)ethoxy)phenyl)-4-methyl-2H-chromen-6-ol formate | 486.3 |
| 24 | 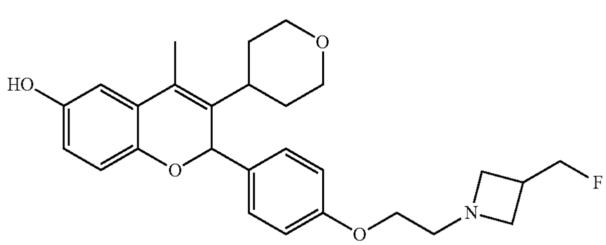 | 2-(4-(2-(3-(fluoromethyl)azetidin-1-yl)ethoxy)phenyl)-4-methyl-3-(tetrahydro-2H-pyran-4-yl)-2H-chromen-6-ol | 454.1 |
| 25 | 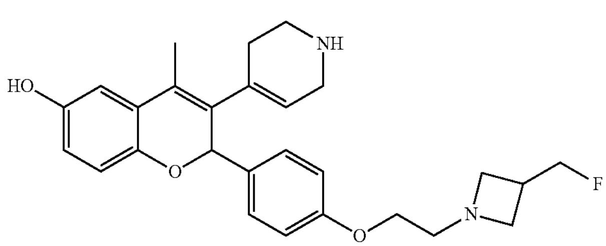 | 2-(4-(2-(3-(fluoromethyl)azetidin-1-yl)ethoxy)phenyl)-4-methyl-3-(1,2,3,6-tetrahydropyridin-4-yl)-2H-chromen-6-ol | 451.4 |

TABLE 1-continued

Exemplary compounds of Formulas (I)-(X)

| Example | Structure | Name | LCMS [M + H]+ |
|---|---|---|---|
| 26 | 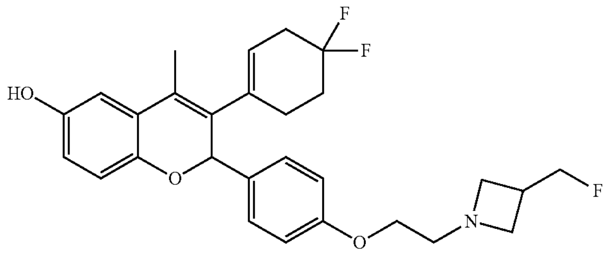 | 3-(4,4-difluorocyclohex-1-en-1-yl)-2-(4-(2-(3-(fluoromethyl)azetidin-1-yl)ethoxy)phenyl)-4-methyl-2H-chromen-6-ol | 486.3 |
| 27 | 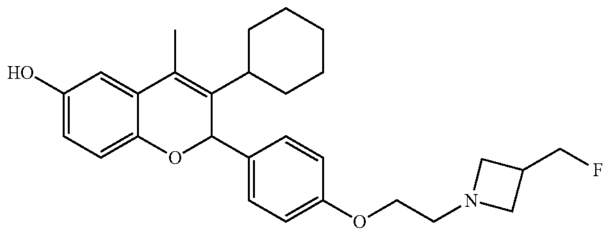 | 3-cyclohexyl-2-(4-(2-(3-(fluoromethyl)azetidin-1-yl)ethoxy)phenyl)-4-methyl-2H-chromen-6-ol | 452.1 |
| 28 | 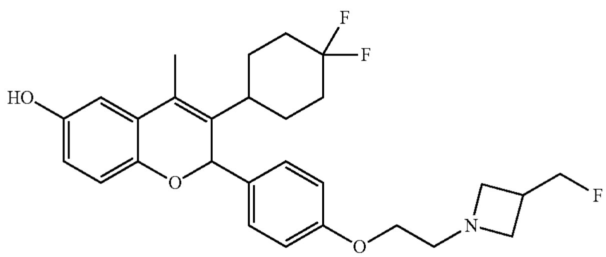 | 3-(4,4-difluorocyclohexyl)-2-(4-(2-(3 (fluoromethyl)azetidin-1-yl)ethoxy)phenyl)-4-methyl-2H-chromen-6-ol | 488.3 |
| 29 | 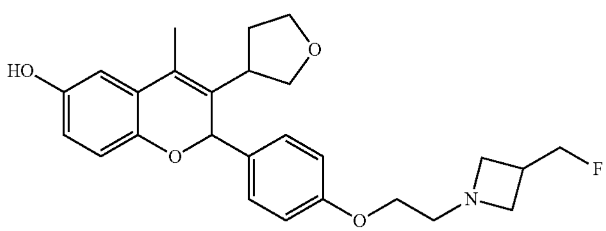 | 2-(4-(2-(3-(fluoromethyl)azetidin-1-yl)ethoxy)phenyl)-4-methyl-3-(tetrahydrofuran-3-yl)-2H-chromen-6-ol | 440.3 |
| 30 | 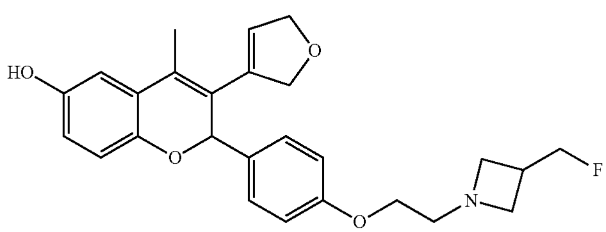 | 3-(2,5-dihydrofuran-3-yl)-2-(4-(2-(3-(fluoromethyl)azetidin-1-yl)ethoxy)phenyl)-4-methyl-2H-chromen-6-ol | 438.1 |
| 31 | 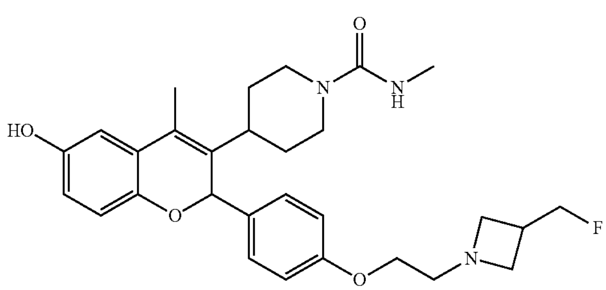 | 4-(2-(4-(2-(3-(fluoromethyl)azetidin-1-yl)ethoxy)phenyl)-6-hydroxy-4-methyl-2H-chromen-3-yl)-N-methylpiperidine-1-carboxamide | 510.4 |

TABLE 1-continued

Exemplary compounds of Formulas (I)-(X)

| Example | Structure | Name | LCMS [M + H]+ |
|---|---|---|---|
| 32 | 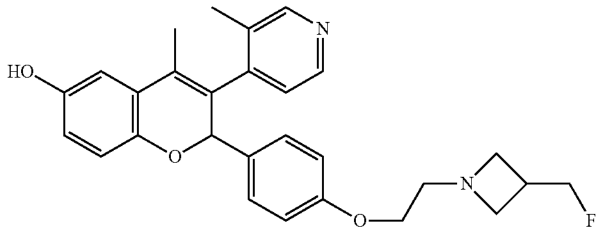 | 2-{4-[2-(3-Fluoromethyl-azetidin-1-yl)-ethoxy]-phenyl}-4-methyl-3-(3-methyl-pyridin-4-yl)-2H-chromen-6-ol | 461.2 |
| 33 | 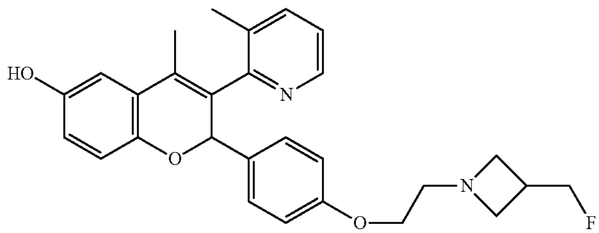 | 2-{4-[2-(3-Fluoromethyl-azetidin-1-yl)-ethoxy]-phenyl}-4-methyl-3-(3-methyl-pyridin-2-yl)-2H-chromen-6-ol | 461.2 |
| 34 | 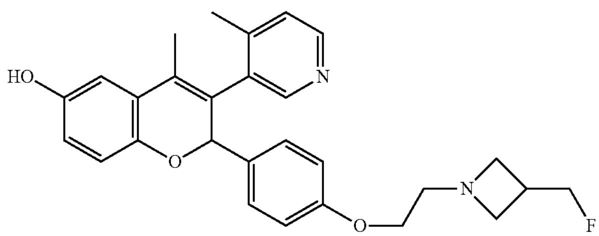 | 2-{4-[2-(3-Fluoromethyl-azetidin-1-yl)-ethoxy]-phenyl}-4-methyl-3-(4-methyl-pyridin-3-yl)-2H-chromen-6-ol | 461.2 |
| 35 | 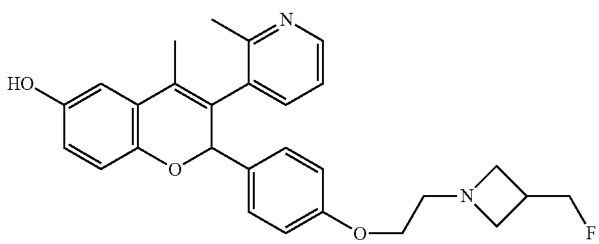 | 2-{4-[2-(3-Fluoromethyl-azetidin-1-yl)-ethoxy]-phenyl}-4-methyl-3-(2-methyl-pyridin-3-yl)-2H-chromen-6-ol | 461.2 |
| 36 | 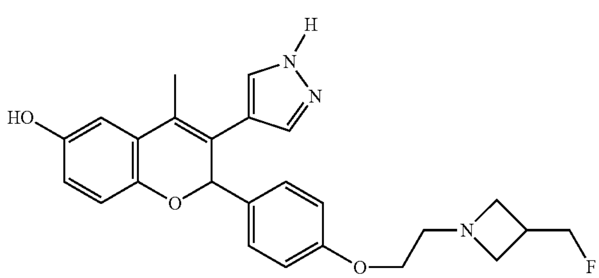 | 2-{4-[2-(3-Fluoromethyl-azetidin-1-yl)-ethoxy]-phenyl}-4-methyl-3-(1H-pyrazol-4-yl)-2H-chromen-6-ol | 436.3 |
| 37 | 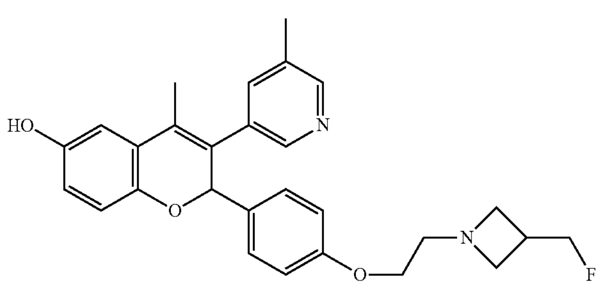 | 2-{4-[2-(3-Fluoromethyl-azetidin-1-yl)-ethoxy]-phenyl}-4-methyl-3-(5-methyl-pyridin-3-yl)-2H-chromen-6-ol | 464.2 |

TABLE 1-continued

Exemplary compounds of Formulas (I)-(X)

| Example | Structure | Name | LCMS [M + H]+ |
|---|---|---|---|
| 38 | 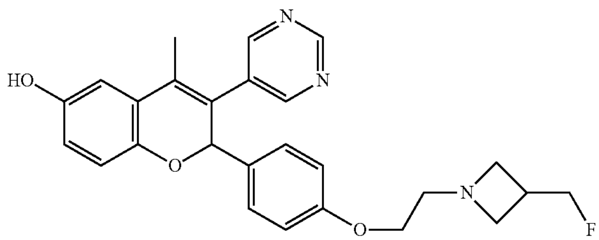 | 2-{4-[2-(3-Fluoromethyl-azetidin-1-yl)-ethoxy]-phenyl}-4-methyl-3-pyrimidin-5-yl-2H-chromen-6-ol | 448.3 |
| 39 | 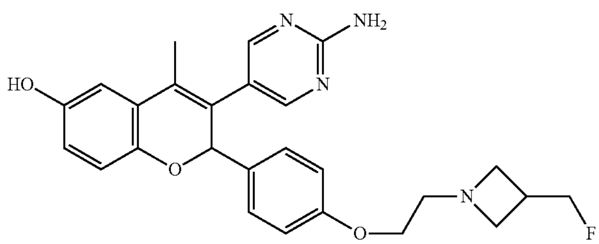 | 3-(2-Amino-pyrimidin-5-yl)-2-{4-[2-(3-fluoromethyl-azetidin-1-yl)-ethoxy]-phenyl}-4-methyl-2H-chromen-6-ol | 463.2 |
| 40 | 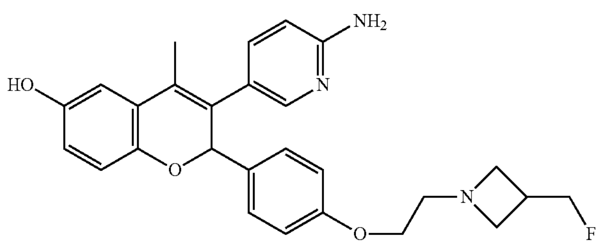 | 3-(6-Amino-pyridin-3-yl)-2-{4-[2-(3-fluoromethyl-azetidin-1-yl)-ethoxy]-phenyl}-4-methyl-2H-chromen-6-ol | 462.2 |
| 41 | 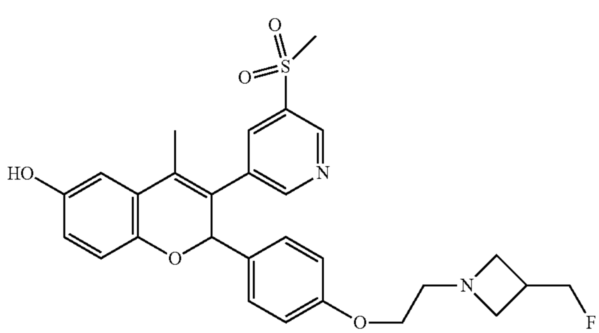 | 2-{4-[2-(3-Fluoromethyl-azetidin-1-yl)-ethoxy]-phenyl}-3-(5-methanesulfonyl-pyridin-3-yl)-4-methyl-2H-chromen-6-ol | 525.2 |
| 42 | 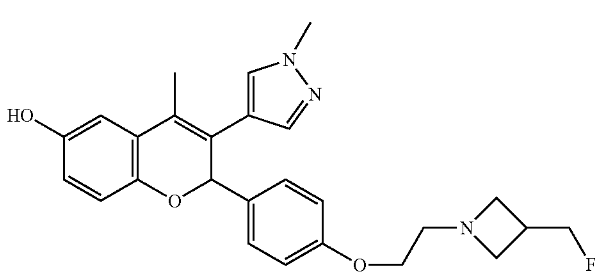 | 2-{4-[2-(3-Fluoromethyl-azetidin-1-yl)-ethoxy]-phenyl}-4-methyl-3-(1-methyl-1H-pyrazol-4-yl)-2H-chromen-6-ol | 450.2 |

TABLE 1-continued

Exemplary compounds of Formulas (I)-(X)

| Example | Structure | Name | LCMS [M + H]⁺ |
|---|---|---|---|
| 43 | 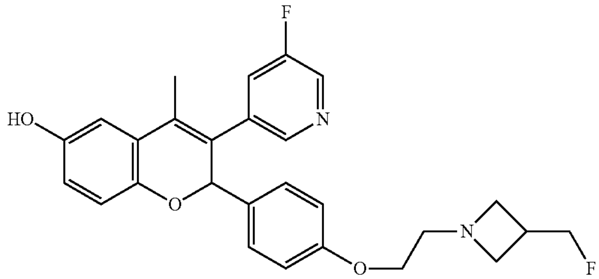 | 2-{4-[2-(3-Fluoromethyl-azetidin-1-yl)-ethoxy]-phenyl}-3-(5-fluoro-pyridin-3-yl)-4-methyl-2H-chromen-6-ol | 465.2 |
| 44 | 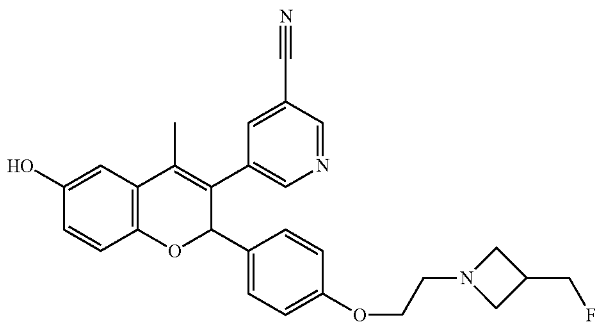 | 5-(2-{4-[2-(3-Fluoromethyl-azetidin-1-yl)-ethoxy]-phenyl}-6-hydroxy-4-methyl-2H-chromen-3-yl)-nicotinonitrile | 472.2 |
| 45 | 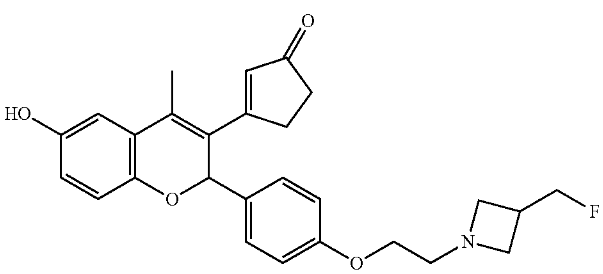 | 3-[2-[4-[2-[3-(fluoromethyl)azetidin-1-yl]ethoxy]phenyl]-6-hydroxy-4-methyl-2H-chromen-3-yl]cyclopent-2-en-1-one | 450.2 |
| 46 | 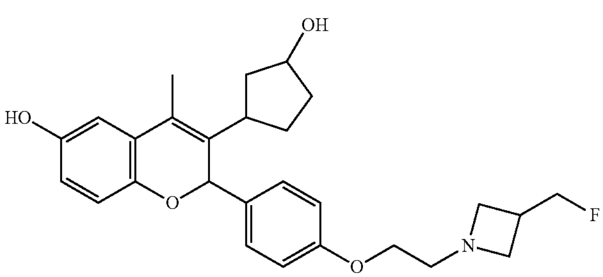 | 2-[4-[2-[3-(fluoromethyl)azetidin-1-yl]ethoxy]phenyl]-3-(3-hydroxycyclopentyl)-4-methyl-2H-chromen-6-ol | 454.2 |
| 47 | 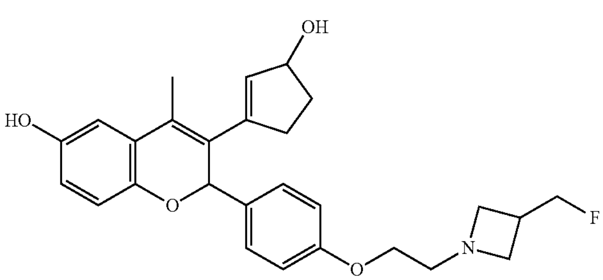 | 2-[4-[2-[3-(fluoromethyl)azetidin-1-yl]ethoxy]phenyl]-3-(3-hydroxycyclopenten-1-yl)-4-methyl-2H-chromen-6-ol | 452.2 |

TABLE 1-continued

Exemplary compounds of Formulas (I)-(X)

| Example | Structure | Name | LCMS [M + H]+ |
|---|---|---|---|
| 48 | 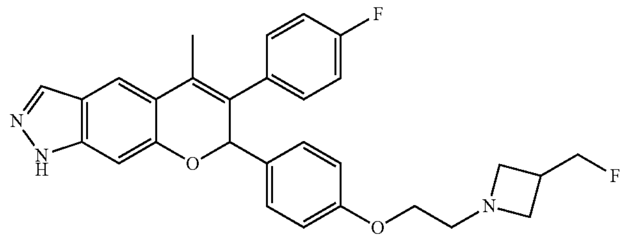 | 7-[4-[2-[3-(fluoromethyl)azetidin-1-yl]ethoxy]phenyl]-6-(4-fluorophenyl)-5-methyl-1,7-dihydropyrano[3,2-f]indazole | 448.2 |
| 49 | 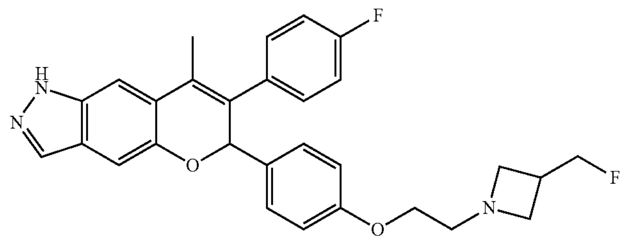 | 6-[4-[2-[3-(fluoromethyl)azetidin-1-yl]ethoxy]phenyl]-7-(4-fluorophenyl)-8-methyl-1,6-dihydropyrano[2,3-f]indazole | 448.2 |
| 50 | 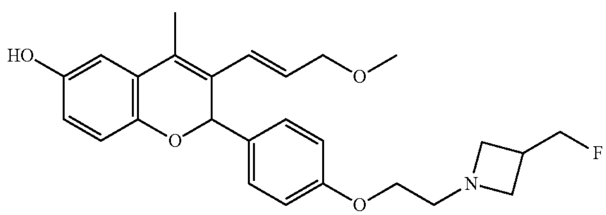 | 2-[4-[2-[3-(fluoromethyl)azetidin-1-yl]ethoxy]phenyl]-3-[(E)-3-methoxyprop-1-enyl]-4-methyl-2H-chromen-6-ol | 440.2 |
| 51 | 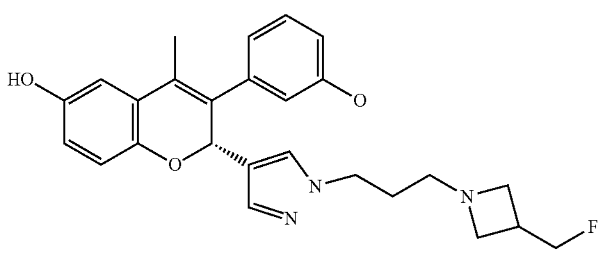 | (R)-2-(1-(3-(3-(fluoromethyl)azetidin-1-yl)propyl)-1H-pyrazol-4-yl)-3-(3-hydroxyphenyl)-4-methyl-2H-chromen-6-ol | 450.2 |
| 52 | 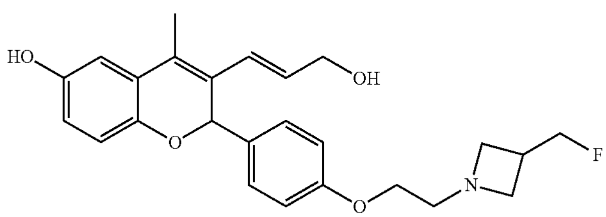 | 2-[4-[2-[3-(fluoromethyl)azetidin-1-yl]ethoxy]phenyl]-3-[(E)-3-hydroxyprop-1-enyl]-4-methyl-2H-chromen-6-ol | 426.2 |

Synthesis of Compounds

Compounds of Formulas (I)-(X) described herein are synthesized using standard synthetic techniques or using methods known in the art in combination with methods described herein. In additions, solvents, temperatures and other reaction conditions presented herein may vary.

The starting material used for the synthesis of the compounds of Formulas (I)-(X) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In some embodiments, the compounds of Formulas (I)-(X) are prepared using techniques and procedures as described in any one of the following in combination with techniques and procedures described above: U.S. Pat. No.

8,703,810, US 2013-0137746, US 2013-0231333, WO 2013/090829, WO 2013/142266, WO 2013/090836.

In some embodiments, compounds described herein are prepared as described in the Examples.

In one aspect, compounds described herein exist as a racemic mixture or in enantiomerically enriched or enantiomerically pure form. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In certain embodiments, compounds described herein are prepared as their individual stereoisomers by enzymatic resolution. In some embodiments, resolution of individual stereoisomers is carried out using a lipase or an esterase. In some embodiments, resolution of individual stereoisomers is carried out by lipase or esterase-catalyzed asymmetric deacylation. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

Reference to a use of a compound or a composition that includes a compound refers to any optical purity of a compound of Formulas (I)-(X) in the composition, including but not limited to optically pure compound.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In some embodiments, the active entity is a phenolic compound as described herein (e.g. compound of Formulas (I)-(X)). A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, one or both hydroxyl groups in the compounds disclosed herein is used to form a prodrug, wherein the hydroxyl group(s) is/are incorporated into an alkyl ester.

Prodrug forms of the herein described compounds, wherein the prodrug is metabolized in vivo to produce a compound of Formulas (I)-(X) as set forth herein are included within the scope of the claims. In some cases, some of the herein-described compounds may be a prodrug for another derivative or active compound.

In some embodiments, sites on the aromatic ring portion of compounds of Formulas (I)-(X) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms that are present in the compounds described herein is replaced with one or more deuterium atoms.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formulas (I)-(X) with acids. Pharmaceutically acceptable salts are also obtained by reacting a compound of Formulas (I)-(X) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, a and the like; or with an organic acid to form a salt, such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, a ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, a potassium salt), an alkaline earth ion (e.g. magnesium, or calcium), or an aluminum ion e.g. an aluminum salt). In some cases, compounds described herein are prepared as a hydrochloride salt. In some other cases, compounds described herein are prepared as a mandelate salt. In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In some embodiments, compounds described herein are prepared are hydrates.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formulas (I)-(X), or a pharmaceutically acceptable salt thereof, and at least one pharmaceutically acceptable inactive ingredient. In some embodiments, the compounds described herein are administered as pharmaceutical compositions in which a compound of Formulas (I)-(X), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formulas (I)-(X), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formulas (I)-(X), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formulas (I)-(X), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formulas (I)-(X), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral dosage forms are prepared by mixing a compound of Formulas (I)-(X), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formulas (I)-(X), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formulas (I)-(X), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formulas (I)-(X), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed (U.S. Pat. Nos. 5,011,692; 5,017,381; 5,229,135; 540,329; 5,837,284). In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formulas (I)-(X), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formulas (I)-(X), or a pharmaceutically acceptable salt or solvate thereof, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formulas (I)-(X), or a pharmaceutically acceptable salt thereof, are administered using a variety of formulations known in the art. For example, such formulations include, but are not limited to, U.S. Pat. Nos. 4,229,447; 4,596,795; 4,755,386; 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formulas (I)-(X), or a pharmaceutically acceptable salt thereof, are prepared as transdermal dosage forms. In one embodiment, the transdermal formulations described herein include at least three components: (1) a formulation of a compound of Formulas (I)-(X), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formulas (I)-(X), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Compounds disclosed herein are estrogen receptor modulators. In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formulas (I)-(X).

Also described are pharmaceutical compositions comprising a therapeutically effective amount of a compound of Formulas (I)-(X). In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors. In some embodiments, the pharmaceutical composition comprises one or more anti-cancer agents.

In some embodiments, provided herein is a method comprising administering a compound of Formulas (I)-(X), or a pharmaceutically acceptable salt, solvate, or prodrug thereof, to a human with a diseases or condition that is estrogen sensitive, estrogen receptor meditated or estrogen receptor dependent. In some embodiments, the human is already being administered one or more additional therapeutically active agents other than a compound of Formulas (I)-(X), or a pharmaceutically acceptable salt, solvate, or prodrug thereof. In some embodiments, the method further comprises administering one or more additional therapeutically active agents other than a compound of Formulas (I)-(X), or a pharmaceutically acceptable salt, solvate, or prodrug thereof.

In some embodiments, the one or more additional therapeutically active agents other than a compound of Formulas (I)-(X), or a pharmaceutically acceptable salt, solvate, or prodrug thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects. In some embodiments, the estrogen receptor dependent or estrogen receptor mediated disease or condition is bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, or infertility.

Some embodiments provided herein describe a method of treating cancer in a mammal, wherein the method comprises administering to the mammal a therapeutically effective amount of a compound of Formulas (I)-(X), or a pharmaceutically acceptable salt thereof. In some embodiments, the cancer is breast cancer, lung cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the anti-hormonal treatment includes treatment with at least one agent selected from tamoxifen, fulvestrant, steroidal aromatase inhibitors, and non-steroidal aromatase inhibitors.

Also described herein, in some embodiments, are methods of treating hormone receptor positive metastatic breast cancer in a postmenopausal woman with disease progression following anti-estrogen therapy comprising administering to the woman an estrogen receptor degrading compound of Formulas (I)-(X). In some embodiments, the compound is an estrogen receptor degrader; is an estrogen receptor antagonist; has minimal or negligible estrogen receptor agonist activity; or combinations thereof.

Some embodiments provided herein describe a method of treating a hormonal dependent benign or malignant disease of the breast or reproductive tract in a mammal comprising administering to the mammal an effective amount of a compound of Formulas (I)-(X). In some embodiments, the benign or malignant disease is breast cancer. In some embodiments, the method further comprises administering to the mammal radiation therapy. In some embodiments, the compound is administered prior to or following surgery. In some embodiments, the method further comprises administering to the mammal at least one additional anti-cancer agent.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formulas (I)-(X), or a pharmaceutically acceptable salt, solvate, or prodrug thereof, are administered orally, systemically, intravenously, subcutaneously, or topically.

In another aspect is the use of a compound of Formulas (I)-(X), or a pharmaceutically acceptable salt, solvate, or prodrug thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound of Formulas (I)-(X), or a pharmaceutically acceptable salt, solvate, or prodrug thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal at least one compound having the structure of Formulas (I)-(X), or a pharmaceutically acceptable salt thereof. In some embodiments, the method comprises reducing ER activation in breast cells, lung cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound of Formulas (I)-(X), or a pharmaceutically acceptable salt thereof, in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a noncancerous disease or condition of the uterus.

In one aspect is the use of a compound of Formulas (I)-(X), or a pharmaceutically acceptable salt, solvate, or prodrug thereof, in the manufacture of a medicament for the treatment of diseases or conditions that are estrogen sensitive, estrogen receptor dependent or estrogen receptor mediated. In some embodiments, the disease or condition is breast cancer, lung cancer, ovarian cancer, colon cancer, prostate cancer, endometrial cancer, or uterine cancer. In some embodiments, the disease or condition is described herein.

In some cases disclosed herein is the use of a compound of Formulas (I)-(X), or a pharmaceutically acceptable salt thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formulas (I)-(X), or pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Methods of Dosing and Treatment Regimens

In one embodiment, the compounds of Formulas (I)-(X), or a pharmaceutically acceptable salt thereof, are used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formulas (I)-(X), or a pharmaceutically acceptable salt thereof, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formulas (I)-(X), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In some embodiments, the daily dosages appropriate for a compound of Formulas (I)-(X), or a pharmaceutically acceptable salt thereof, described herein are administered once a day, twice a day, or three times a day.

In one embodiment, the daily dosages appropriate for the compound of Formulas (I)-(X), or a pharmaceutically acceptable salt thereof, described herein are from about 0.01 to about 10 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, CA-125 blood levels are monitored in humans that are administered (or considered as candidates for treatment with) a compound of Formulas (I)-(X), or a pharmaceutically acceptable salt thereof. CA-125 (also known as mucin-16) is a glycoprotein in humans. In some embodiments, CA-125 levels are elevated in the blood of patients with certain type of cancers. In some embodiments, CA-125 is used as a serum biomarker in patients with certain type of cancers. In some embodiments, the certain types of cancers include, but are not limited to, breast cancer, ovarian cancer, endometrial (uterine) cancer, prostate cancer, and lung cancer. In some embodiments, monitoring CA-125 levels in the blood is used to determine the tumor burden in a human. In some embodiments, monitoring CA-125 levels in the blood is used to determine when to give a human anti-cancer therapy (e.g. a compound of Formulas (I)-(X), or a pharmaceutically acceptable salt thereof). In some embodiments, monitoring CA-125 levels in the blood is used to determine how a human is responding to anti-cancer therapy (e.g. a compound of Formulas (I)-(X), or a pharmaceutically acceptable salt thereof). In some embodiments, CA-125 is used as a biomarker for the diagnosis and management of ovarian cancer. Rising levels of CA-125 after radiation therapy or surgery with no detectable metastases could indicate recurrent ovarian cancer and the need to start anti-cancer treatment.

Combination Treatments

In certain instances, it is appropriate to administer at least one compound of Formulas (I)-(X), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formulas (I)-(X), or a pharmaceutically acceptable salt thereof, is co-administered with a second therapeutic agent, wherein the compound of Formulas (I)-(X), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formulas (I)-(X), or a pharmaceutically acceptable salt thereof, is initiated prior to, during, or after treatment with a second agent described herein, and continues until any time during treatment with the second agent or after termination of treatment with the second agent. It also includes treatments in which a compound of Formulas (I)-(X), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formulas (I)-(X), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agents for Use in Combination Therapy

In some embodiments, methods for treatment of estrogen receptor-dependent or estrogen receptor-mediated conditions or diseases, such as proliferative disorders, including cancer, comprises administration to a mammal a compound of Formulas (I)-(X), or a pharmaceutically acceptable salt thereof, in combination with at least one additional therapeutic agent.

In some embodiments, a compound of Formulas (I)-(X) or a pharmaceutically acceptable salt thereof, is used in combination with one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, modulators of the immune system, PD-1 inhibitors, poly ADP-ribose polymerase (PARP) inhibitors, and aromatase inhibitors.

In certain instances, it is appropriate to administer at least one compound of Formulas (I)-(X), or a pharmaceutically acceptable salt thereof, in combination with one or more other therapeutic agents. In certain embodiments, the one or more other therapeutic agents is an anti-cancer agent(s).

In some embodiments, a compound of Formulas (I)-(X), or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a compound of Formulas (I)-(X), or a pharmaceutically acceptable salt thereof, in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

Monoclonal antibodies include, but are not limited to, trastuzumab (Herceptin).

In some embodiments, a compound of Formulas (I)-(X), or a pharmaceutically acceptable salt thereof, is used in combination with at least one additional therapeutic agent selected from: abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; AZD6244; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; bosutinib; brequinar sodium; bropirimine; busulfan; cabozantinib; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dinaciclib; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; ENMD-2076; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; foretinib; fosquidone; fostriecin sodium; fulvestrant; gefitinib; gemcitabine; gemcitabine hydrochloride; gemcitabine-cisplatin; gemtuzumab ozogamicin; goserelin acetate; GSK1120212; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; ipropla- tin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; MM-121;

mycophenolic acid; nandrolone phenpropionate; nelarabine; nilotinib; nocodazoie; nofetumomab; nogalamycin; ofatumumab; onartuzumab; oprelvekin; ormaplatin; oxaliplatin; oxisuran; paclitaxel; palbociclib (PD-0332991); palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; saracatinib; sargramostim; seliciclib; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; TAK-733; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; U3-1287; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; or zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formulas (I)-(X), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formulas (I)-(X), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with the compounds of Formulas (I)-(X), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole. In some embodiments, the aromatase inhibitor is anastrozole, letrozole or exemestane.

In some embodiments, a compound of Formulas (I)-(X), or a pharmaceutically acceptable salt thereof, is administered in combination with a CDK 4/6 inhibitor. In some embodiments, the CDK 4/6 inhibitor is palbociclib (PD-0332991), LEE011 or LY283519. In some embodiments, the CDK 4/6 inhibitor is LEE011. In some embodiments, LEE011 is administered at a dose of about 10 mg per day to about 1000 mg per day. In some embodiments, LEE011 is administered at a dose of about 400 mg per day, about 500 mg per day or about 600 mg per day. In some embodiments, the daily dose of LEE011 is orally administered. In some embodiments, the daily dose of LEE011 is orally administered once a day for three weeks followed by a one week drug holiday where LEE011 is not administered.

In some embodiments, a compound of Formulas (I)-(X), or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235, BYL719, GDC0032, BKM120, BGT226, GDC0068, GDC-0980, GDC0941, INK128 (MLN0128), INK1117, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, CU-906, AZD-2014 or CUDC-907. In some embodiments, the phosphoinositide 3-kinase (PI3K)/mTOR pathway inhibitor is everolimus. In some embodiments, everolimus is administered at a dose of about 1 mg per day to about 20 mg per day. In some embodiments, everolimus is administered at a dose of about 2.5 mg per day, about 5 mg per day, or about 10 mg per day. In some embodiments, the daily dose of everolimus is administered once a day. In some embodiments, the phosphoinositide 3-kinase (PI3K)/mTOR pathway inhibitor is BKM120. In some embodiments, BKM120 is administered at a dose of about 5 mg per day to about 500 mg per day. In some embodiments, BKM120 is administered at a dose of about 50 mg per day to about 100 mg per day. In some embodiments, BKM120 is administered at a dose of about 100 mg per day. In some embodiments, the daily dose of BKM120 is administered once a day. In some embodiments, the phosphoinositide 3-kinase (PI3K)/mTOR pathway inhibitor is BYL719. In some embodiments, BYL719 is administered at a dose of about 25 mg per day to about 1000 mg per day. In some embodiments, BYL719 is administered at a dose of about 250 mg per day or about 350 mg per day. In some embodiments, the daily dose of BYL719 is administered once a day.

In some embodiments, a compound of Formulas (I)-(X), or a pharmaceutically acceptable salt thereof, is administered in combination with a histone deacetylase inhibitor (HDAC). In some embodiments, the HDAC inhibitor is entinostat, vorinostat (SAHA), panobinostat or mocetinostat. In some embodiments, the HDAC inhibitor is entinostat. In some embodiments, entinostat is administered at a dose of about 0.1 mg per day to about 100 mg per day. In some embodiments, entinostat is administered at a dose of about 4 mg per day to about 15 mg per day. In some embodiments, entinostat is administered orally on days 1 and 15 of a 28 day cycle. In some embodiments, entinostat is administered orally weekly for 3 weeks followed by a 1-week break in a 4-week cycle. In some embodiments, entinostat is administered orally on days 3 and 10 of a 28 day cycle. In some embodiments, entinostat is administered once daily on days 1, 8, 15, 22, and 29. In some embodiments, 10 mg or 15 mg of entinostat is administered every other week or 15 mg on days 1, 8, and 15 every 28 days. In some embodiments, entinostat is orally administered on day 1 and day 8 at a dose of between 4 mg to 8 mg. In some embodiments, 5 mg of entinostat is orally administered once weekly.

In some embodiments, a compound of Formulas (I)-(X), or a pharmaceutically acceptable salt thereof, is administered in combination with a HER-2 inhibitor. In some embodiments, the HER-2 inhibitor is trastuzumab, pertuzumab or TDM-1.

In some embodiments, a compound of Formulas (I)-(X), or a pharmaceutically acceptable salt thereof, is administered in combination with an epidermal growth factor receptor (EGFR) inhibitor. In some embodiments, the EGFR inhibitor is lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, AP-26113, MEHD7945A or CO-1686.

In some embodiments, a compound of Formulas (I)-(X), or a pharmaceutically acceptable salt thereof, is administered in combination with an anti-angiogenesis agent. In some embodiments, the anti-angiogenesis agent is a VEGFR inhibitor. In some embodiments, the anti-angiogenesis agent is a multi-kinase targeting agent. In some embodiments, the anti-angiogenesis agent is bevacizumab, ABR-215050 (tasquinimod), CHIR-258 (dovitinib), EXEL-7647, OSI-930, BIBF-1120, BAY-73-4506, BMS-582664 (brivanib), RO-4929097, JNJ-26483327, AZD-2171 (cediranib), sorafenib, aflibercept, enzastaurin, AG-013736 (axitinib), GSK-786034 (pazopanib), AP-23573, or sunitinib.

In some embodiments, a compound of Formulas (I)-(X), or a pharmaceutically acceptable salt thereof, is administered in combination with an anti-PD-1 agent. In some embodiments, the anti-PD-1 agent is MK-3475, Nivolumab, MPDL3280A, or MEDI4736.

In some embodiments, a compound of Formulas (I)-(X), or a pharmaceutically acceptable salt thereof, is administered in combination with an AKT inhibitor. In some embodiments, the AKT inhibitor is GDC0068, MK-2206, AT7867, GSK2110183, GSK2141795, AZD5363 or GSK690693.

In some embodiments, a compound of Formulas (I)-(X), or a pharmaceutically acceptable salt thereof, is administered in combination with an IGFR inhibitor. In some embodiments, the IGFR inhibitor is cixutumumab, dalotuzumab, BMS-754807, or MEDI-573

In some embodiments, a compound of Formulas (I)-(X), or a pharmaceutically acceptable salt thereof, is administered in combination with an FGFR inhibitor. In some embodiments, the FGFR inhibitor is CHIR-258 (dovitinib), E-3810, or AZD4547.

In some embodiments, a compound of Formulas (I)-(X), or a pharmaceutically acceptable salt thereof, is administered in combination with doxorubicin, cyclophosphamide, capecitabine, vinorelbine, paclitaxel, doxetaxel, or cisplatin.

Yet other anticancer agents for use in combination with the compounds of Formulas (I)-(X), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formulas (I)-(X), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formulas (I)-(X), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.).

In some embodiments, compounds of Formulas (I)-(X), or a pharmaceutically acceptable salt thereof, are used to treat cancer in combination with: a second antiestrogen (e.g., tamoxifen), an antiandrogen (e.g., bicalutamide, flutamide, enzalutamide, JNJ56021927/ARN-509), a gonadotropin releasing hormone analog (e.g., leuprolide).

Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Iso-eleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formulas (I)-(X), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formulas (I)-(X), or a pharmaceutically acceptable salt thereof, is used in combination with anti-emetic agents to treat nausea or emesis, which may result from the use of a compound of Formula (I), (II), (III), (IV), (V), (VIa), (VIb), (VIc), (VII), (VIII), (IX), (X), (Xa), (Xb), or (Xc), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formulas (I)-(X), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formulas (I)-(X), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formulas (I)-(X), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, parametha-sone, prednicarbate, prednisone/prednisolone, rimexolone, tixocortol, triamcinolone, and ulobetasol.

In one embodiment, a compound of Formulas (I)-(X), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745, 337 and NS398).

In some embodiments, compounds of Formulas (I)-(X), or a pharmaceutically acceptable salt thereof, are co-administered with analgesics.

In some embodiments, a compound of Formulas (I)-(X), or a pharmaceutically acceptable salt thereof, is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

In some embodiments, a compound of Formulas (I)-(X), or a pharmaceutically acceptable salt thereof, is used in the treatment of breast cancer in combination with at least one additional treatment option for the breast cancer. In some embodiments, a compound of Formulas (I)-(X), or a pharmaceutically acceptable salt thereof, is used either alone or in combination with other agents used to treat breast cancer, including but not limited to aromatase inhibitors, anthracylines, platins, nitrogen mustard, alkylating agents, taxanes, nucleoside analogs, a phosphoinositide 3-kinase (PI3K)/mTOR pathway inhibitor, CDK 4/6 inhibitors, HER-2 inhibitors, EGFR inhibitors, PD-1 inhibitors, poly ADP-ribose polymerase (PARP) inhibitors, histone deacetylase (HDAC) inhibitors, and HSP90 inhibitors. Illustrative agents used to treat breast cancer, include, but are not limited to, fulvestrant, tamoxifen, anastrozole, letrozole, exemestane, GDC0032, goserelin, leuprolide, raloxifene, toremifene, megestrol acetate, bazedoxifene, cisplatin, carboplatin, capecitabine, cyclophosphamide, docetaxel, doxorubicin, epirubicin, eribulin, filgrastim, fluorouracil, gemcitabine, ixabepilone, LEE011, LY2835219, mitoxantrone, methotrexate, paclitaxel, pamidronate, vinorelbine, pegfilgrastim, pertuzumab, trastuzumab, lapatinib, everolimus, bevacizumab, temsirolimus and combinations thereof, as well as others described herein. Additional non-limiting exemplary agents for the treatment of breast cancer are provided elsewhere herein. In some embodiments, a compound of Formulas (I)-(X), or a pharmaceutically acceptable salt thereof, is used either alone or in combination with breast cancer surgery. In some embodiments, breast cancer surgery comprises lumpectomy, mastectomy, sentinel node biopsy, or axillary node dissection. In some embodiments, a compound of Formulas (I)-(X), or a pharmaceutically acceptable salt thereof, is used either alone or in combination with radiation therapy. In some embodiments, radiation comprises external beam radiation or brachytherapy. In some embodiments, a compound of Formulas (I)-(X), or a pharmaceutically acceptable salt thereof, is used either alone or in combination with hormone therapy (i.e. hormone blocking therapy). In some embodiments, hormone therapy comprises the use of a selective estrogen receptor modulator (e.g. tamoxifen), aromatase inhibitor, or fulvestrant. In some embodiments, a compound of Formulas (I)-(X), or a pharmaceutically acceptable salt thereof, is used either alone or in combination with surgery to remove the ovaries or medications to stop the ovaries from making estrogen. In some embodiments, a compound of Formulas (I)-(X), or a pharmaceutically acceptable salt thereof, is used either alone or in combination with trastuzumab, lapatinib, or bevacizumab. In some embodiments, a compound of Formulas (I)-(X), or a pharmaceutically acceptable salt thereof, is used either alone or in combination with bone-building drugs to prevent breast cancer recurrence (e.g. zoledronic acid (Reclast, Zometa)).

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Intermediate 1

1-(2-Hydroxy-5-((tetrahydro-2H-pyran-2-yl)oxy)phenyl)-2-(3-((tetrahydro-2H-pyran-2-yl)oxy)phenyl)ethanone

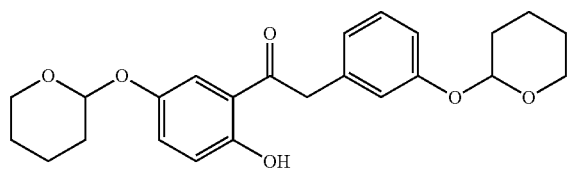

Step 1: 2-(3-Methoxyphenyl)acetyl chloride

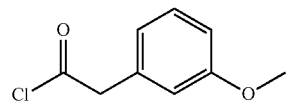

Thionyl chloride (1 L, 13.7 mol) was added over 30 min to a suspension of 2-(3-methoxyphenyl)acetic acid (530 g, 3.19 mol) and dry dichloromethane (3 L) in an ice bath. N,N-Dimethylformamide (15 mL) was added dropwise over 10 min keeping the internal temperature below 20° C. The ice bath was removed, and the reaction mixture was stirred until gas evolution has ceased. The mixture was heated at reflux (~50° C.) for 3 h, stirred at room temperature overnight, and then concentrated to give a yellow oil which was used directly in the next step.

Step 2: 1-(2,5-Dimethoxyphenyl)-2-(3-methoxyphenyl)ethanone

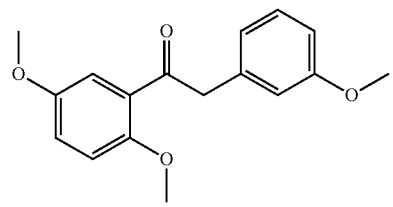

1,4-Dimethoxybenzene (400 g, 3.19 mol) was added to a suspension of AlCl$_3$ (400 g, 3.5 mol) and dry dichloromethane (10 L) in an ice/dry ice bath. A solution of 2-(3-methoxyphenyl)acetyl chloride (606 g, 3.19 mol) in dichloromethane (1 L) was added dropwise over 3 h keeping the internal temperature below 0° C. The resulting mixture was stirred at 0° C. for 1 h, poured into ice water (5 L) over 30 min with stirring (exothermic), and then extracted with dichloromethane (5 L×2). The combined organic layers were washed with 1 N aqueous HCl (2 L), saturated aqueous NaHCO$_3$ (2 L), and then brine (2 L). The resulting solution was dried (MgSO$_4$), concentrated, and purified by silica gel chromatography [petroleum ether (bp: 60-90° C.)/ethyl acetate-5:1] to give the title compound (500 g, 55%). $^1$H NMR (400 MHz, CDCl$_3$): δ 7.25 (m, 2H), 7.01 (dd, J=9.0, 3.2 Hz, 1H), 6.92 (d, J=9.0 Hz, 1H), 6.83 (m, 3H), 4.30 (s, 2H), 3.90 (s, 3H), 3.82 (s, 3H), 3.79 (s, 3H).

Step 3: 1-(2,5-Dihydroxyphenyl)-2-(3-hydroxyphenyl)ethanone

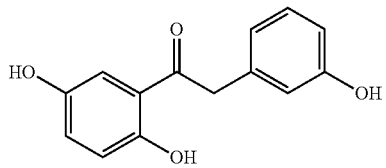

Boron tribromide (332 mL, 3.5 mol) was added dropwise (internal temperature <−60° C.) to a solution of 1-(2,5-dimethoxyphenyl)-2-(3-methoxyphenyl)ethanone (264 g, 0.92 mol) in dry dichloromethane (1 L) at −78° C. The mixture was stirred at −78° C. for 30 min, allowed to warmed to 0° C. over 30 min, and then stirred at 0° C. for an additional 1 h. Methanol (100 mL) and then water (100 mL) were added dropwise keeping the internal temperature below 20° C., and the mixture was stirred at room temperature for 1 h. The resulting precipitate was collected by filtration, washed with water (500 mL), and dried to afford the title compound (125 g, 57%). $^1$H NMR (400 MHz, DMSO-d$_6$): δ 11.24 (s, 1H), 9.34 (s, 1H), 9.20 (s, 1H), 7.26 (d, J=3.0 Hz, 1H), 7.10 (t, J=7.8 Hz, 1H), 6.98 (dd, J=8.9, 3.0 Hz, 1H), 6.83 (d, J=8.9 Hz, 1H), 6.70 (m, 3H), 4.24 (s, 2H).

Step 4: 1-(2-Hydroxy-5-((tetrahydro-2H-pyran-2-yl)oxy)phenyl)-2-(3-((tetrahydro-2H-pyran-2-yl)oxy)phenyl)ethanone

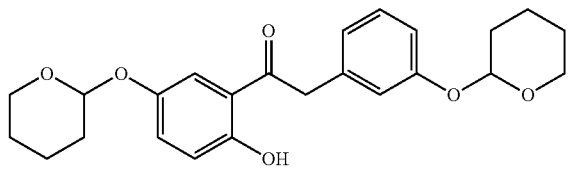

Pyridinium p-toluenesulfonate (53.6 g, 0.2 mol) was added over 1 h to a solution of 1-(2,5-dihydroxyphenyl)-2-(3-hydroxyphenyl)ethanone (280 g, 1.06 mol), 3,4-dihydro-2H-pyran (628 g, 7.48 mol), and dichloromethane (2.5 L) at 5-8° C. The mixture was stirred at room temperature for 4 h, concentrated, and then purified by silica gel chromatography [petroleum ether (bp: 60-90° C.)/ethyl acetate-10:1] to give the title compound (305 g, 70%). $^1$H NMR (400 MHz, CDCl$_3$): δ 11.88 (s, 1H), 7.60 (m, 1H), 7.30 (m, 2H), 7.00 (m, 2H), 6.92 (m, 2H), 5.42 (m, 1H), 5.28 (m, 1H), 4.25 (s, 2H), 3.92 (m, 2H), 3.62 (m, 2H), 1.55-2.07 (m, 12H).

Intermediate 2

2-(3,4-Difluoro-5-((tetrahydro-2H-pyran-2-yl)oxy)phenyl)-1-(2-hydroxy-5-((tetrahydro-2H-pyran-2-yl)oxy)phenyl)ethanone

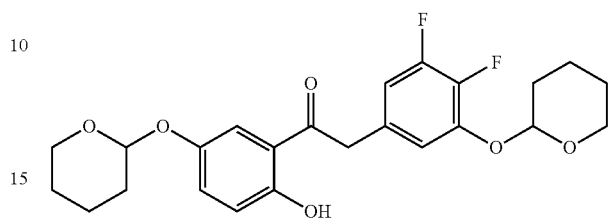

Step 1: 2-(3,4-Difluoro-5-methoxyphenyl)-1-(2,5-dimethoxyphenyl)ethanone

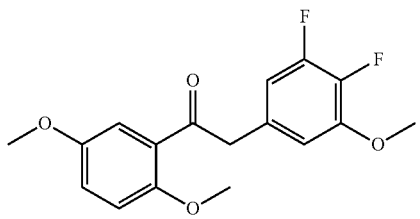

A mixture of tris(dibenzylideneacetone)dipalladium(0) (345 mg, 0.38 mmol), 2,2'-bis(diphenylphosphino)-1,1'-binaphthalene (560 mg, 0.90 mmol), and sodium tert-butoxide (3.25 g, 33.8 mmol) was degassed by vacuum/nitrogen cycles (3×). Tetrahydrofuran (70 mL), 5-bromo-1,2-difluoro-3-methoxybenzene (5.50 g, 24.7 mmol), and 1-(2,5-dimethoxyphenyl)ethanone (5.40 g, 30.0 mmol) were added to the reaction mixture. The reaction mixture was heated at 70° C. overnight, allowed to cool to room temperature, diluted with H$_2$O, and then extracted with ether (2×). The organic phase was washed (brine), dried (Na$_2$SO$_4$), and concentrated under reduced pressure. The crude material was purified on a silica gel column to give the title compound (2.69 g, 34%) as a white solid. $^1$H NMR (400 MHz, DMSO-d$_6$): δ 7.16-7.10 (m, 3H), 6.91-6.87 (m, 1H), 6.86-6.80 (m, 1H), 4.26 (s, 2H), 3.87 (s, 3H), 3.86 (s, 3H), 3.73 (s, 3H).

Step 2: 2-(3,4-Difluoro-5-((tetrahydro-2H-pyran-2-yl)oxy)phenyl)-1-(2-hydroxy-5-((tetrahydro-2H-pyran-2-yl)oxy)phenyl)ethanone

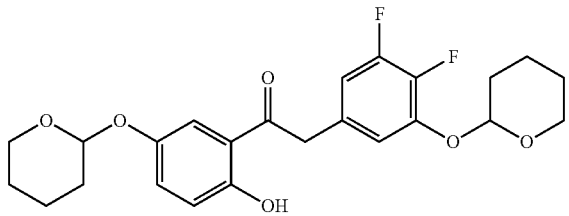

The title compound was synthesized as described in the synthesis of Intermediate 1 (Steps 3-4) using 2-(3,4-difluoro-5-methoxyphenyl)-1-(2,5-dimethoxyphenyl)ethanone as starting material. $^1$H NMR (400 MHz, DMSO-d$_6$): δ 11.20 (d, J=1.4 Hz, 1H), 7.54 (d, J=3.0 Hz, 1H), 7.25 (dd, J=8.9, 3.0 Hz, 1H), 7.06-7.01 (m, 1H), 7.00-6.94 (m, 1H), 6.92 (d, J=8.9 Hz, 1H), 5.53-5.49 (m, 1H), 5.43-5.39 (m, 1H), 4.46-4.37 (m, 2H), 3.82-3.72 (m, 2H), 3.60-3.49 (m, 2H), 1.93-1.69 (m, 6H), 1.66-1.45 (m, 6H).

Intermediate 3

1-(2-Hydroxy-5-((tetrahydro-2H-pyran-2-yl)oxy)phenyl)-2-(4-((tetrahydro-2H-pyran-2-yl)oxy)phenyl)ethanone

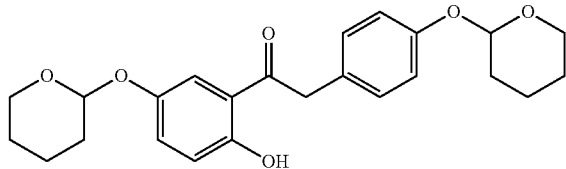

The title compound was synthesized as described in the synthesis of Intermediate 2 using 1-(2,5-dimethoxyphenyl)ethanone and 1-bromo-4-methoxy-benzene as starting materials. $^1$H NMR (400 MHz, DMSO-d$_6$): δ 11.39 (s, 1H), 7.58 (d, J=3.2 Hz, 1H), 7.24 (dd, J=8.8, 2.8 Hz, 1H), 7.18 (d, J=8.4 Hz, 2H), 6.96 (d, J=8.4 Hz, 2H), 6.92 (d, J=8.8 Hz, 1H), 5.42 (t, J=3.2 Hz, 1H), 5.39 (t, J=3.2 Hz, 1H), 4.33 (m, 2H), 3.85-3.70 (m, 2H), 3.60-3.50 (m, 2H), 1.95-1.75 (m, 6H), 1.70-1.45 (m, 6H).

Intermediate 4

2-(3-Fluoro-4-((tetrahydro-2H-pyran-2-yl)oxy)phenyl)-1-(2-hydroxy-5-((tetrahydro-2H-pyran-2-yl)oxy)phenyl)ethanone

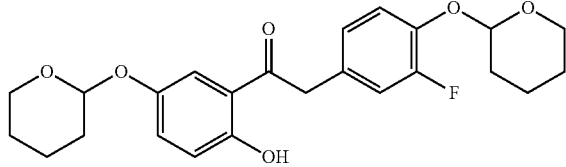

Step 1: 1-(2,5-Dimethoxyphenyl)-2-(3-fluoro-4-methoxyphenyl)ethanone

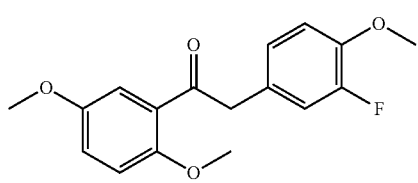

1,4-dimethoxybenzene (13.5 g, 97.7 mmol) and 2-(3-fluoro-4-methoxyphenyl)acetic acid (10.0 g, 54.3 mmol) were added to polyphosphoric acid (55 mL) at 75° C. The reaction was mixed thoroughly with a spatula until homogenous, heated at 75° C. for 5 h, cooled to 50° C., and then quenched by portion-wise addition of water (55 mL) while stirring with a spatula. The mixture was cooled to 0° C., diluted with water (55 mL), and then extracted with ether (3×). The combined organic extracts were washed (brine), dried (Mg$_2$SO$_4$), filtered, concentrated, and purified by silica gel chromatography (0-30% ethyl acetate in hexanes) to give the title compound (9.28 g, 56%) as an off-white solid. $^1$H NMR (400 MHz, DMSO-d$_6$): δ 7.13-7.11 (m, 2H), 7.10-7.02 (m, 3H), 6.97-6.92 (m, 1H), 4.20 (s, 2H), 3.85 (s, 3H), 3.80 (s, 3H), 3.72 (s, 3H).

Step 2: 2-(3-Fluoro-4-((tetrahydro-2H-pyran-2-yl)oxy)phenyl)-1-(2-hydroxy-5-((tetrahydro-2H-pyran-2-yl)oxy)phenyl)ethanone

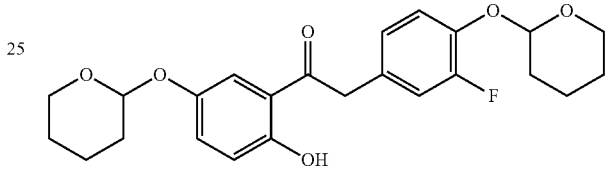

The title compound was synthesized as described in the synthesis of Intermediate 1 (Steps 3-4) using 1-(2,5-dimethoxyphenyl)-2-(3-fluoro-4-methoxyphenyl)ethanone as starting material. $^1$H NMR (400 MHz, DMSO-d$_6$): δ 11.30 (s, 1H), 7.56 (d, J=3.0 Hz, 1H), 7.25 (dd, J=9.0, 3.0 Hz, 1H), 7.20 (t, J=8.6 Hz, 1H), 7.15 (dd, J=12.5, 2.1 Hz, 1H), 7.01-6.97 (m, 1H), 6.91 (d, J=9.0 Hz, 1H), 5.50-5.45 (m, 1H), 5.42-5.30 (m, 1H), 4.43-4.32 (m, 2H), 3.82-3.74 (m, 2H), 3.58-3.50 (m, 2H), 1.94-1.67 (m, 6H), 1.66-1.44 (m, 6H).

Intermediate 5

2-(2-Fluoro-4-((tetrahydro-2H-pyran-2-yl)oxy)phenyl)-1-(2-hydroxy-5-((tetrahydro-2H-pyran-2-yl)oxy)phenyl)ethanone

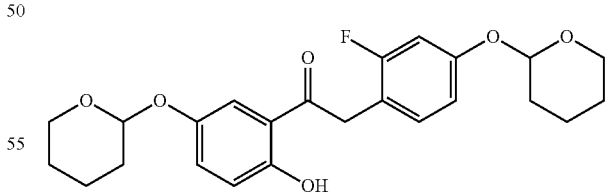

The title compound was synthesized as described in the synthesis of Intermediate 4 using 2-(2-fluoro-4-methoxyphenyl)acetic acid and 1,4-dimethoxybenzene as starting materials. $^1$H NMR (400 MHz, DMSO-d$_6$): δ 11.16 (s, 1H), 7.56 (d, J=3.0 Hz, 1H), 7.25 (dd, J=8.9, 3.0 Hz, 1H), 7.21 (t, J=8.6 Hz, 1H), 6.93 (d, J=8.9 Hz, 1H), 6.87 (dd, J=11.9, 2.9 Hz, 1H), 6.83 (dd, J=8.4, 2.3 Hz, 1H), 5.51-5.48 (m, 1H), 5.42-5.39 (m, 1H), 4.46-4.34 (m, 2H), 3.83-3.70 (m, 2H), 3.60-3.51 (m, 2H), 1.95-1.68 (m, 6H), 1.66-1.50 (m, 6H).

Intermediate 6

(S)-2-((R)-3-Methylpyrrolidin-1-yl)propan-1-ol

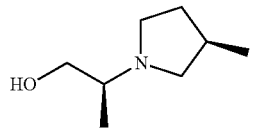

Step 1: (R)-2-Methylbutane-1,4-diyl dimethanesulfonate

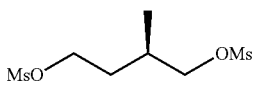

To a solution of (R)-2-methylbutane-1,4-diol (30 g, 0.29 mol) in DCM (600 mL) was added triethylamine (100 mL, 0.72 mol). The solution was cooled to −20° C., and methanesulfonyl chloride (49 mL, 0.63 mol) was added dropwise over 30 min with vigorous stirring. The resulting mixture was stirred for additional 1 h while the temperature was maintained between −20 and −15° C. The mixture was allowed to warm to 0° C. and then poured into cold 1N HCl solution (100 mL). The organic layer was separated, and aqueous phase was extracted with DCM (100 mL). The combined organic extracts were washed with saturated NaHCO₃, brine, dried over MgSO₄, filtered and concentrated in vacuo. The resulting product (75.9 g, quant) was used directly for the next step. $^1$H NMR (400 MHz, DMSO-d₆): δ 4.32-4.22 (m, 2H), 4.13-4.03 (m, 2H), 3.18 (s, 3H), 3.18 (s, 3H), 2.02-1.92 (m, 1H), 1.87-1.77 (m, 1H), 1.61-1.50 (m, 1H), 1.07 (d, J=6.8 Hz, 3H).

Step 2: (S)-2-((R)-3-Methylpyrrolidin-1-yl)propan-1-ol

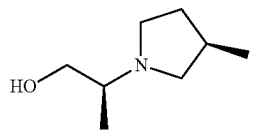

(R)-2-Methylbutane-1,4-diyl dimethanesulfonate (37.5 g, 0.144 mol) was added to neat (S)-2-aminopropan-1-ol (54.8 g, 0.730 mol). The mixture was stirred in a room temperature water bath to minimize the exotherm. After 24 h, the reaction was diluted with DCM (150 mL), saturated potassium carbonate solution (150 mL), and just enough water (60 mL) to dissolve the resulting precipitate. The organic layer was separated, and the aqueous layer was extracted with DCM (150 mL). The organic layers were combined, dried (Na₂SO₄), filtered, concentrated, and purified by silica gel chromatography (10:7; ethyl acetate:hexanes→10:7:2:1; ethyl acetate:hexanes:methanol:triethylamine) to give the title compound (17.9 g, 87%) as a pale yellow oil. $^1$H NMR (400 MHz, DMSO-d₆): δ 4.33 (t, J=5.4 Hz, 1H), 3.48 (m, 1H), 3.18 (m, 1H), 2.79 (dd, J=8.6, 7.6 Hz, 1H), 2.58 (m, 1H), 2.48 (m, 1H), 2.26 (m, 1H), 2.08 (m, 1H), 2.01 (dd, J=8.6, 6.8 Hz, 1H), 1.88 (m, 1H), 1.20 (m, 1H), 0.98 (d, J=6.4 Hz, 3H), 0.96 (d, J=6.5 Hz, 3H); $^{13}$C NMR (100 MHz, DMSO-d₆): δ 64.5, 60.1, 58.8, 50.4, 32.0, 20.3, 12.2; LCMS: 144.3 [M+H]+.

Intermediate 7

6-(2-(Pyrrolidin-1-yl)ethoxy)nicotinaldehyde

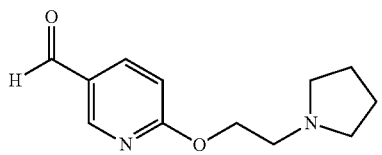

To a solution of 2-(pyrrolidin-1-yl)ethanol (750 mg, 6.51 mmol) in DMF (10 mL) at 0° C. was added potassium tert-butoxide (803 mg, 7.15 mmol). The mixture was stirred at 0° C. for 15 min, and 6-chloronicotinaldehyde (1.03 g, 7.28 mmol) in DMF (2 mL) was added. After stirring for 1 h at room temperature, the reaction was quenched at 0° C. with saturated ammonium chloride (1 mL). The reaction was diluted with ethyl acetate (75 mL), washed (2×50 mL H₂O, 50 mL brine), and dried over Na₂SO₄. The solvent was removed under reduced pressure and the crude material was purified on a silica gel column to give the desired compound (306 mg, 21%). $^1$H NMR (300 MHz, CDCl₃): δ 9.97 (s, 1H), 8.86 (s, 1H), 8.07 (d, J=8.2 Hz, 1H), 6.90 (d, J=8.2 Hz, 1H), 4.56 (t, J=5.6 Hz, 2H), 2.94 (t, J=5.6 Hz, 2H), 2.66 (br s, 4H), 1.84 (br s, 4H).

Intermediate 8

6-((S)-2-((R)-3-Methylpyrrolidin-1-yl)propoxy)nicotinaldehyde

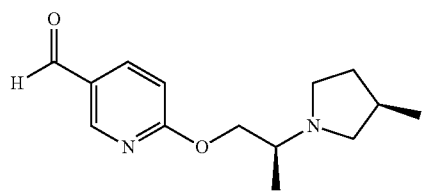

The title compound was synthesized as described in the synthesis of Intermediate 7 using 6-chloronicotinaldehyde and Intermediate 6 as starting materials. $^1$H NMR (300 MHz, DMSO-d₆): δ 9.96 (s, 1H), 8.75 (d, J=2.4 Hz, 1H), 8.12 (dd, J=8.7, 2.4 Hz, 1H), 6.99 (d, J=2.4 Hz, 1H), 4.45 (m, 1H), 4.26 (m, 1H), 2.60-2.95 (m, 4H), 2.12 (m, 2H), 1.93 (m, 1H), 1.25 (m, 1H), 1.11 (d, J=6.4 Hz, 3H), 0.96 (d, J=6.4 Hz, 3H).

Intermediate 9

5-((S)-2-((R)-3-Methylpyrrolidin-1-yl)propoxy)pyrazine-2-carbaldehyde

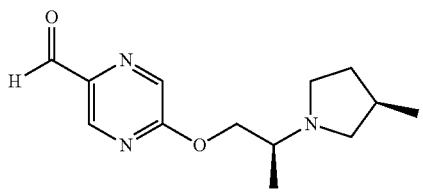

Step 1: 5-((S)-2-((R)-3-Methylpyrrolidin-1-yl)propoxy)pyrazine-2-carbonitrile

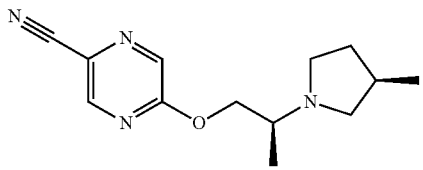

A mixture of 5-bromopyrazine-2-carbonitrile (1.0 g, 5.4 mmol), Intermediate 6 (1.55 g, 10.8 mmol), palladium (II) acetate (0.18 g, 0.27 mmol), [1,1'-binaphthalen]-2-yldi-tert-butylphosphine (0.64 g, 1.62 mmol), and cesium carbonate (3.5 g, 10.8 mmol) in toluene (27 mL) was degassed by three vacuum/nitrogen cycles. The resulting mixture was heated at 110° C. overnight, allowed to cool to room temperature, and then quenched with brine (50 mL). The mixture was extracted with ethyl acetate (3×100 mL). The combined organics were washed with water (25 mL), washed with brine (25 mL), dried over sodium sulfate, filtered and concentrated under reduced pressure to give a residue. This residue was purified by silica gel column chromatography (0-20% methanol in dichloromethane) to afford the title compound (0.55 g, 41%) as a pale yellow gum. $^1$H NMR (300 MHz, CDCl$_3$): δ 8.46 (d, J=1.4 Hz, 1H), 8.33 (d, J=1.4 Hz, 1H), 4.51 (dd, J=11.1, 4.6 Hz, 1H), 4.36 (dd, J=11.1, 5.5 Hz, 1H), 3.03 (t, J=8.0 Hz, 1H), 2.94-2.55 (m, 3H), 2.34-1.99 (m, 3H), 1.49-1.30 (m, 1H), 1.25 (d, J=6.6 Hz, 3H), 1.05 (d, J=6.6 Hz, 3H).

Step 2: 5-((S)-2-((R)-3-Methylpyrrolidin-1-yl)propoxy)pyrazine-2-carbaldehyde

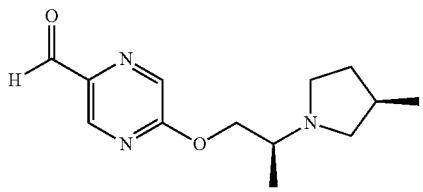

To a solution of 5-((S)-2-((R)-3-methylpyrrolidin-1-yl)propoxy)pyrazine-2-carbonitrile (0.5 g, 2 mmol) in THF (10 mL) at −78° C. was added DIBAL-H (4 mL, 1 M in toluene, 4 mmol). The resulting solution was stirred at −78° C. for 2 h and then quenched with hydrochloric acid (2 mL, 2M Et$_2$O). The mixture was stirred for 20 min at −78° C. followed by addition of aqueous saturated sodium carbonate (5 mL). The resulting mixture was allowed to warm to room temperature and extracted with ethyl acetate (3×100 mL). The combined organic extracts were washed with water (25 mL), washed with brine (25 mL), dried (Na$_2$SO$_4$), filtered, and concentrated to give a residue. This residue was passed through a pad of silica gel (10% methanol in dichloromethane) affording the title compound (0.41 g, 82%) as a pale yellow gum. LCMS: 250.5 [M+H]$^+$.

Intermediate 10

5-(2-(Pyrrolidin-1-yl)ethoxy)pyrazine-2-carbaldehyde

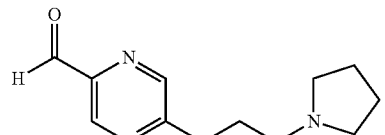

The title compound was synthesized as described in the synthesis of Intermediate 9 using 5-bromopyrazine-2-carbonitrile and 2-(pyrrolidin-1-yl)ethanol as starting materials. $^1$H NMR (300 MHz, DMSO-d$_6$): δ 9.97 (s, 1H), 8.77 (d, J=1.3 Hz, 1H), 8.50 (d, J=1.3 Hz, 1H), 4.53-4.37 (m, 2H), 2.86-2.78 (m, 2H), 2.52-2.49 (m, 4H), 1.69-1.65 (m, 4H).

Intermediate 11

5-((S)-2-((R)-3-Methylpyrrolidin-1-yl)propoxy)picolinaldehyde

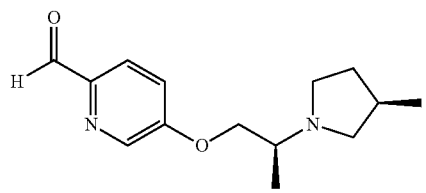

A suspension of 5-iodopicolinaldehyde (1.1 g, 4.7 mmol), Intermediate 6 (880 mg, 6.1 mmol), cesium carbonate (3.1 g, 9.4 mmol), and CuI (90 mg, 0.47 mmol) in m-xylene (5 mL) was degassed by vacuum/nitrogen cycles (3×). The mixture was heated at 130° C. for 2 days, allowed to cool to room temperature, and then diluted with ethyl acetate. The mixture was filtered through a pad of Celite, and the Celite was washed with additional ethyl acetate. The filtrate was washed (H$_2$O and then brine), dried (Na$_2$SO$_4$), and concentrated under reduced pressure. The crude material was purified on a silica gel column to give the title compound (218 mg, 19%) as a brown oil. $^1$H NMR (400 MHz, DMSO-d$_6$): δ 9.88 (s, 1H), 8.50 (d, J=2.7 Hz, 1H), 7.92 (d, J=8.7 Hz, 1H), 7.60 (dd, J=8.7, 2.7 Hz, 1H), 4.23 (dd, J=9.9, 4.8 Hz, 1H), 4.02 (dd, J=9.9, 5.9 Hz, 1H), 2.89-2.79 (m, 1H), 2.79-2.63 (m, 2H), 2.62-2.54 (m, 1H), 2.18-2.05 (m, 2H), 1.96-1.83 (m, 1H), 1.32-1.18 (m, 1H), 1.13 (d, J=6.6 Hz, 3H), 0.97 (d, J=6.4 Hz, 3H).

Intermediate 12

6-(2-(4-Iodophenyl)-4-methyl-6-((tetrahydro-2H-pyran-2-yl)oxy)-2H-chromen-3-yl)-1-(tetrahydro-2H-pyran-2-yl)-1H-indazole

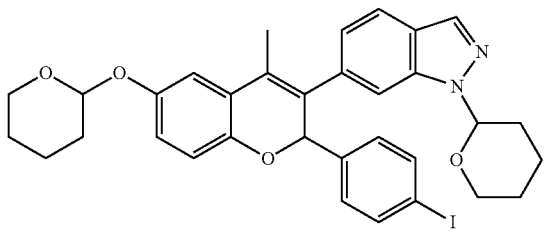

Step 1: 6-Bromo-1-(tetrahydro-2H-pyran-2-yl)-1H-indazole

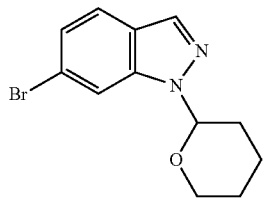

A 250-mL round-bottom flask equipped with a magnetic stir bar, a rubber septum, and a nitrogen inlet was charged with 6-bromo-1H-indazole (10 g, 50.7 mmol) and anhydrous dichloromethane (102 mL). To this solution, 3,4-dihydro-2H-pyran (23 mL, 253.8 mmol) was added in one portion at room temperature followed by addition of pyridinium p-toluene sulfonate (1.28 g, 5 mmol). The resulting mixture was stirred at room temperature for 48 h. Upon completion by TLC (or LCMS), the reaction mixture was quenched with water and extracted with dichloromethane (3×100 mL). The combined organic extracts were washed with water (100 mL), washed with brine (50 mL), dried over sodium sulfate, filtered, concentrated, and purified by silica gel chromatography (0-10% ethyl acetate in hexanes) to give the title compound as a pale yellow oil (12.7 g, 89%). $^1$H NMR (400 MHz, DMSO-$d_6$): δ 8.14 (s, 1H), 8.04 (br, 1H), 7.75 (d, J=8.4 Hz, 1H), 7.32 (dd, J=8.6, 1.6 Hz, 1H), 5.88 (dd, J=9.8, 2.6 Hz, 1H), 3.89-3.72 (m, 2H), 2.44-2.31 (m, 1H), 2.06-1.91 (m, 2H), 1.80-1.68 (m, 1H), 1.60-1.47 (m, 2H).

Step 2: 1-(2,5-Dimethoxyphenyl)-2-(1-(tetrahydro-2H-pyran-2-yl)-1H-indazol-6-yl)ethanone

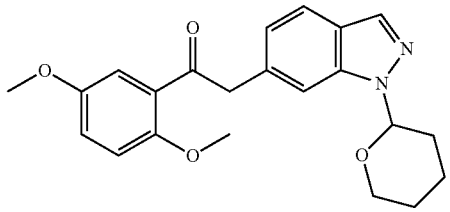

A mixture of tris(dibenzylideneacetone)dipalladium(0) (135 mg, 0.147 mmol), binap (201 mg, 0.323 mmol), and sodium tert-butoxide (1.11 g, 11.6 mmol) was degassed by vacuum/nitrogen cycles (3×). Tetrahydrofuran (30 mL), 6-bromo-1-(tetrahydro-2H-pyran-2-yl)-1H-indazole (2.51 g, 8.93 mmol, dissolved in 20 mL THF), and 1-(2,5-dimethoxyphenyl)ethanone (1.7 mL, 10.7 mmol) were added to the reaction mixture. The reaction mixture was heated at 70° C. for 2 h, allowed to cool to room temperature, and diluted with ethyl acetate (150 mL). The mixture was then washed (2×50 mL saturated NaHCO$_3$, 50 mL brine), dried (Na$_2$SO$_4$), and concentrated under reduced pressure. The crude material was purified on a silica gel column to give the title compound (2.49 g, 72%). $^1$H NMR (300 MHz, CDCl$_3$): δ 7.99 (d, J=0.8 Hz, 1H), 7.66 (dd, J=8.3, 0.8 Hz, 1H), 7.48 (s, 1H), 7.26 (s, 1H), 7.08-7.02 (m, 2H), 6.93 (d, J=9.1 Hz, 1H), 5.71 (dd, J=9.5, 2.8 Hz, 1H), 4.54-4.41 (m, 2H), 4.08-4.00 (m, 1H), 3.92 (s, 3H), 3.79 (s, 3H), 3.77-3.67 (m, 1H), 2.67-2.50 (m, 1H), 2.25-2.01 (m, 2H), 1.85-1.63 (m, 3H); LCMS: 297.1 [(M-THP)+H]$^+$.

Step 3: 1-(2,5-Dimethoxyphenyl)-2-(1H-indazol-6-yl)ethanone

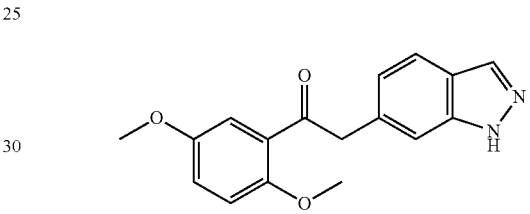

A solution of 1-(2,5-dimethoxyphenyl)-2-(1-(tetrahydro-2H-pyran-2-yl)-1H-indazol-6-yl)ethanone (2.16 g, 5.68 mmol) and HCl (4.0 mL, 2N in diethyl ether, 8.0 mmol) in methanol (40 mL) was heated at 70° C. for 1.5 h, allowed to cool to room temperature, and concentrated under reduced pressure. The crude oil was diluted with ethyl acetate, and the resulting solution was washed (100 mL saturated NaHCO$_3$, 50 mL brine), dried (Na$_2$SO$_4$), concentrated under reduced pressure, and purified on a silica gel column to give the title compound (1.55 g, 92%). $^1$H NMR (300 MHz, DMSO-$d_6$): δ 12.95 (s, 1H), 8.00 (s, 1H), 7.66 (d, J=8.4 Hz, 1H), 7.35 (s, 1H), 7.15-7.10 (m, 2H), 7.16-7.07 (m, 1H), 6.95 (dd, J=8.3, 1.3 Hz, 1H), 4.39 (s, 2H), 3.87 (s, 3H), 3.72 (s, 3H); LCMS: 297.1 [M+H]$^+$.

Step 4: 1-(2,5-Dihydroxyphenyl)-2-(1H-indazol-6-yl)ethanone

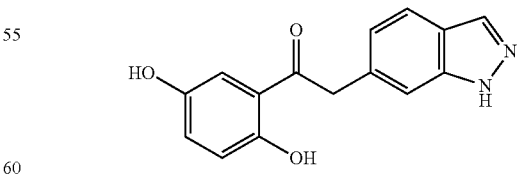

To a solution of 1-(2,5-dimethoxyphenyl)-2-(1H-indazol-5-yl)ethanone (1.55 g, 5.24 mmol) in DCM (110 mL) at −78° C., boron tribromide (4.0 mL, 42 mmol) was added dropwise. The reaction mixture was allowed to warm to room temperature, stirred overnight, re-cooled to −78° C., and then quenched with methanol (10 mL). The reaction mixture was allowed to warm to room temperature, poured into saturated NaHCO₃ (150 mL), and extracted with ethyl acetate (2×200 mL). The combined organic extracts were washed (100 mL saturated NaHCO₃, 100 mL brine), dried (Na₂SO₄), and concentrated under reduced pressure to give the title compound (1.39 g, 100%). ¹H NMR (300 MHz, DMSO-d₆): δ 13.00 (br, 1H), 11.21 (s, 1H), 9.22 (br, 1H), 8.25 (s, 1H), 7.68 (d, J=8.3 Hz, 1H), 7.42 (s, 1H), 7.33 (d, J=2.9 Hz, 1H), 7.04-6.96 (m, 2H), 6.82 (d, J=8.8 Hz, 1H), 4.50 (s, 2H); LCMS: 269.1 [M+H]⁺.

Step 5: 6-Hydroxy-3-(1H-indazol-6-yl)-2-(4-iodophenyl)chroman-4-one

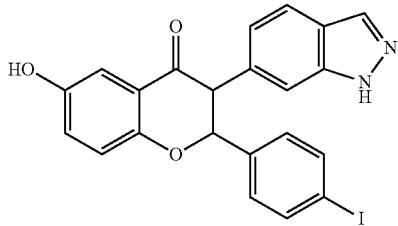

A solution of 1-(2,5-dihydroxyphenyl)-2-(1H-indazol-5-yl)ethanone (1.01 g, 3.77 mmol), 4-iodobenzaldehyde (922 mg, 3.97 mmol), piperidine (125 uL, 1.26 mmol), and 1,8-diazabicyclo[5.4.0]undec-7-ene (185 uL, 1.26 mmol) in s-butanol (8 mL) was heated at reflux. Using a Dean-Stark trap, half (4 mL) of the solvent was collected over 45 min, and the reaction was kept at reflux without further concentration for additional 4.5 h. The reaction mixture was cooled to 90° C., i-propanol (8 mL) was added, and the reaction was allowed to cool to room temperature and stirred overnight. The solvent was removed under reduced pressure and the residue was purified on a silica gel column to yield the title compound (1.61 g, 88%) as a 1:2.5 mixture of cis/trans isomers. LCMS: 483.0 [M+H]⁺.

Step 6: 2-(4-Iodophenyl)-3-(1-(tetrahydro-2H-pyran-2-yl)-1H-indazol-6-yl)-6-((tetrahydro-2H-pyran-2-yl)oxy)chroman-4-one

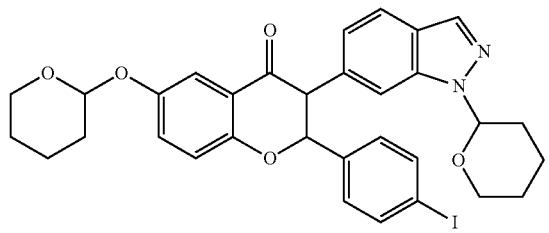

Pyridinium p-toluene sulfonate (160 mg, 0.64 mmol) and 3,4-dihydro-2H-pyran (2.3 mL, 24.8 mmol) were added to a mixture of 6-hydroxy-3-(1H-indazol-6-yl)-2-(4-iodophenyl)chroman-4-one (1.51 g, 3.12 mmol) and dichloromethane (100 mL). After stirring overnight, the reaction was washed (2×50 mL saturated NaHCO₃, 50 mL brine), dried (Na₂SO₄), and concentrated under reduced pressure. The crude material was purified on a silica gel column to give the title compound (1.55 g, 77%) as a mixture of cis/trans chromanone and N1/N2-THP-indazole regio isomers. LCMS: 651.0 [M+H]⁺.

Step 7: 3-(1H-Indazol-6-yl)-2-(4-iodophenyl)-4-methyl-2H-chromen-6-ol

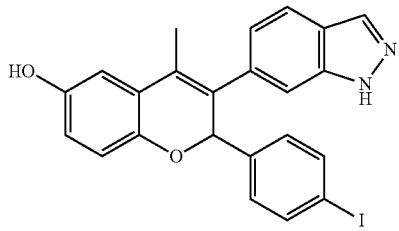

To a solution of 2-(4-iodophenyl)-3-(1-(tetrahydro-2H-pyran-2-yl)-1H-indazol-6-yl)-6-((tetrahydro-2H-pyran-2-yl)oxy)chroman-4-one (1.55 g, 2.38 mmol) in THF (20 mL) cooled in an ice-bath, was added dropwise a solution of CH₃MgCl (3.0 M in THF, 2.4 mL, 7.2 mmol). The mixture was stirred at 0° C. for 10 min, and then at room temperature for 2 h. The reaction mixture was cooled to 0° C., and saturated aqueous NH₄Cl (3 mL) was added. The reaction mixture was allowed to warm to room temperature and extracted with ethyl acetate (3×50 mL). The combined organic extracts were dried (Na₂SO₄), concentrated under reduced pressure, and dissolved in 80% acetic acid/H₂O (10 mL). The mixture was heated at 90° C. for 2 days and concentrated under reduced pressure. The residue was dissolved in ethyl acetate (100 mL), washed (2×50 mL saturated NaHCO₃, 50 mL brine), dried (Na₂SO₄), and concentrated under reduced pressure. The crude material was purified on a silica gel column to give the desired compound (550 mg, 48%). ¹H NMR (300 MHz, DMSO-d₆): δ 13.05 (s, 1H), 9.02 (s, 1H), 8.04 (t, J=1.2 Hz, 1H), 7.74 (d, J=8.3 Hz, 1H), 7.61 (d, J=8.3 Hz, 2H), 7.36-7.34 (m, 1H), 7.12 (d, J=8.3 Hz, 2H), 7.05 (dd, J=8.3, 1.2 Hz, 1H), 6.79-6.77 (m, 1H), 6.57-6.50 (m, 2H), 6.04 (s, 1H), 2.05 (s, 3H); LCMS: 481.0 [M+H]⁺.

Step 8: 6-(2-(4-Iodophenyl)-4-methyl-6-((tetrahydro-2H-pyran-2-yl)oxy)-2H-chromen-3-yl)-1-(tetrahydro-2H-pyran-2-yl)-1H-indazole

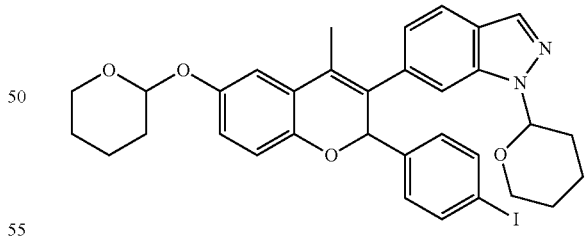

To a solution of 3-(1H-indazol-6-yl)-2-(4-iodophenyl)-4-methyl-2H-chromen-6-ol (550 mg, 1.15 mmol) and pyridinium p-toluene sulfonate (60 mg, 0.24 mmol) in DCM (30 mL) was added 3,4-dihydro-2H-pyran (0.53 mL, 5.71 mmol). The reaction mixture was stirred at room temperature overnight and then diluted with DCM (100 mL). The solution was washed (50 mL saturated NaHCO₃, 50 mL brine), dried (Na₂SO₄), and concentrated under reduced pressure. The crude material was purified by silica gel chromatography to give the title compound (700 mg, 94%) as an off-white foam. ¹H NMR (300 MHz, DMSO-d₆): δ

8.08 (s, 1H), 7.74 (d, J=8.3 Hz, 1H), 7.72-7.67 (m, 1H), 7.62 (dd, J=8.6, 1.5 Hz, 2H), 7.17-7.07 (m, 3H), 7.05-7.01 (m, 1H), 6.86-6.81 (m, 1H), 6.38 (dd, J=8.6, 1.0 Hz, 1H), 6.17 (s, 1H), 5.88-5.79 (m, 1H), 5.40-5.34 (m, 1H), 3.94-3.66 (m, 3H), 3.63-3.48 (m, 1H), 2.09 & 2.07 (2s, 3H), 1.98-1.37 (m, 12H); LCMS: 565.0 [(M-THP)+H]+.

Intermediate 13

5-(2-(4-Iodophenyl)-4-methyl-6-((tetrahydro-2H-pyran-2-yl)oxy)-2H-chromen-3-yl)-1-(tetrahydro-2H-pyran-2-yl)-1H-indazole

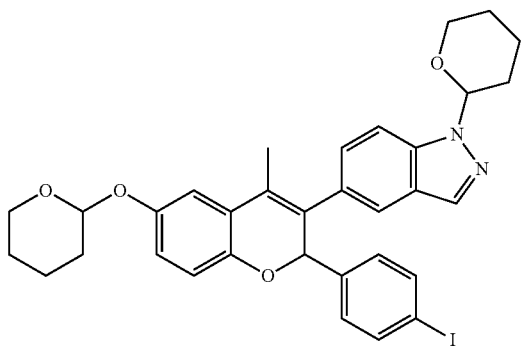

The title compound was synthesized as described in the synthesis of Intermediate 12 using 5-bromo-1H-indazole as starting material. ¹H NMR (300 MHz, DMSO-$d_6$): δ 8.09 (s, 1H), 7.74 (m, 2H), 7.60 (d, J=8.3 Hz, 2H), 7.39-7.34 (m, 1H), 7.12-7.08 (m, 2H), 7.01 (dd, J=2.7, 1.5 Hz, 1H), 6.81 (dd, J=8.9, 2.7 Hz, 1H), 6.66 (dd, J=8.7, 1.0 Hz, 1H), 6.14 (s, 1H), 5.86-5.79 (m, 1H), 5.39-5.35 (m, 1H), 3.92-3.66 (m, 3H), 3.63-3.40 (m, 1H), 2.06 (s, 3H), 1.98-1.66 (m, 6H), 1.66-1.46 (m, 6H); LCMS: 565.0 [(M-THP)+H]+.

Intermediate 14

4-(2-(4-Iodophenyl)-4-methyl-6-((tetrahydro-2H-pyran-2-yl)oxy)-2H-chromen-3-yl)-1-(tetrahydro-2H-pyran-2-yl)-1H-indazole

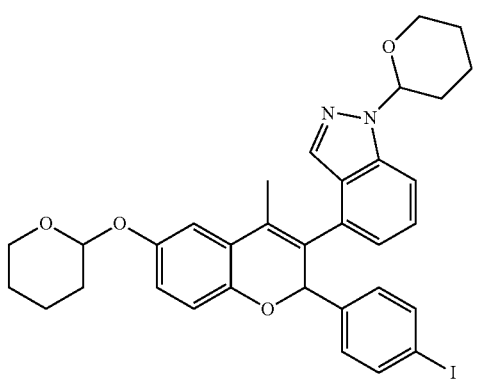

The title compound was synthesized as described in the synthesis of Intermediate 12 using 4-bromo-1H-indazole as starting material. ¹H NMR (300 MHz, DMSO-$d_6$): δ 8.03 (d, J=2.8 Hz, 1H), 7.66 (d, J=8.6 Hz, 1H), 7.57 (d, J=8.6 Hz, 2H), 7.40 (dd, J=8.4, 7.2 Hz, 1H), 7.18-7.12 (m, 2H), 7.12-7.07 (m, 1H), 7.07-7.03 (m, 1H), 6.87-6.82 (m, 1H), 6.67 (dd, J=8.6, 0.8 Hz, 1H), 6.13 (s, 1H), 5.89-5.80 (m, 1H), 5.42-5.34 (m, 1H), 3.92-3.66 (m, 3H), 3.64-3.49 (m, 1H), 1.94 (s, 3H), 1.89-1.40 (m, 12H); LCMS: 565.0 [(M-THP)+H]+.

Intermediate 15

7-(4-Iodophenyl)-9-methyl-3-(tetrahydro-2H-pyran-2-yl)-8-(3-((tetrahydro-2H-pyran-2-yl)oxy)phenyl)-3,7-dihydropyrano[3,2-e]indazole

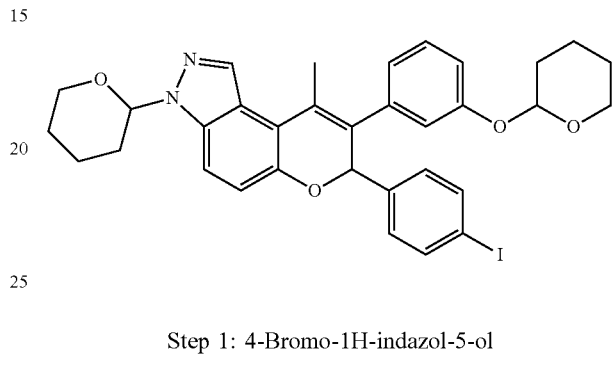

Step 1: 4-Bromo-1H-indazol-5-ol

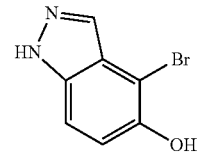

N-Bromosuccinamide (12.0 g. 67.2 mmol) was slowly added to a suspension of 1H-indazol-5-ol (10.0 g, 74.6 mmol) in dry THF (200 mL) at 0° C. The reaction mixture was stirred at this temperature for 2.5 h, poured into ice-water (300 ml) containing NaHSO₃ (6.0 g). The layers were separated, and the organic phase was dried over Na₂SO₄, filtered, and concentrated in vacuo to yield the title compound (14.1 g, 89%) as a red brown solid. ¹H NMR (400 MHz, DMSO-$d_6$): δ 13.13 (s, 1H), 9.77 (s, 1H), 7.83 (s, 1H), 7.39 (d, J=8.8 Hz, 1H), 7.08 (d, J=8.8 Hz, 1H).

Step 2: 4-Bromo-1-(tetrahydro-2H-pyran-2-yl)-5-((tetrahydro-2H-pyran-2-yl)oxy)-1H-indazole

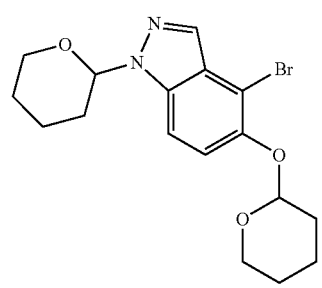

Pyridinium p-toluene sulfonate and 3,4-dihydro-2H-pyran were added to a suspension of 4-bromo-1H-indazol- 5-ol (14.1 g, 66.2 mmol) in DCM (200 mL). The reaction was stirred at room temperature overnight, and then saturated NaHCO$_3$ (0.5 L) was added. The layers were separated. The organic phase was dried over Na$_2$SO$_4$ and concentrated in vacuo. The residue was purified by silica gel column chromatography (PE:EA=20:1) to give the title compound (21.4 g, 85%) as a yellow solid. $^1$H NMR (400 MHz, CDCl$_3$): δ 7.99 (s, 1H), 7.48 (dd, J=8.8, 0.8 Hz, 1H), 7.31 (d, J=9.2 Hz, 1H), 5.69-5.65 (m, 1H), 5.44-5.43 (m, 1H), 4.01-3.97 (m, 2H), 3.76-3.69 (m, 1H), 3.62-3.59 (m, 1H), 2.57-2.48 (m, 1H), 2.17-2.00 (m, 4H), 1.95-1.87 (m, 1H), 1.76-1.63 (m, 6H).

Step 3: 2-(3-Methoxyphenyl)-1-(1-(tetrahydro-2H-pyran-2-yl)-5-((tetrahydro-2H-pyran-2-yl)oxy)-1H-indazol-4-yl)ethanol

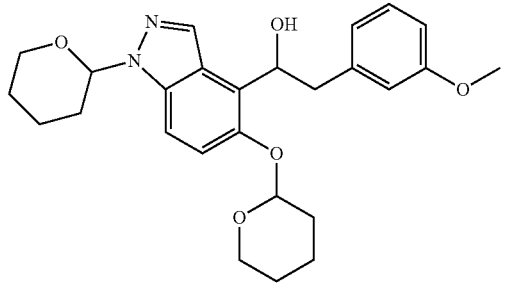

To a cold solution (−78° C.) of 4-bromo-1-(tetrahydro-2H-pyran-2-yl)-5-((tetrahydro-2H-pyran-2-yl)oxy)-1H-indazole (14.2 g, 37 mmol) in THF (200 mL) were added n-BuLi (2.5M, 34.0 ml) and TMEDA (10.3 ml) The mixture was stirred for 1 h, and 2-(3-methoxyphenyl)acetaldehyde (10.0 g, 66.7 mmol) in THF was added. The resulted mixture was stirred for 1 h at −78° C., allowed to warm to room temperature, and then quenched with saturated NH$_4$Cl. The reaction mixture was extracted with ethyl acetate (3×300 mL), and the combined organic phase was dried (Na$_2$SO$_4$) and concentrated in vacuo. The residue was purified by column chromatography (PE/EA=6:1) to afford the title compound (5.9 g, 39%) as a yellow oil.

Step 4: 2-(3-Methoxyphenyl)-1-(1-(tetrahydro-2H-pyran-2-yl)-5-((tetrahydro-2H-pyran-2-yl)oxy)-1H-indazol-4-yl)ethanol

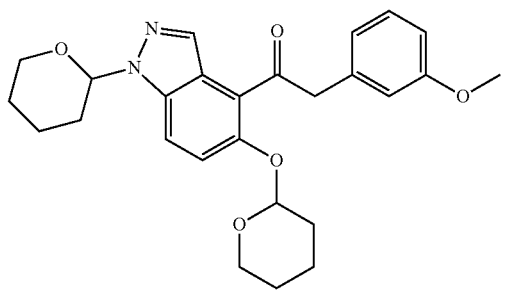

Dess-Martin periodinane (8.0 g, 19.0 mmol) was added to a solution of 2-(3-methoxyphenyl)-1-(1-(tetrahydro-2H-pyran-2-yl)-5-((tetrahydro-2H-pyran-2-yl)oxy)-1H-indazol-4-yl)ethanol (5.7 g, 12.6 mmol) in DCM (100 mL). The reaction was stirred at room temperature for 4 h, quenched with saturated Na$_2$SO$_3$, and then extracted with Et$_2$O (3×100 mL). The organic extracts were washed (10% NaOH), dried (Na$_2$SO$_4$), and concentrated in vacuo. The residue was purified by column chromatography (PE/EA=12:1) to afford the title compound (3 g, 53%) as a yellow oil.

Step 5: 1-(5-Hydroxy-1H-indazol-4-yl)-2-(3-methoxyphenyl)ethanone

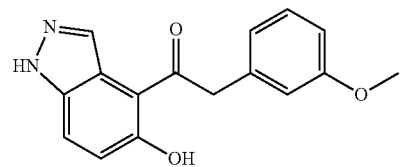

A solution of 2-(3-methoxyphenyl)-1-(1-(tetrahydro-2H-pyran-2-yl)-5-((tetrahydro-2H-pyran-2-yl)oxy)-1H-indazol-4-yl)ethanol (3 g, 6.67 mmol) in MeOH:HCl (10:1, 66 mL) was stirred for 5 h at room temperature. The reaction was quenched with saturated potassium carbonate and extracted with ethyl acetate (3×100 mL). The combined organic extracts were dried (Na$_2$SO$_4$), concentrated in vacuo, and purified by column chromatography (PE/EA=4:1) to afford the title compound (1.3 g, 70%) as a yellow solid. $^1$H NMR (400 MHz, CDCl$_3$): OH resonance was not observed; δ 13.44 (s, 1H), 8.22 (s, 1H), 7.70 (d, J=8.8 Hz, 1H), 7.30 (t, J=8.0 Hz, 1H), 7.12 (d, J=8.8 Hz, 1H), 6.90-6.82 (m, 3H), 4.49 (s, 2H), 3.81 (s, 3H).

Step 6: 1-(5-Hydroxy-1H-indazol-4-yl)-2-(3-hydroxyphenyl)ethanone

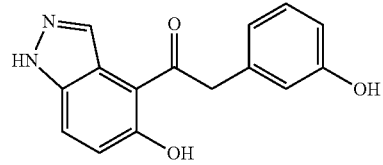

To a solution of 1-(5-hydroxy-1H-indazol-4-yl)-2-(3-methoxyphenyl)ethanone (1.3 g, 4.6 mmol) in DCM (40 mL) was slowly added boron tribromide (18.4 mL, 191 mmol). The reaction was stirred at room temperature for 2 h, quenched with NaHCO$_3$, and then extracted with ethyl acetate (3×100 mL). The combined organic phases were dried (Na$_2$SO$_4$) and concentrated in vacuo. The crude material was used directly in the next step. $^1$H NMR (400 MHz, CD$_3$OD): OH and NH resonances were not observed; δ 8.18 (s, 1H), 7.67 (d, J=1.2 Hz, 1H), 7.06-6.98 (m, 2H), 6.68-6.54 (m, 3H), 4.38 (s, 2H).

Step 7: 8-(3-Hydroxyphenyl)-7-(4-iodophenyl)-7,8-dihydropyrano[3,2-e]indazol-9(3H)-one

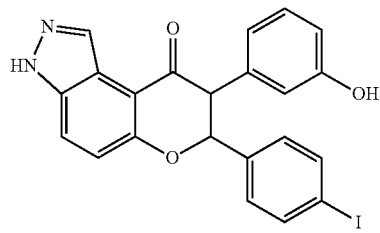

A mixture of 1-(5-hydroxy-1H-indazol-4-yl)-2-(3-hydroxyphenyl)ethanone (1.32 g, 5.0 mmol), 4-iodobenzaldehyde (1.25 g, 5.5 mol), and piperidine (386 mg, 5.5 mmol) in methanol (80 mL) was heated at 75° C. for 16 h. The reaction mixture was allowed to cool to room temperature, and the resulting precipitate was collected by filtration to give the title compound (1.3 g, 54%) as a yellow solid. $^1$H NMR (400 MHz, DMSO-d$_6$): δ 13.40 (s, 1H), 9.25 (s, 1H), 8.42 (s, 1H), 7.88 (d, J=8.8 Hz, 1H), 7.66 (d, J=8.0 Hz, 2H), 7.25 (d, J=8.0 Hz, 2H), 7.16-7.11 (m, 1H), 7.04-6.96 (m, 1H), 6.62-6.54 (m, 3H), 5.98-5.90 (d, J=12.4 Hz, 1H), 4.62-4.56 (d, J=12.4 Hz, 1H).

Step 8: 8-(3-Hydroxyphenyl)-7-(4-iodophenyl)-9-methyl-3,7,8,9-tetrahydropyrano[3,2-e]indazol-9-ol

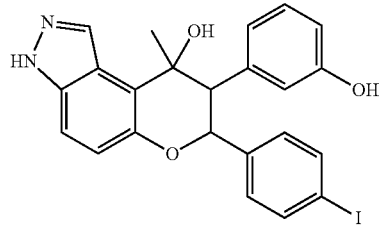

To a solution of 8-(3-hydroxyphenyl)-7-(4-iodophenyl)-7,8-dihydropyrano[3,2-e]indazol-9(3H)-one (830 mg, 1.73 mmol) in dry THF (10 mL) cooled in an ice-bath, was added dropwise a solution of CH$_3$MgBr (2.5 M in THF, 12 mL, 34.4 mmol) over 1 h. The mixture was stirred at 0° C. for 30 min, and then at room temperature for 16 h. The reaction mixture was cooled, and saturated aqueous NH$_4$Cl (100 mL) was added over 30 min. The reaction mixture was extracted with ethyl acetate (3×50 mL), and the combined organic layers were dried (Na$_2$SO$_4$) and concentrated in vacuo to give the title compound (830 mg, 99%) as a yellow solid.

Step 9: 3-(7-(4-Iodophenyl)-9-methyl-3,7-dihydropyrano[3,2-e]indazol-8-yl)phenol

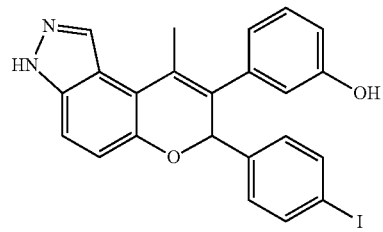

A mixture of 8-(3-hydroxyphenyl)-7-(4-iodophenyl)-9-methyl-3,7,8,9-tetrahydropyrano[3,2-e]indazol-9-ol (850 mg, 1.7 mmol) and 80% acetic acid/H$_2$O (25 mL) was heated at 90° C. for 16 h. The reaction mixture was concentrated in vacuo, and the residue was extracted with ethyl acetate (2×100 mL). The combined organic layers were washed (100 mL saturated NaHCO$_3$, 100 mL brine), dried (Na$_2$SO$_4$), and concentrated. The residue was purified by prep-TLC (DCM: ethyl acetate=3:1) to give the title compound (700 mg, 85%) as a yellow solid. $^1$H NMR (400 MHz, DMSO-d$_6$): δ 13.12 (s, 1H), 9.63 (s, 1H), 8.21 (s, 1H), 7.58 (d, J=7.2 Hz, 2H), 7.34-7.10 (m, 4H), 6.90-6.70 (m, 4H), 6.04 (s, 1H), 2.38 (s, 3H).

Step 10: 7-(4-Iodophenyl)-9-methyl-3-(tetrahydro-2H-pyran-2-yl)-8-(3-((tetrahydro-2H-pyran-2-yl)oxy)phenyl)-3,7-dihydropyrano[3,2-e]indazole

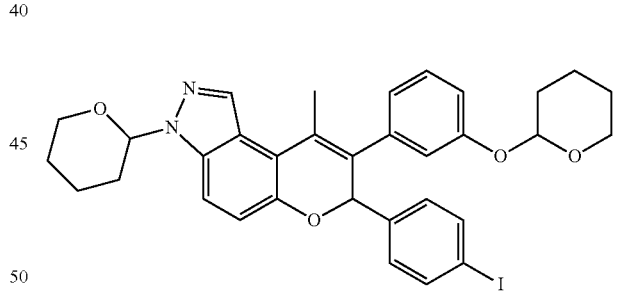

To a solution of 3-(7-(4-iodophenyl)-9-methyl-3,7-dihydropyrano[3,2-e]indazol-8-yl)phenol (150 mg, 0.33 mmol) in DCE (5 mL) was added 3,4-dihydro-2H-pyran (138 mg, 1.65 mmol), followed by the slow addition of pyridinium p-toluene sulfonate (27 mg, 0.1 mmol). The mixture was heated at 75° C. for 16 h, cooled to 0° C. and then quenched with saturated NaHCO$_3$. The mixture was extracted with ethyl acetate (3×20 mL), and the combined organic extracts were dried (Na$_2$SO$_4$) and concentrated in vacuo to afford the title compound (180 mg, 90%) as a brown oil. LCMS: 649.1 [M+H]$^+$.

Intermediate 16

2-(4-Iodophenyl)-4-methyl-7-(tetrahydro-2H-pyran-2-yl)-3-(3-((tetrahydro-2H-pyran-2-yl)oxy)phenyl)-2,7-dihydropyrano[2,3-e]indazole

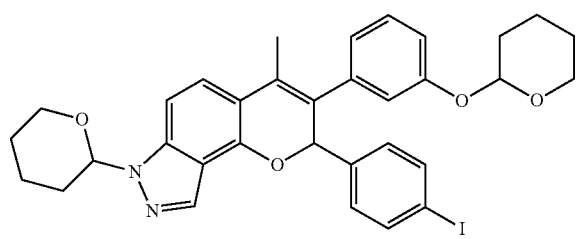

The title compound was synthesized as described in the synthesis of Intermediate 15 (steps 2-10) using 5-bromo-4-methoxy-1H-indazole as starting material. LCMS: 649.0 [M+H]$^+$.

Example 1

3-(3-Hydroxyphenyl)-4-methyl-2-(6-(2-(pyrrolidin-1-yl)ethoxy)pyridin-3-yl)-2H-chromen-6-ol

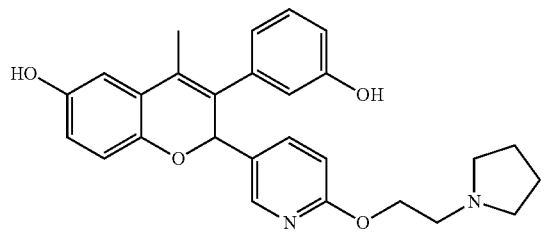

Step 1: 2-(6-(2-(Pyrrolidin-1-yl)ethoxy)pyridin-3-yl)-6-((tetrahydro-2H-pyran-2-yl)oxy)-3-(3-((tetrahydro-2H-pyran-2-yl)oxy)phenyl)chroman-4-one

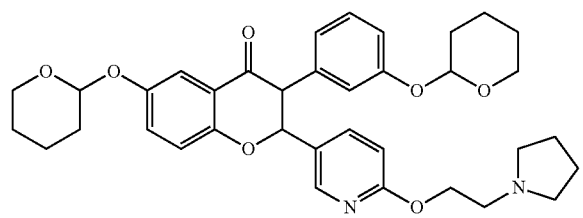

A solution of Intermediate 1 (520 mg, 1.26 mmol), Intermediate 7 (300 mg, 1.36 mmol), piperidine (36 mg, 0.42 mmol), and 1,8-diazabicyclo[5.4.0]undec-7-ene (65 mg, 0.43 mmol) in s-butanol (6 mL) was heated at reflux. Using a Dean-Stark trap, half (3 mL) of the solvent was collected over 1 h, and the reaction was kept at reflux without further concentration for additional 4 h. The solution was cooled to 90° C., i-propanol (6 mL) was added, and the reaction mixture was allowed to cool to room temperature and stirred overnight. The solvent was removed under reduced pressure, and the residue was dissolved in ethyl acetate (100 mL). The solution was washed (2×50 mL H$_2$O, 50 mL brine), dried over Na$_2$SO$_4$, and concentrated under reduced pressure. The crude material was purified on a silica gel column to yield the title compound (535 mg, 69%) as a yellow foam. $^1$H NMR (300 MHz, DMSO-d$_6$): δ 8.05 (m, 1H), 7.84 (dd, J=8.7, 1.9 Hz, 1H), 7.20-7.50 (m, 2H), 7.08 (m, 2H), 6.73 (m, 4H), 5.89 (m, 1H), 5.48 (m, 1H), 5.34 (m, 1H), 4.68 (m, 1H), 4.27 (m, 2H), 3.40-3.80 (m, 4H), 2.71 (t, J=5.7 Hz, 2H), 2.47 (m, 4H), 1.40-1.90 (m, 16H); LCMS: 615.7 [M+H]+.

Step 2: 3-(3-Hydroxyphenyl)-4-methyl-2-(6-(2-(pyrrolidin-1-yl)ethoxy)pyridin-3-yl)-2H-chromen-6-ol

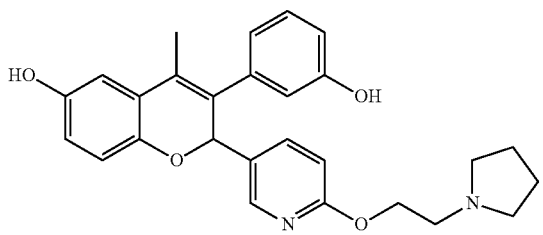

To a solution of 2-(6-(2-(pyrrolidin-1-yl)ethoxy)pyridin-3-yl)-6-((tetrahydro-2H-pyran-2-yl)oxy)-3-(3-((tetrahydro-2H-pyran-2-yl)oxy)phenyl)chroman-4-one (375 mg, 0.61 mmol) in THF (3 mL) at 0° C. was added methyl magnesium chloride (3 M in THF, 0.6 mL, 1.8 mmol). (Note #1) The solution was stirred at 0° C. for 1 h and allowed to warm to room temperature. After stirring overnight at room temperature, the reaction was cooled to 0° C., quenched with saturated ammonium chloride (1.0 mL), and then allowed to warm to room temperature. The reaction was diluted with ethyl acetate (50 mL), washed (2×25 mL saturated. NaHCO$_3$, 25 mL brine), and dried (Na$_2$SO$_4$). The solvent was removed under reduced pressure and the crude material was heated in 80% acetic acid/H$_2$O (10 mL) at 90° C. overnight. The solution was concentrated under reduced pressure and purified by reverse phase HPLC (acetonitrile, H$_2$O, TFA) to yield the desired compound as a TFA salt. The compound was freebased with sodium bicarbonate by extracting with ethyl acetate to give the title compound (120 mg, 44%). (Note #2)$^1$H NMR (300 MHz, DMSO-d$_6$, HCl salt): δ 9.96 (br s, 1H), 9.51 (br s, 1H), 9.04 (br s, 1H), 8.08 (d, J=1.9 Hz, 1H), 7.66 (dd, J=8.7, 1.9 Hz, 1H), 7.16 (t, J=7.6 Hz, 1H), 6.80 (m, 4H), 6.67 (s, 1H), 6.52 (s, 2H), 5.99 (s, 1H), 4.48 (t, J=4.7 Hz, 2H), 3.52 (m, 4H), 3.05 (m, 2H), 2.05 (s, 3H), 1.99 (m, 2H), 1.84 (m, 2H); LCMS: 445.7 [M+H]$^+$.

Note #1: Organo cerium reagent can be substituted for methyl magnesium chloride to synthesize the corresponding tertiary alcohol following the general procedure: Methyl magnesium chloride (1.5 eq., 3M in THF) was added to a suspension of cerium (III) chloride (1.5 eq) in THF at 0° C. The resulting mixture was stirred at 0° C. for 2 h, and a solution of corresponding ketone (1 eq.) in THF was added. The reaction was stirred at 0° C. for an additional 2 h and quenched with methanol. The mixture was diluted with H$_2$O and extracted with ethyl acetate. The combined organic layers were dried over Na$_2$SO$_4$, filtered, concentrated, and purified on a silica gel column to afford the desired tertiary alcohol.

Note #2: The compound can be converted into hydrochloride salt by the following the general method: The compound was suspended in diethyl ether and methanol was added until the solution became clear. Hydrogen chloride in diethyl ether (2N) was added and the solvent was removed under reduced pressure.

Example 2

3-(3-Hydroxyphenyl)-4-methyl-2-(6-((S)-2-((R)-3-methylpyrrolidin-1-yl)propoxy)pyridin-3-yl)-2H-chromen-6-ol

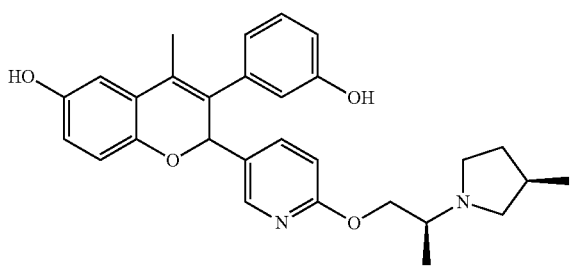

The title compound was synthesized as described in the synthesis of Example 1 using Intermediate 1 and Intermediate 8 as starting materials. $^1$H NMR (300 MHz, DMSO-d$_6$, TFA salt): δ 9.68 (br s, 1H), 9.51 (br s, 1H), 9.04 (br s, 1H), 8.08 (s, 1H), 7.66 (dd, J=8.6, 2.2 Hz, 1H), 7.16 (t, J=7.6 Hz, 1H), 6.75 (m, 4H), 6.67 (s, 1H), 6.52 (m, 2H), 5.99 (s, 1H), 4.38 (m, 2H), 3.72 (m, 1H), 3.55 (m, 1H), 3.45 (m, 1H), 3.31 (m, 1H), 3.01 (m, 1H), 2.75 (m, 1H), 2.27 (m, 1H), 2.05 (s, 3H), 1.54 (m, 1H), 1.31 (2d, J=6.5, 6.5 Hz, 3H), 1.02 (d, J=6.6 Hz, 3H); LCMS: 473.7 [M+H]$^+$.

Example 3

3-(3-Hydroxyphenyl)-4-methyl-2-(5-((S)-2-((R)-3-methylpyrrolidin-1-yl)propoxy)pyrazin-2-yl)-2H-chromen-6-ol

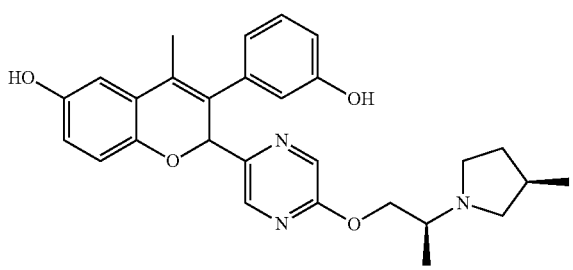

The title compound was synthesized as described in the synthesis of Example 1 using Intermediate 1 and Intermediate 9 as starting materials. $^1$H NMR (300 MHz, CD$_3$OD, TFA salt): OH resonances were not observed; δ 8.23 (d, J=1.2 Hz, 1H), 8.14 (d, J=1.2 Hz, 1H), 7.19-7.15 (m, 1H), 6.85-6.68 (m, 4H), 6.55 (s, 2H), 5.99 (s, 1H), 4.65-4.60 (m, 1H), 4.49-4.43 (m, 1H), 3.71-3.55 (m, 3H), 3.12-3.10 (m, 1H), 2.80 (t, J=11.0 Hz, 1H), 2.55-2.19 (m, 3H), 2.10 (s, 3H), 1.47 (2d, J=6.8, 6.8 Hz, 3H), 1.16 (d, J=6.7 Hz, 3H); LCMS: 474.7 [M+H]$^+$.

Example 4

3-(3-Hydroxyphenyl)-4-methyl-2-(5-(2-(pyrrolidin-1-yl)ethoxy)pyrazin-2-yl)-2H-chromen-6-ol

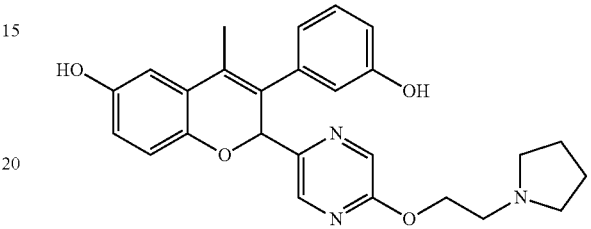

The title compound was prepared as described in the synthesis of Example 1 using Intermediate 1 and Intermediate 10 as starting materials. $^1$H NMR (300 MHz, CD$_3$OD): OH resonances were not observed; δ 8.22 (d, J=1.2 Hz, 1H), 8.14 (d, J=1.2 Hz, 1H), 7.28-7.13 (m, 1H), 6.96-6.64 (m, 4H), 6.59-6.54 (m, 2H), 5.99 (s, 1H), 4.64-4.61 (m, 2H), 3.70-3.55 (m, 4H), 3.18 (m, 2H), 2.10 (s, 3H), 2.17-1.95 (m, 4H). LCMS: 446.7 [M+H]+.

Example 5

3-(3-Hydroxyphenyl)-4-methyl-2-(5-((S)-2-((R)-3-methylpyrrolidin-1-yl)propoxy)pyridin-2-yl)-2H-chromen-6-ol

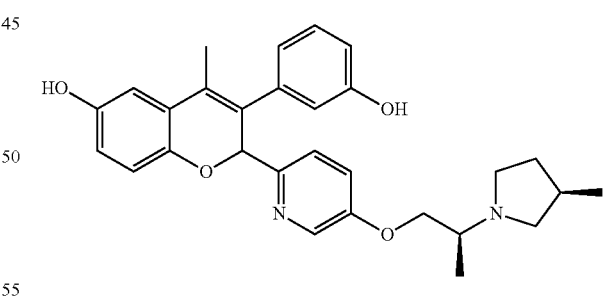

The title compound was synthesized as described in the synthesis of Example 1 using Intermediate 1 and Intermediate 11 as starting materials. $^1$H NMR (300 MHz, CD$_3$OD, TFA salt): OH resonances were not observed; δ 8.27 (s, 1H), 7.58-7.40 (m, 2H), 7.14 (t, J=7.8 Hz, 2H), 6.83-6.54 (m, 5H), 5.94 (s, 1H), 4.40-4.37 (m, 1H), 4.23-4.18 (m, 1H), 3.74-3.58 (m, 3H), 3.16-3.09 (m, 1H), 2.86-2.79 (m, 1H), 2.56-2.27 (m, 3H), 2.11 (s, 3H), 1.50 (2d, J=6.7, 6.7 Hz, 3H), 1.15 (d, J=6.7 Hz, 3H); LCMS: 473.7 [M+H]$^+$.

Example 6

3-(3-Hydroxyphenyl)-4-methyl-2-(5-(2-(pyrrolidin-1-yl)ethoxy)pyridin-2-yl)-2H-chromen-6-ol

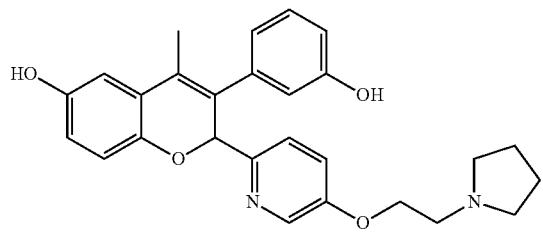

Step 1: 2-(5-Bromopyridin-2-yl)-6-((tetrahydro-2H-pyran-2-yl)oxy)-3-(3-((tetrahydro-2H-pyran-2-yl)oxy)phenyl)chroman-4-one

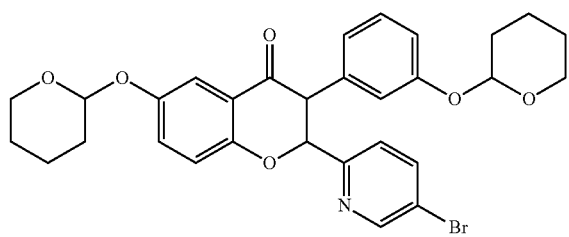

A solution of Intermediate 1 (500 mg, 1.2 mmol), 5-bromopicolinaldehyde (250 mg, 1.1 mmol), piperidine (34 mg, 0.39 mmol), and 1,8-diazabicyclo[5.4.0]undec-7-ene (60 mg, 0.39 mmol) in s-butanol (6 mL) was heated at reflux. Using a Dean-Stark trap, half (3 mL) of the solvent was collected over 1 h, and the reaction was kept at reflux without further concentration for additional 3 h. The solution was cooled to 90° C., i-propanol (6 mL) was added, and the reaction mixture was allowed to cool to room temperature and stirred overnight. The solvent was removed under reduced pressure, and the residue was dissolved in ethyl acetate (300 mL). The solution was washed (water and brine), dried (Na$_2$SO$_4$), filtered and concentrated under reduced pressure. The crude material was purified on a silica gel column to yield the title compound (560 mg, 80%) as off-white foam. LCMS: 580 [M+H]$^+$ Step 2: 5-Bromo-2-(4-methyl-6-((tetrahydro-2H-pyran-2-yl)oxy)-3-(3-((tetrahydro-2H-pyran-2-yl)oxy)phenyl)-2H-chromen-2-yl)pyridine

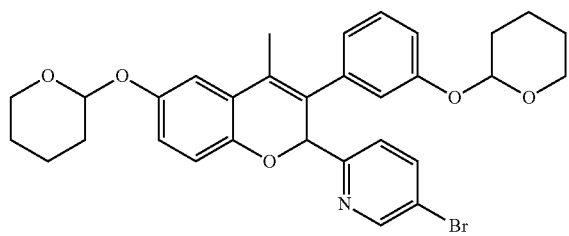

A solution of CH$_3$MgCl (3 M in THF, 0.81 mL, 2.58 mmol) was added dropwise to a solution of 2-(5-bromopyridin-2-yl)-6-((tetrahydro-2H-pyran-2-yl)oxy)-3-(3-((tetrahydro-2H-pyran-2-yl)oxy)phenyl)chroman-4-one (500 mg, 0.85 mmol) in dry THF (5.2 mL) at 0° C. The mixture was allowed to warm to room temperature and stirred for 30 min. The reaction mixture was re-cooled to 0° C., quenched with brine, and then extracted with ethyl acetate (3×100 mL). The combined organic layers were washed (water and then brine), dried (Na$_2$SO$_4$), filtered, and concentrated in vacuo to give crude 2-(5-bromopyridin-2-yl)-4-methyl-6-((tetrahydro-2H-pyran-2-yl)oxy)-3-(3-((tetrahydro-2H-pyran-2-yl)oxy)phenyl)chroman-4-ol. This compound (510 mg, 0.85 mmol) was suspended in 80% acetic acid in water (17 mL) and heated at 90° C. overnight. Upon completion by TLC, the reaction mixture was allowed to cool to room temperature, concentrated in vacuo to give a residue. This residue was dissolved in ethyl acetate, washed (saturated NaHCO$_3$, water, and then brine), dried (Na$_2$SO$_4$), filtered, and concentrated in vacuo. The crude material was purified by silica gel chromatography to give 2-(5-bromopyridin-2-yl)-3-(3-hydroxyphenyl)-4-methyl-2H-chromen-6-ol. Pyridinium p-toluene sulfonate (25 mg, 0.1 mmol) was added to a solution of 2-(5-bromopyridin-2-yl)-3-(3-hydroxyphenyl)-4-methyl-2H-chromen-6-ol (200 mg, 0.49 mmol) and 3,4-dihydro-2H-pyran (200 mg, 2.43 mmol) in DCM (4.9 mL). The mixture was stirred at room temperature overnight, quenched with saturated NaHCO$_3$, and then extracted with ethyl acetate (3×100 mL). The combined organic extracts were washed (water, brine), dried (Na$_2$SO$_4$), filtered, and concentrated in vacuo to afford the title compound (150 mg, 54%). LCMS: 578.4 [M+H]$^+$.

Step 3: 3-(3-Hydroxyphenyl)-4-methyl-2-(5-(2-(pyrrolidin-1-yl)ethoxy)pyridine-2-yl)-2H-chromen-6-ol

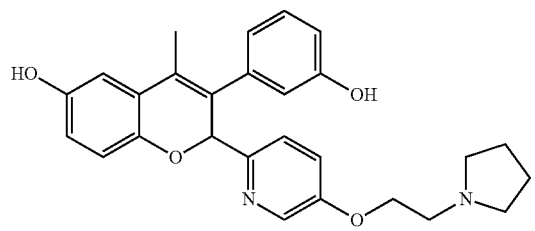

A mixture of 5-bromo-2-(4-methyl-6-((tetrahydro-2H-pyran-2-yl)oxy)-3-(3-((tetrahydro-2H-pyran-2-yl)oxy)phenyl)-2H-chromen-2-yl)pyridine (45 mg, 0.078 mmol), 2-(pyrrolidin-1-yl)ethanol (45 mg, 0.38 mmol), Pd(OAc)$_2$ (5.2 mg, 0.0078 mmol), [1,1'-binaphthalen]-2-yldi-tert-butylphosphine (19 mg, 0.047 mmol), and cesium carbonate (0.12 g, 0.38 mmol) in toluene (0.8 mL) was degassed with three cycles of nitrogen/vacuum. The mixture was heated at 110° C. overnight, allowed to cool to room temperature, quenched with brine, and then extracted with ethyl acetate (3×10 mL). The combined organic extracts were washed (water and then brine), dried (Na$_2$SO$_4$), filtered, and concentrated to give the crude product. This crude product was suspended in 80% acetic acid in water (1.5 mL) and heated at 90° C. for 2 h. The reaction mixture was allowed to cool to room temperature and then purified by a reverse phase HPLC (acetonitrile, H$_2$O, TFA) to afford the title compound (2 mg, 5%) as a TFA salt. $^1$H NMR (300 MHz, CD$_3$OD, TFA salt): OH resonances were not observed; δ 8.26 (s, 1H), 7.54-7.41 (m, 2H), 7.14 (t, J=7.6 Hz, 2H), 6.83-6.54 (m, 5H), 5.94 (s, 1H), 4.37 (t, J=4.7 Hz, 2H), 3.65 (t, J=4.7 Hz, 2H), 3.25-3.15 (m, 4H), 2.10 (s, 3H), 2.18-2.03 (m, 4H); LCMS: 445.6 [M+H]+.

Example 7

3-(3,4-Difluoro-5-hydroxyphenyl)-4-methyl-2-(5-((S)-2-((R)-3-methylpyrrolidin-1-yl)propoxy)pyridin-2-yl)-2H-chromen-6-ol

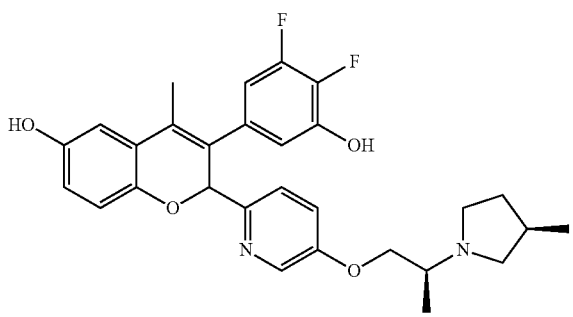

The title compound was synthesized as described in the synthesis of Example 1 using Intermediate 2 and Intermediate 11 as starting materials. 1H NMR (400 MHz, DMSO-d6, HCl salt): δ 10.86 (br, 1H), 10.54 (br, 1H), 9.12 (br, 1H), 8.26 (d, J=2.7 Hz, 1H), 7.39-7.30 (m, 2H), 6.84-6.76 (m, 1H), 6.76-6.74 (m, 1H), 6.68 (d, J=7.4 Hz, 1H), 6.55-6.49 (m, 2H), 5.91 (s, 1H), 4.28 (t, J=5.1 Hz, 2H), 3.75-3.63 (m, 1H), 3.61-3.35 (m, 2H), 3.35-3.07 (m, 1H), 3.06-2.65 (m, 1H), 2.45-2.34 (m, 1H), 2.15-2.02 (m, 1H), 2.00 (s, 3H), 1.61-1.41 (m, 1H), 1.36 (m, 3H), 1.02 (m, 3H); LCMS: 509.1 [M+H]+.

Example 8

3-(4-Hydroxyphenyl)-4-methyl-2-(5-((S)-2-((R)-3-methylpyrrolidin-1-yl)propoxy)pyridin-2-yl)-2H-chromen-6-ol

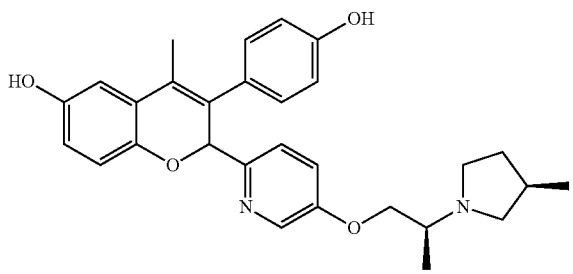

The title compound was synthesized as described in the synthesis of Example 1 using Intermediate 3 and Intermediate 11 as starting materials. 1H NMR (400 MHz, DMSO-d6, HCl salt): OH resonances were not observed; δ 10.67 (br, 1H), 8.25 (d, J=2.9 Hz, 1H), 7.35-7.32 (m, 1H), 7.29 (t, J=8.6 Hz, 1H), 7.09 (d, J=8.6 Hz, 2H), 6.74-6.72 (m, 1H), 6.71 (d, J=8.6 Hz, 2H), 6.50-6.45 (m, 2H), 5.94 (s, 1H), 4.31-4.22 (m, 2H), 3.74-3.63 (m, 1H), 3.56-3.33 (m, 2H), 3.33-3.15 (m, 1H), 3.04-2.65 (m, 1H), 2.44-2.21 (m, 1H), 2.17-2.02 (m, 1H), 2.00 (s, 3H), 1.58-1.40 (m, 1H), 1.34 (m, 3H), 1.02 (m, 3H); LCMS: 473.2 [M+H]+.

Example 9

3-(3-Fluoro-4-hydroxyphenyl)-4-methyl-2-(5-((S)-2-((R)-3-methylpyrrolidin-1-yl)propoxy)pyridin-2-yl)-2H-chromen-6-ol

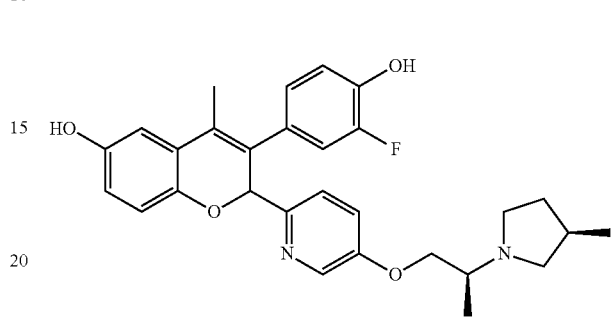

The title compound was synthesized as described in the synthesis of Example 1 using Intermediate 4 and Intermediate 11 as starting materials. 1H NMR (400 MHz, DMSO-d6, HCl salt): δ 10.68 (br, 1H), 10.01 (br, 1H), 8.96 (br, 1H), 8.26 (d, J=2.7 Hz, 1H), 7.36-7.28 (m, 2H), 7.13-7.08 (m, 1H), 6.95-6.88 (m, 2H), 6.75-6.72 (m, 1H), 6.53-6.47 (m, 2H), 5.96 (s, 1H), 4.31-4.21 (m, 2H), 3.74-3.63 (m, 1H), 3.55-3.35 (m, 2H), 3.32-3.07 (m, 1H), 3.06-2.65 (m, 1H), 2.43-2.20 (m, 1H), 2.14-2.04 (m, 1H), 2.01 (s, 3H), 1.66-1.41 (m, 1H), 1.34 (m, 3H), 1.02 (m, 3H); LCMS: 491.1 [M+H]+.

Example 10

3-(2-Fluoro-4-hydroxyphenyl)-4-methyl-2-(5-((S)-2-((R)-3-methylpyrrolidin-1-yl)propoxy)pyridin-2-yl)-2H-chromen-6-ol

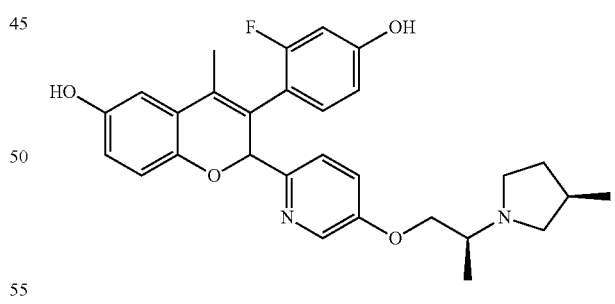

The title compound was synthesized as described in the synthesis of Example 1 using Intermediate 5 and Intermediate 11 as starting materials. 1H NMR (400 MHz, DMSO-d6, HCl salt): δ 10.83 (br, 1H), 10.06 (br, 1H), 9.14 (br, 1H), 8.24 (d, J=2.9 Hz, 1H), 7.37 (dd, J=8.7, 2.9 Hz, 1H), 7.29 (d, J=8.7 Hz, 1H), 7.13-7.04 (m, 1H), 6.75-6.74 (m, 1H), 6.60-6.53 (m, 2H), 6.52-6.50 (m, 2H), 5.87 (s, 1H), 4.34-4.20 (m, 2H), 3.76-3.62 (m, 1H), 3.57-3.34 (m, 2H), 3.34-3.08 (m, 1H), 3.04-2.64 (m, 1H), 2.44-2.20 (m, 1H), 2.14-1.96 (m, 1H), 1.91 (s, 3H), 1.69-1.40 (m, 1H), 1.34 (m, 3H), 1.02 (m, 3H); LCMS: 491.1 [M+H]+.

Example 11

3-(1H-Indazol-6-yl)-4-methyl-2-(4-((S)-2-((R)-3-methylpyrrolidin-1-yl)propoxy)phenyl)-2H-chromen-6-ol

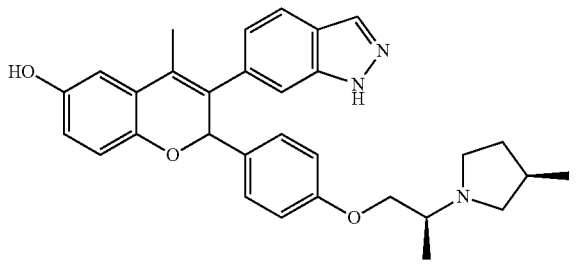

A mixture of Intermediate 12 (200 mg, 0.31 mmol), Intermediate 6 (95 mg, 0.66 mmol), CuI (7 mg, 0.03 mmol), and potassium carbonate (87 mg, 0.63 mmol) in butyronitrile (0.6 mL) was degassed by bubbling nitrogen for 15 min. The reaction mixture was heated at 125° C. for 3 days, allowed to cool to room temperature, and then diluted with ethyl acetate (50 mL). The mixture was washed (25 mL saturated NaHCO$_3$, 25 mL brine), dried (Na$_2$SO$_4$), and concentrated under reduced pressure. The crude material was purified on a silica gel column to yield 6-(4-methyl-2-(4-((S)-2-((R)-3-methylpyrrolidin-1-yl)propoxy)phenyl)-6-((tetrahydro-2H-pyran-2-yl)oxy)-2H-chromen-3-yl)-1-(tetrahydro-2H-pyran-2-yl)-1H-indazole as a white foam (140 mg). This white foam was dissolved in methanol (3 mL) and HCl (2N in ether, 0.3 mL), and the solution was stirred at room temperature 2 days. The solvent was removed under reduced pressure, and the residue was purified by reverse phase HPLC (acetonitrile, H$_2$O, TFA) to yield the title compound as a TFA salt (70 mg, 46%). $^1$H NMR (300 MHz, DMSO-d$_6$, TFA salt): δ 12.93 (br, 1H), 9.89 (br, 1H), 9.03 (br, 1H), 8.04 (d, J=0.9 Hz, 1H), 7.73 (d, J=8.4 Hz, 1H), 7.38 (s, 1H), 7.29 (d, J=8.6 Hz, 2H), 7.05 (dd, J=8.4, 1.2 Hz, 1H), 6.87 (d, J=8.6 Hz, 2H), 6.80-6.77 (m, 1H), 6.55-6.47 (m, 2H), 6.03 (s, 1H), 4.22-4.02 (m, 2H), 3.76-3.60 (m, 1H), 3.60-3.34 (m, 2H), 3.38-2.91 (m, 2H), 2.82-2.62 (m, 1H), 2.80-2.65 (m, 1H), 2.07 (s, 3H), 1.60-1.40 (m, 1H), 1.32 (2d, J=6.7, 6.7 Hz, 3H), 1.02 (2d, J=6.7, 6.7 Hz, 3H); LCMS: 496.1 [M+H]$^+$.

Example 12

3-(1H-Indazol-5-yl)-4-methyl-2-(4-((S)-2-((R)-3-methylpyrrolidin-1-yl)propoxy)phenyl)-2H-chromen-6-ol

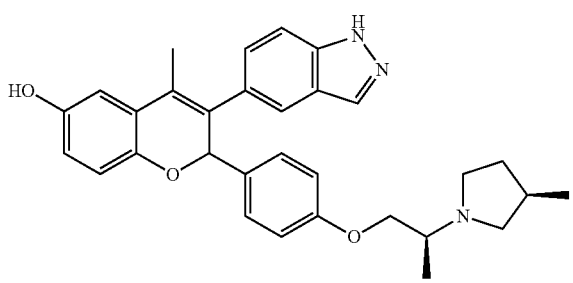

The title compound was synthesized as descried in the synthesis of Example 11 using Intermediate 13 and Intermediate 6 as starting materials. $^1$H NMR (300 MHz, DMSO-d$_6$, HCl salt): δ 13.10 (br, 1H), 10.71 (br, 1H), 8.04 (d, J=0.9 Hz, 1H), 7.66 (s, 1H), 7.51 (d, J=8.6 Hz, 1H), 7.31-7.23 (m, 3H), 6.86 (d, J=8.6 Hz, 2H), 6.78-6.76 (m, 1H), 6.54-6.46 (m, 2H), 6.02 (s, 1H), 5.00 (br, 1H), 4.20-4.10 (m, 2H), 3.71-3.54 (m, 1H), 3.52-3.19 (m, 2H), 3.17-2.90 (m, 1H), 2.77-2.61 (m, 1H), 2.43-2.15 (m, 1H), 2.16-1.92 (m, 1H), 2.06 (s, 3H), 1.61-1.39 (m, 1H), 1.33 (2d, J=6.8, 6.8 Hz, 3H), 1.03 (2d, J=6.9, 6.9 Hz, 3H); LCMS: 496.1 [M+H]$^+$.

Example 13

3-(1H-Indazol-4-yl)-4-methyl-2-(4-((S)-2-((R)-3-methylpyrrolidin-1-yl)propoxy)phenyl)-2H-chromen-6-ol

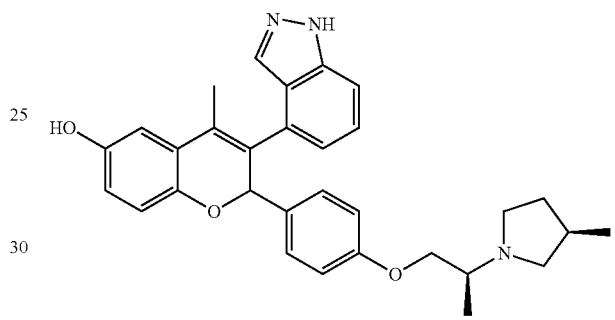

The title compound was synthesized as described in the synthesis of Example 11 using Intermediate 14 and Intermediate 6 as starting materials. $^1$H NMR (300 MHz, DMSO-d$_6$): δ 13.08 (s, 1H), 8.95 (s, 1H), 7.91 (s, 1H), 7.40 (d, J=8.4 Hz, 1H), 7.27 (dd, J=8.4, 7.2 Hz, 1H), 7.20 (d, J=8.4 Hz, 2H), 6.96 (d, J=7.1 Hz, 1H), 6.78-6.74 (m, 1H), 6.70 (d, J=8.4 Hz, 2H), 6.52-6.49 (m, 2H), 5.97 (s, 1H), 3.93-3.81 (m, 1H), 3.71-3.57 (m, 1H), 2.80-2.71 (m, 1H), 2.63-2.50 (m, 2H), 2.13-1.98 (m, 2H), 1.89 (s, 3H), 1.87-1.74 (m, 2H), 1.23-1.07 (m, 1H), 0.99 (d, J=6.4 Hz, 3H), 0.89 (d, J=6.4 Hz, 3H); LCMS: 496.2 [M+H]$^+$.

Example 14

3-(9-Methyl-7-(4-((S)-2-((R)-3-methylpyrrolidin-1-yl)propoxy)phenyl)-3,7-dihydropyrano[3,2-e]indazol-8-yl)phenol

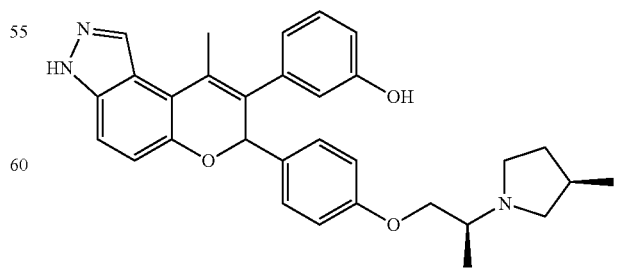

The title compound was synthesized as described in the synthesis of Example 11 using Intermediate 15 and Intermediate 6 as starting materials. ¹H NMR (400 MHz, DMSO-d₆, HCl salt): δ 13.10 (br, 1H), 10.52 (br, 1H), 9.52 (br, 1H), 8.23 (s, 1H), 7.34-7.26 (m, 3H), 7.18 (t, J=7.8 Hz, 1H), 6.87-6.82 (m, 3H), 6.81 (d, J=8.7 Hz, 1H), 6.79-6.76 (m, 1H), 6.70 (dd, J=8.1, 2.4 Hz, 1H), 6.02 (s, 1H), 4.18-4.07 (m, 2H), 3.70-3.58 (m, 1H), 3.53-3.32 (m, 2H), 3.32-3.22 (m, 1H), 3.17-2.91 (m, 1H), 2.74-2.54 (m, 1H), 2.39 (s, 3H), 2.36-1.99 (m, 1H), 1.58-1.34 (m, 1H), 1.31 (2d, J=6.8, 6.8 Hz, 3H), 1.00 (2d, J=6.8, 6.8 Hz, 3H); LCMS: 496.0 [M+H]⁺.

Example 15

3-(4-Methyl-2-(4-((S)-2-((R)-3-methylpyrrolidin-1-yl)propoxy)phenyl)-2,7-dihydropyrano[2,3-e]indazol-3-yl)phenol

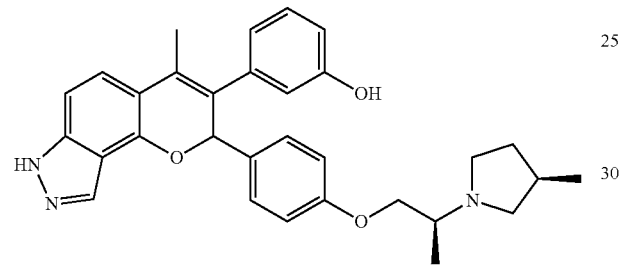

The title compound was synthesized as described in the synthesis of Example 11 using Intermediate 16 and Intermediate 6 as starting materials. ¹H NMR (400 MHz, DMSO-d₆): δ 13.02 (s, 1H), 9.44 (s, 1H), 7.91 (s, 1H), 7.38 (d, J=8.6 Hz, 1H), 7.30 (d, J=8.7 Hz, 2H), 7.17-7.12 (m, 1H), 7.06 (d, J=8.6 Hz, 1H), 6.79 (d, J=8.7 Hz, 2H), 6.74 (d, J=7.7 Hz, 1H), 6.68-6.64 (m, 2H), 6.11 (s, 1H), 3.96-3.89 (m, 1H), 3.75-3.63 (m, 1H), 2.87-2.73 (m, 1H), 2.69-2.55 (m, 2H), 2.15 (s, 3H), 2.11-2.00 (m, 2H), 1.92-1.79 (m, 1H), 1.33-1.12 (m, 2H), 1.02 (d, J=6.4 Hz, 3H), 0.92 (d, J=6.4 Hz, 3H); LCMS: 496.1 [M+H]⁺.

Example 16

2-[4-[2-[3-(Fluoromethyl)azetidin-1-yl]ethoxy]phenyl]-4-methyl-3-(2-methylprop-1-enyl)-2H-chromen-6-ol

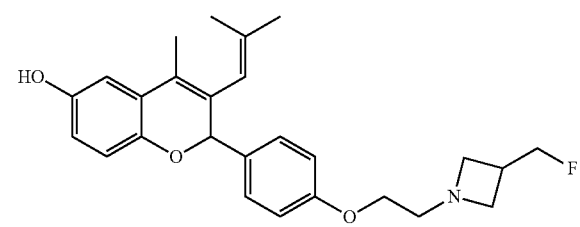

Step 1:
3-Bromo-6-methoxy-4-methyl-2H-chromen-2-one

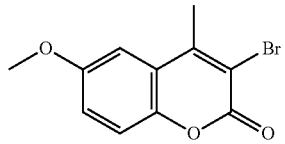

To a mixture of 6-methoxy-4-methyl-chromen-2-one (100 g, 0.53 mol) and NH₄OAc (8.1 g, 0.11 mol) in DMF (500 mL) was added NBS (140 g, 0.79 mol) in an ice-bath. The reaction mixture was stirred at 15° C. for 2 hr. The reaction mixture was filtered, washed with DCM (400 mL×2). The filtrate was concentrated in vacuo. The crude residue was dissolved in chloroform (50 mL) and methyl t-butyl ether (500 mL) was added. The mixture was filtered and the cake was dried to give the crude title compound (105 g, 74%) as a light yellow solid.

Step 2:
3-Bromo-6-hydroxy-4-methyl-2H-chromen-2-one

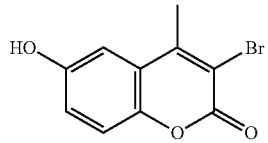

To a solution of 3-bromo-6-methoxy-4-methyl-chromen-2-one (105 g, 0.39 mmol) in DCM (1000 mL) was added BBr₃ (78 mL, 0.78 mmol) dropwise at −78° C. Then the reaction mixture was allowed to warm to room temperature and stirred at 20° C. for 2 hr. The reaction was quenched with MeOH (300 mL) and concentrated in vacuo. The resulting residue was dissolved in DCM and washed with water. The organic layer was dried over anhydrous Na₂SO₄, filtered and concentrated to give the title compound (80 g, 80%) as a light yellow solid which was used in the next step without further purification. ¹H NMR (400 MHz, DMSO-d₆): δ 9.88 (s, 1H), 7.29 (d, J=8.8 Hz, 1H), 7.12-7.07 (m, 2H), 2.55 (s, 3H).

Step 3: 3-Bromo-4-methyl-6-((tetrahydro-2H-pyran-2-yl)oxy)-2H-chromen-2-one

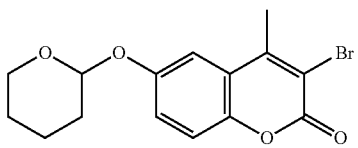

A mixture of 3-bromo-6-hydroxy-4-methyl-chromen-2-one (40 g, 156.8 mmol), pyridinium 4-toluenesulfonate (19.7 g, 78.4 mmol) and dihydropyran (72 mL, 784.0 mmol) in THF (40 mL) was stirred at 80° C. for 2 hr. After cooling to room temperature, the reaction mixture was diluted with water (400 mL) and extracted with EtOAc (400 mL×2). The combined organic layers were dried over anhydrous Na₂SO₄, filtered and concentrated. The residue was purified by silica gel column chromatography (20% EtOAc in petroleum ether) to give the title compound (21 g, 40%) as a yellow solid.

Step 4: 3-Bromo-4-methyl-6-((tetrahydro-2H-pyran-2-yl)oxy)-2H-chromen-2-ol

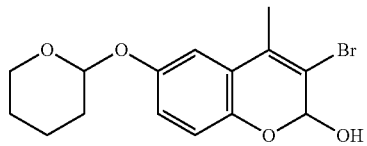

To a solution of crude 3-bromo-4-methyl-6-((tetrahydro-2H-pyran-2-yl)oxy)-2H-chromen-2-one (13 g, 38.33 mmol) in toluene (200 mL) was added DIBAL-H (46 mL, 46 mmol) dropwise at −78° C. The reaction mixture was stirred at −78° C. for 2 hr. The reaction was quenched with 1 N NaOH (10 mL). The mixture was filtered over a short pad of Celite®, washed with MeOH (50 mL×2). The filtrate was concentrated and the crude residue was purified by silica gel column chromatography (20% EtOAc in petroleum ether) to give the title compound (9.5 g, 73%) as a white solid.

Step 5: 2-(3-Bromo-4-(4-(2-(3-(fluoromethyl)azetidin-1-yl)ethoxy)phenyl)-4-hydroxybut-2-en-2-yl)-4-((tetrahydro-2H-pyran-2-yl)oxy) phenol

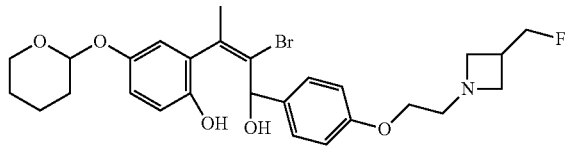

To a solution of 1-[2-(4-bromophenoxy)ethyl]-3-(fluoromethyl)azetidine (21 g, 73.04 mmol) in THF (200 mL) was added n-BuLi (2.5 M in hexanes, 33 mL, 83.47 mmol) at −78° C. The reaction mixture was stirred at −78° C. for 30 min before the addition of 3-bromo-4-methyl-6-tetrahydro-pyran-2-yloxy-2H-chromen-2-ol (8.9 g, 26.08 mmol) in THF (20 mL). The reaction mixture was stirred for another 2 hr before being quenched with water (200 mL). The crude mixture was extracted with EtOAc (200 mL×2). The combined organic layers were dried over Na₂SO₄, filtered and concentrated to give the title compound (26 g) as yellow oil which was used in the next step without further purification.

Step 6: 3-Bromo-2-(4-(2-(3-(fluoromethyl)azetidin-1-yl)ethoxy)phenyl)-4-methyl-2H-chromen-6-ol

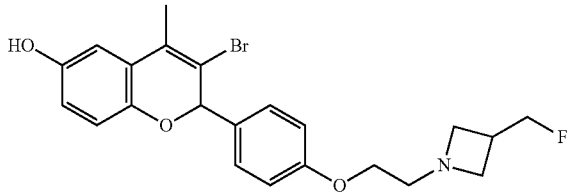

To a solution of 2-(3-bromo-4-(4-(2-(3-(fluoromethyl)azetidin-1-yl)ethoxy)phenyl)-4-hydroxybut-2-en-2-yl)-4-((tetrahydro-2H-pyran-2-yl)oxy)phenol (26 g, 23.62 mmol) in toluene (500 mL) was added concentrated HCl (26 mL, 7.6 mmol) at 0° C. and stirred for 30 minutes. The organic layer was separated. To the aqueous layer was added aq. NaOH (1 N) solution until pH=14. The mixture was extracted with DCM (100 mL×2). Combined organic layers were dried over anhydrous Na₂SO₄, filtered and concentrated in vacuo. The residue was purified by silica gel column chromatography (5% MeOH in DCM) to give the title compound (7.7 g, 66% over two steps) as a cyan solid. ¹H NMR (400 MHz, CD₃OD) δ 7.23 (d, J=8.4 Hz, 2H), 6.82 (d, J=8.8 Hz, 2H), 6.74 (d, J=2.8 Hz, 1H), 6.55-6.47 (m, 2H), 5.72 (s, 1H), 4.53-4.40 (m, 2 H), 3.96 (t, J=5.2 Hz, 2H), 3.51 (t, J=8.0 Hz, 2H), 3.20 (t, J=7.6 Hz, 2H), 2.88-2.81 (m, 3H), 2.26 (s, 3H); LCMS: 448 [M+H]⁺.

Step 7: 2-[4-[2-[3-(Fluoromethyl)azetidin-1-yl]ethoxy]phenyl]-4-methyl-3-(2-methylprop-1-enyl)-2H-chromen-6-ol

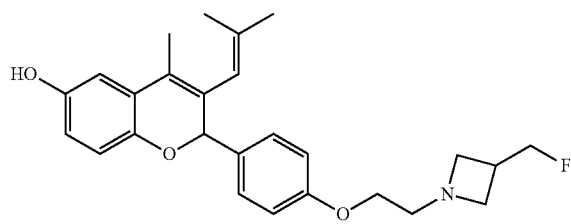

A mixture of 3-bromo-2-[4-[2-[3-(fluoromethyl)azetidin-1-yl]ethoxy]phenyl]-4-methyl-2H-chromen-6-ol (100 mg, 0.22 mmol), 2,2-dimethylethenylboronic acid pinacol ester (61 mg, 0.34 mmol), and K₂CO₃ (62 mg, 0.45 mmol) in DMF (1.5 mL) and water (0.5 mL) was heated at 90° C. for 2 hr. After cooling to room temperature, the reaction mixture was filtered and purified by reverse-phase HPLC (acetonitrile 28-58/0.225% formic acid in water) to give the title compound (52 mg, 55%) as a yellow solid. ¹H NMR (400 MHz, CD₃OD) δ 7.22 (d, J=8.8 Hz, 2H), 6.83 (d, J=8.8 Hz, 2H), 6.71 (d, J=2.4 Hz, 1H), 6.57-6.38 (m, 2H), 5.54 (s, 1H), 5.45 (s, 1H), 4.67-4.41 (m, 2H), 4.25-4.08 (m, 4H), 4.04-3.88 (m, 2H), 3.45 (t, J=4.8 Hz, 2H), 3.24-2.99 (m, 1H), 1.96 (s, 3H), 1.74 (s, 3H), 1.55 (s, 3H). LCMS: 424.3 [M+H]+.

Example 17

2-(4-(2-(3-(Fluoromethyl)azetidin-1-yl)ethoxy)phenyl)-3-isobutyl-4-methyl-2H-chromen-6-ol

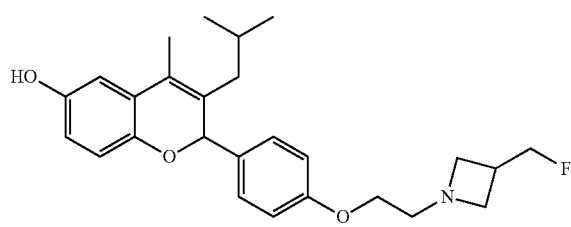

A mixture of 2-[4-[2-[3-(fluoromethyl)azetidin-1-yl]ethoxy]phenyl]-4-methyl-3-(2-methylprop-1-enyl)-2H- chromen-6-ol (100 mg, 0.24 mmol) and 10% palladium on carbon (100 mg, 0.09 mmol) was stirred under a balloon of hydrogen gas at 15° C. for 16 hr. Then the reaction mixture was filtered and concentrated. The residue was lyophilized to give the title compound (65 mg, 65%) as a yellow solid. $^1$H NMR (400 MHz, CD$_3$OD) δ 7.17 (d, J=8.4 Hz, 1H), 6.82-6.67 (m, 3H), 6.50-6.29 (m, 1H), 5.44 (s, 1H), 4.56-4.35 (m, 1H), 3.93 (t, J=5.2 Hz, 1H), 3.49 (t, J=7.6 Hz, 1H), 3.18 (t, J=7.2 Hz, 1H), 2.93-2.73 (m, 2H), 2.30 (m, 1H), 2.08 (s, 3H), 1.81 (m, 1H), 1.66 (m, 1H), 0.94 (m, 6H). LCMS: 448.3 [M+Na]$^+$.

Example 18

3-(2,5-dihydro-1H-pyrrol-3-yl)-2-(4-(2-(3-(fluoromethyl)azetidin-1-yl)ethoxy)phenyl)-4-methyl-2H-chromen-6-ol

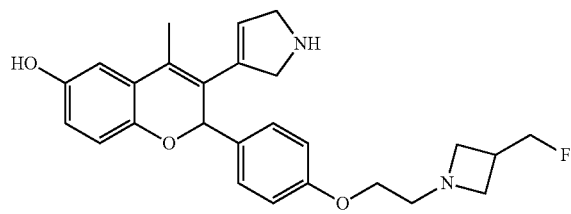

Step 1: tert-Butyl 3-(2-(4-(2-(3-(fluoromethyl)azetidin-1-yl)ethoxy)phenyl)-6-hydroxy-4-methyl-2H-chromen-3-yl)-2,5-dihydro-1H-pyrrole-1-carboxylate

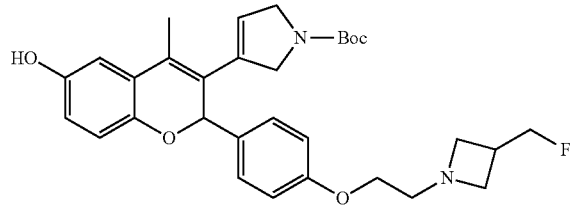

To a solution of 3-bromo-2-[4-[2-[3-(fluoromethyl)azetidin-1-yl]ethoxy]phenyl]-4-methyl-2H-chromen-6-ol (300 mg, 0.67 mmol), tert-butyl 3-(4,4,5,5-tetramethyl-1,3,2-dioxaborolan-2-yl)-2,5-dihydropyrrole-1-carboxylate (237 mg, 0.80 mmol) in DMF (2.3 mL) and water (0.7 mL) were added K$_2$CO$_3$ (277 mg, 2.01 mmol) and bis(triphenylphosphine)palladium(II) dichloride (23 mg, 0.03 mmol). The mixture was stirred at 90° C. for 2 hr. After cooling to room temperature, the reaction mixture was concentrated and the residue was purified by column chromatography on silica gel eluted with 0-5% MeOH in DCM to give the title compound (300 mg, 84%) as a light yellow solid.

Step 2: 3-(2,5-dihydro-1H-pyrrol-3-yl)-2-(4-(2-(3-(fluoromethyl)azetidin-1-yl)ethoxy)phenyl)-4-methyl-2H-chromen-6-ol

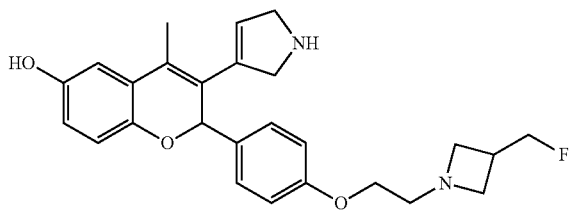

To a solution of tert-butyl 3-[2-[4-[2-[3-(fluoromethyl)azetidin-1-yl]ethoxy]phenyl]-6-hydroxy-4-methyl-2H-chromen-3-yl]-2,5-dihydropyrrole-1-carboxylate (100 mg, 0.19 mmol) in DCM (1.5 mL) was added TFA (0.42 mL, 5.59 mmol) at 15° C. and the mixture was stirred at 15° C. for 1 hr. After concentration under reduced pressure, the resulting residue was purified by reverse-phase HPLC (acetonitrile 2-32/0.2% FA in water) to give the title compound (31 mg, 37%) as a light yellow solid. $^1$H NMR (400 MHz, CD$_3$OD) δ 8.45 (s, 2H), 7.27 (d, J=8.4 Hz, 2H), 6.87 (d, J=8.4 Hz, 2H), 6.80 (d, J=2.4 Hz, 1H), 6.53 (dd, J=8.8, 2.4 Hz, 1H), 6.46 (d, J=8.8 Hz, 1H), 5.84 (s, 1H), 5.70 (s, 1H), 4.53 (dd, J=47.2, 4.0 Hz, 1H), 4.25-3.92 (m, 10H), 3.50-3.42 (m, 2H), 3.23-3.06 (m, 1H), 2.24 (s, 3H). LCMS: 434.3 [M+H]$^+$.

Example 19

1-(3-(2-(4-(2-(3-(Fluoromethyl)azetidin-1-yl)ethoxy)phenyl)-6-hydroxy-4-methyl-2H-chromen-3-yl)pyrrolidin-1-yl)ethanone

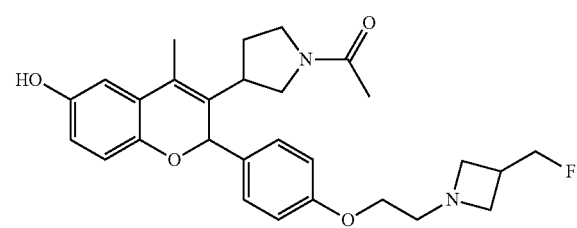

Step 1: 3-(1-Acetyl-2,5-dihydro-1H-pyrrol-3-yl)-2-(4-(2-(3-(fluoromethyl)azetidin-1-yl)ethoxy)phenyl)-4-methyl-2H-chromen-6-yl acetate

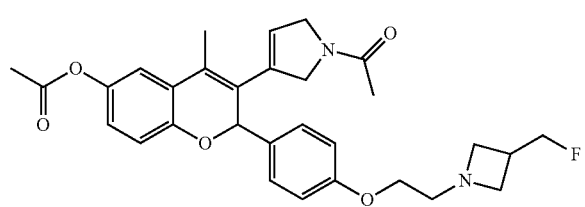

To a solution of 3-(2, 5-dihydro-1H-pyrrol-3-yl)-2-[4-[2-[3-(fluoromethyl)azetidin-1-yl]ethoxy]phenyl]-4-methyl- 2H-chromen-6-ol (162 mg, 0.37 mmol) in DCM (3 mL) was added pyridine (0.24 mL, 2.97 mmol), followed by the addition of acetic anhydride (0.11 mL, 1.11 mmol) at 15° C. The reaction mixture was stirred for 6 hr before being concentrated, and the residue was purified by flash column chromatography on silica gel, eluting with 0-10% MeOH in DCM to give the title compound (120 mg, 62%) as a light yellow solid.

Step 2: 3-(1-Acetylpyrrolidin-3-yl)-2-(4-(2-(3-(fluoromethyl)azetidin-1-yl)ethoxy)phenyl)-4-methyl-2H-chromen-6-yl acetate

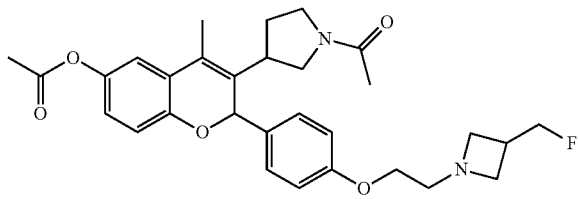

To a solution of [3-(1-acetyl-2,5-dihydropyrrol-3-yl)-2-[4-[2-[3-(fluoromethyl)azetidin-1-yl]ethoxy]phenyl]-4-methyl-2H-chromen-6-yl] acetate (70 mg, 0.13 mmol) in MeOH (2 mL) was added 10% palladium on carbon (72 mg, 0.07 mmol) and the reaction mixture was stirred at 10° C. for 16 h under hydrogen atmosphere (15 psi). The mixture was filtered and the filtrate was concentrated to give crude product (70 mg) as a light yellow solid.

Step 3: 1-(3-(2-(4-(2-(3-(Fluoromethyl)azetidin-1-yl)ethoxy)phenyl)-6-hydroxy-4-methyl-2H-chromen-3-yl)pyrrolidin-1-yl)ethanone

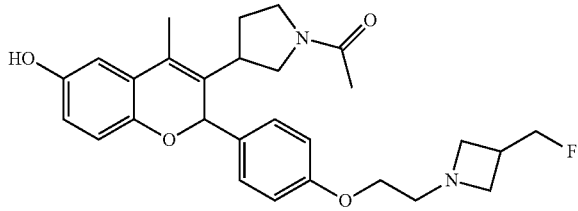

To a solution of [3-(1-acetylpyrrolidin-3-yl)-2-[4-[2-[3-(fluoromethyl)azetidin-1-yl]ethoxy]phenyl]-4-methyl-2H-chromen-6-yl] acetate (50 mg, 0.10 mmol) in MeOH (2 mL) was added K$_2$CO$_3$ (66 mg, 0.48 mmol) and the mixture was stirred at 15° C. for 16 hr. The reaction mixture was filtered and the filtrate was concentrated under vacuo. The resulting residue was purified by reverse-phase HPLC (acetonitrile 10-40%/0.2% formic acid in water) to give the title compound (28.6 mg, 61%) as a light yellow solid. $^1$H NMR (400 MHz, CD$_3$OD) δ 8.47 (s, 1H), 7.29-7.20 (m, 2H), 6.88-6.80 (m, 2H), 6.77-6.73 (m, 1H), 6.46-6.41 (m, 1H), 6.38, 6.36 (2s, 1H), 5.63 (s, 1H), 4.61-4.43 (m, 2H), 4.14-3.97 (m, 4H), 3.91-3.75 (m, 2H), 3.71-3.44 (m, 3H), 3.41-3.32 (m, 4H), 3.15-2.68 (m, 1H), 2.29-2.06 (m, 5H), 1.98 (s, 2H), 1.76 (s, 1H). LCMS: 481.3 [M+H]$^+$.

Example 20

1-(3-(2-(4-(2-(3-(Fluoromethyl)azetidin-1-yl)ethoxy)phenyl)-6-hydroxy-4-methyl-2H-chromen-3-yl)-2,5-dihydro-1H-pyrrol-1-yl)ethanone

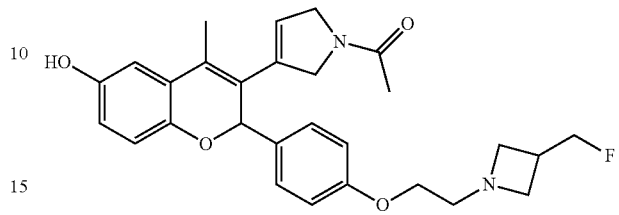

To a solution of [3-(1-acetyl-2,5-dihydropyrrol-3-yl)-2-[4-[2-[3-(fluoromethyl)azetidin-1-yl]ethoxy]phenyl]-4-methyl-2H-chromen-6-yl] acetate (50 mg, 0.10 mmol) in MeOH (2 mL) was added K$_2$CO$_3$ (66 mg, 0.48 mmol) and the mixture was stirred at 15° C. for 16 hr. The reaction mixture was filtered and the filtrate was concentrated under vacuo. The resulting residue was purified by reverse-phase HPLC (acetonitrile 21-51%/0.2% formic acid in water) to give the title compound (5 mg, 10%) as green solid. $^1$H NMR (400 MHz, CD$_3$OD) δ 8.48 (s, 1H), 7.33-7.20 (m, 2H), 6.90-6.82 (m, 2H), 6.78 (d, J=2.0 Hz, 1H), 6.55-6.40 (m, 2H), 5.84-5.76 (m, 1H), 5.73-5.65 (m, 1H), 4.55 (dd, J=47.6, 3.6 Hz, 2H), 4.45-4.07 (m, 8H), 4.04-3.91 (m, 2H), 3.50-3.40 (m, 2H), 3.23-3.02 (m, 1H), 2.23 (s, 3H), 2.03, 3.02 (2s, 3H). LCMS: 479.3 [M+H]$^+$.

Example 21

2-(4-(2-(3-(Fluoromethyl)azetidin-1-yl)ethoxy)phenyl)-3-(4-hydroxycyclohex-1-en-1-yl)-4-methyl-2H-chromen-6-ol

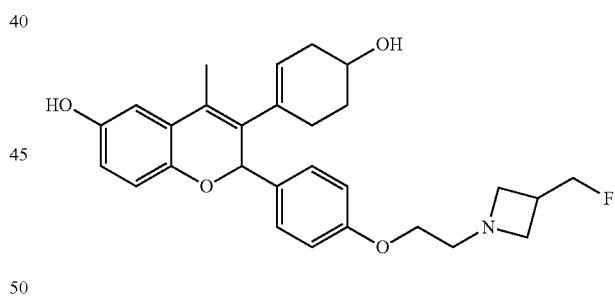

Step 1: 4-(2-(4-(2-(3-(Fluoromethyl)azetidin-1-yl)ethoxy)phenyl)-6-hydroxy-4-methyl-2H-chromen-3-yl)cyclohex-3-enone

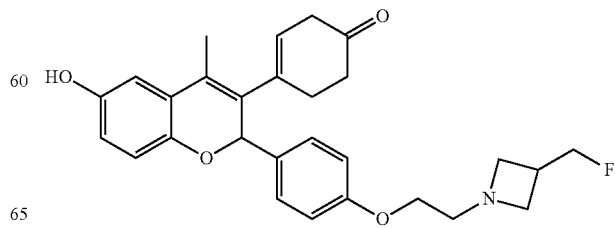

To a solution of 3-(1,4-dioxaspiro[4.5]dec-7-en-8-yl)-2-[4-[2-[3-(fluoromethyl)azetidin-1-yl]ethoxy]phenyl]-4-methyl-2H-chromen-6-ol (100 mg, 0.20 mmol) in DCM (3 mL) was added TFA (1 mL, 0.20 mmol) under 0° C. The reaction mixture was stirred for 2 hr. The mixture was diluted with DCM (50 mL), quenched by solid NaHCO$_3$, and then extracted by DCM (30 mL×3). The combined organic layers were dried by Na$_2$SO$_4$, and concentrated to give the crude title compound (90 mg) as a dark solid which was used in the next step directly.

Step 2: 2-(4-(2-(3-(Fluoromethyl)azetidin-1-yl)ethoxy)phenyl)-3-(4-hydroxycyclohex-1-en-1-yl)-4-methyl-2H-chromen-6-ol

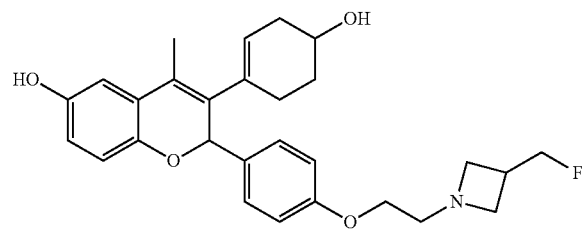

To a solution of 4-[2-[4-[2-[3-(fluoromethyl)azetidin-1-yl]ethoxy]phenyl]-6-hydroxy-4-methyl-2H-chromen-3-yl]cyclohex-3-en-1-one (90 mg, 0.19 mmol) in MeOH (2.5 mL) was added NaBH$_4$ (7 mg, 0.19 mmol). The reaction mixture was stirred at 16° C. for 16 hr. The mixture was concentrated and the resulting residue was purified by reverse-phase HPLC (acetonitrile 28-58%/0.1% formic acid in water) to give the title compound (16 mg, 17%) as a white solid (formic acid salt). $^1$H NMR (400 MHz, CD$_3$OD) δ 8.52 (s, 1H), 7.25 (d, J=8.0 Hz, 2H), 6.85 (d, J=7.2 Hz, 2H), 6.73 (s, 1H), 6.50-6.42 (m, 2H), 5.57 (m, 1H), 5.38 (m, 1H), 4.55 (dd, J=47.2 Hz, 3.6 Hz, 2H), 4.12-4.08 (m, 4H), 3.87-3.81 (m, 3H), 3.35-3.31 (m, 2H), 3.15-3.08 (m, 1H), 2.24-1.80 (m, 9H). LCMS: 466.3 [M+H]$^+$.

Example 22

2-{4-[2-(3-Fluoromethyl-azetidin-1-yl)-ethoxy]-phenyl}-4-methyl-3-(3-methyl-5-cyano-pyridin-2-yl)-2H-chromen-6-ol

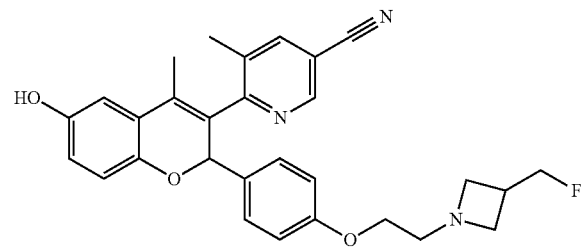

Step 1: 2-{4-[2-(3-Fluoromethyl-azetidin-1-yl)-ethoxy]-phenyl}-4-methyl-3-(4,4,5,5-tetramethyl-[1,3,2]dioxaborolan-2-yl)-2H-chromen-6-ol

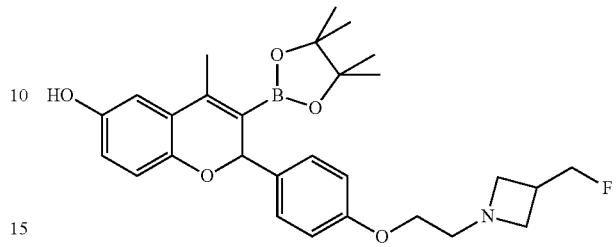

A solution of 3-bromo-2-{4-[2-(3-fluoromethyl-azetidin-1-yl)-ethoxy]-phenyl}-4-methyl-2H-chromen-6-ol (1.0 g, 2.23 mmol) in dimethyl sulfoxide (5 mL) was added to a suspension of bis(pinacolato)diborane (703 mg, 2.77 mmol), potassium acetate (671 mg, 6.84 mmol) and bis(triphenylphosphine)palladium (II) dichloride (93 mg, 0.11 mmol) in dimethyl sulfoxide (5 mL) under argon in a sealed vial. The resulting mixture was heated at 80° C. for 18 hr. The reaction mixture was allowed to cool to ambient temperature. Solids were removed by filtration and the filtrate was purified using a 450 g Interchim Puriflash C18 HP 15 um cartridge eluting with 10-98% acetonitrile in water with 0.1% formic acid. Appropriate fractions were combined and concentrated in vacuo. The residue was dissolved in 2% methanol in dichloromethane (70 mL) and washed with a saturated sodium hydrogen carbonate solution. The organic layer was separated and concentrated in vacuo to afford the title compound as a purple glass (330 mg, 30%). LCMS: 496.5 [M+H]$^+$.

Step 2: 2-{4-[2-(3-Fluoromethyl-azetidin-1-yl)-ethoxy]-phenyl}-4-methyl-3-(3-methyl-5-cyano-pyridin-2-yl)-2H-chromen-6-ol

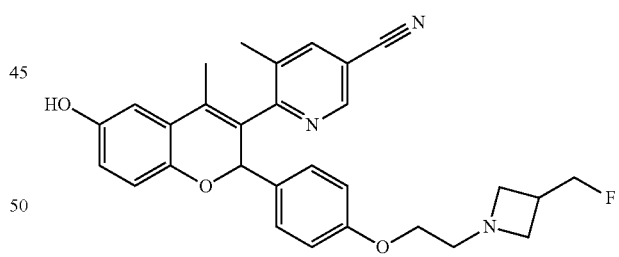

A suspension of 2-{4-[2-(3-fluoromethyl-azetidin-1-yl)-ethoxy]-phenyl}-4-methyl-3-(4,4,5,5-tetramethyl-[1,3,2]dioxaborolan-2-yl)-2H-chromen-6-ol (82.5 mg, 0.17 mmol), 2-bromo-3-methyl-5-cyano-pyridine (50 mg, 0.25 mmol), potassium carbonate (46 mg, 0.33 mmol) and bis(triphenylphosphine)palladium (II) dichloride (12 mg, 0.017 mmol) in N,N-dimethylformamide (3 mL) and water (1 mL) was heated at 90° C. in a sealed tube under argon for 2 hr. The reaction mixture was allowed to cool to room temperature and loaded onto a 10 g SCX-2 cartridge. The cartridge was washed with methanol and the crude product eluted with 2 M ammonia in methanol. The eluent was concentrated in vacuo and the resultant residue was purified by reverse-phase HPLC (XSELECT CSH Prep C18 5 um OBD, 19×250 mm, mobile phase: acetonitrile in water gradient 10% to 98%). Appropriate fractions were combined and evaporated and the residue obtained was further purified by silica gel chromatography (Phenomenex Luna Si 5 um, 21.4×250 mm steel column, mobile phase: 5% of 2 M ammonia in methanol solution in dichloromethane). Appropriate fractions were combined and evaporated to afford the title compound as a beige glass (26.8 mg, 33%). $^1$H NMR (300 MHz, DMSO-$d_6$): δ 9.04 (s, 1H), 8.86 (s, 1H), 8.17 (s, 1H), 7.15 (broad d, 1H), 6.78 (s, 1H), 6.73 (d, J=8.8 Hz, 2H), 6.59 (m, 2H), 5.93 (s, 1H), 4.54 (d, J=6.1 Hz, 1H), 4.42 (d, J=6.1 Hz, 1H), 3.82 (t, J=5.6 Hz, 2H), 3.27 (dt, J=1.2 Hz, J=7.5 Hz, 2H), 2.95 (t, J=6.8 Hz, 2H), 2.76-2.68 (m, 1H), 2.65 (t, J=5.8 Hz, 2H), 2.15 (broad s, 3H), 1.80 (s, 3H). LCMS: 486.2 [M+H]$^+$.

Examples 23-52 were prepared using analogous procedures as described above

Example 53

3×ERE MCF-7 Reporter Assay

MCF7 cells were maintained in RPMI 1640 supplemented with 10% FCS. Transcriptional assays were performed by seeding 100 μL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 300 ng 3×ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 μL of compound plus RPMI 1640 supplemented with charcoal stripped serum was added to the cells. For ER antagonist assays, the compounds were serially diluted and 50 μL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM (MgCO$_3$)$_4$Mg(OH)$_2$.5H$_2$O, 2.67 mM MgSO$_4$, 33.3 mM DTT, 270 μM Coenzyme A, 470 μM luciferin, 53 μM ATP). Renilla luciferase was measured following the addition of 40 μL colelenterazine buffer (1.1 M NaCl, 2.2 mM Na$_2$EDTA, 0.22 M KxPO$_4$ (pH 5.1), 0.44 mg/mL BSA, 1.3 mM NaN$_3$, 1.43 μM coelenterazine, final pH adjusted to 5.0).

Example 54

Breast Cancer Cell Viability Assays

MCF-7 cells were adjusted to a concentration of 40,000 cells per mL in RPMI containing 10% FBS and 20 mM HEPES. 16 microliters of the cell suspension (640 cells) was added to each well of a 384 well plate, and the cells were incubated overnight to allow the cells to adhere. The following day a 10 point, serial 1:5 dilution of each compound was added to the cells in 16 μL at a final concentration ranging from 10-0.00000 μM. After 5 days of compound exposure, 16 μL of CellTiter-GLo (Promega, Madison Wis.) was added to the cells, and the relative luminescence units (RLUs) of each well were determined. CellTiter-Glo added to 32 μL of medium without cells was used to obtain a background value. Table 2 shows the percent viability of each sample was determined as follows: (RLU sample−RLU background/RLU untreated cells−RLU background)× 100=% viability.

Viability effects in additional ER+ breast cancer cell lines, including BT474, CAMA1, MDA-MB-361, ZR-75-1, T47D can be profiled in assays similar to Example 57.

TABLE 2

Breast Cancer Cell Viability Assay

| Example | MCF7 viab IC$_{50}$ (nM) | MCF7 viab max response |
|---|---|---|
| 1 | 0.18 | 53.6 |
| 2 | 0.13 | 56.9 |
| 3 | 0.66 | 61.1 |
| 4 | 0.36 | 49.5 |
| 5 | 1.23 | 64.2 |
| 6 | 7.08 | 56.9 |
| 7 | 1.29 | 72.1 |
| 8 | 1.36 | 69.3 |
| 9 | 1.03 | 71.6 |
| 10 | 0.74 | 70.9 |
| 11 | 17.00 | 55.8 |
| 12 | 2.56 | 60.1 |
| 13 | 0.90 | 65.9 |
| 14 | 0.83 | 62.3 |
| 15 | 0.46 | 65.6 |
| tamoxifen | 380 | 49.5 |
| fulvestrant | 0.56 | 74.6 |

Example 55

ER-α in Cell Western Assay

MCF7 cells were trypsinized and washed twice in Phenol Red Free RPMI containing 5% Charcoal Dextran Stripped serum with 20 mM HEPES and NEAA, then adjusted to a concentration of 200,000 cells per mL with the same medium. Next, 16 μL of the cell suspension (3200 cells) was added to each well of a poly-D-lysine coated 384 well plate, and the cells were incubated at 37° C. over 4 days to allow the cells to adhere and grow. On day 4, a ten point, serial 1:5 dilution of each compound was added to the cells in 16 μL at a final concentration ranging from 10$^{-5}$M to 5.12×10$^{-12}$M or 10$^{-6}$M to 5.12×10$^{-13}$M for fulvestrant. At 4 hours post compound addition, the cells were fixed by adding 16 μL of 30% formalin to the 32 μL of cells and compound (10% formalin final concentration) for 20 minutes. Cells were then washed twice with PBS Tween 0.1% and then permeabilized in PBS 0.1% Triton (50 μl/well) for additional 15 minutes. The PBS 0.1% triton was decanted, and the cells were washed: LI-COR blocking buffer (50 μL/well) was added, the plate was spun at 3000 rpm, and then the blocking buffer was decanted. Additional LI-COR blocking buffer (50 μL/well) was added, and the cells were incubated overnight at 4° C. The blocking buffer was decanted, and the cells were incubated overnight at 4° C. with SP1 (Thermo Scientific) anti-ER rabbit monoclonal antibody diluted 1:1000 in LI-COR blocking buffer/0.1% Tween-20. Wells which were treated with blocking buffer with Tween but no antibody were used as a background control. Wells were washed twice with PBS Tween 0.1% to remove free SP1 antibodies, and the cells were incubated at room temp for 60-90 minutes in LI-COR goat anti-rabbit IRDye™ 800CW (1:1000) and DRAQ5 DNA dye (1:10000 of 5 mM stock solution) diluted in LI-COR blocking buffer containing 0.1% Tween-20 and 0.01% SDS. Cells were then washed with 0.1% Tween-20/PBS three times. Plates were scanned on a LI-COR Odyssey infrared imaging system. Integrated intensities in the 800 nm channel and 700 nm channel were measured to determine levels of ER-α and DNA respectively. Percent ER levels were determined as follows:

(Integrated intensity 800 nM sample/integrated intensity 700 nm sample)/(Integrated intensity 800 nm untreated cells/integrated intensity 700 nm untreated cells)×100=% ER levels.

Effects on steady state levels of ER-α in additional ER+ breast cancer cell lines, including BT474, CAMA1, MDA-MB-361, ZR-75-1, T47D can be profiled in assays similar to Example 54.

TABLE 3

ER-α In Cell Western Assay

| Example | ICW (SP1) $IC_{50}$ (nM) | ICW (SP1) max response |
|---|---|---|
| 1 | 0.21 | 65.9 |
| 2 | 0.21 | 76.1 |
| 3 | 0.41 | 83.3 |
| 4 | 0.56 | 70.1 |
| 5 | 0.71 | 86.7 |
| 6 | 11.10 | 69.9 |
| 7 | 0.39 | 87.1 |
| 8 | 0.35 | 85.9 |
| 9 | 0.29 | 88.0 |
| 10 | 0.21 | 83.4 |
| 11 | 3.48 | 74.1 |
| 12 | 0.45 | 74.8 |
| 13 | 0.23 | 85.1 |
| 14 | 0.74 | 77.8 |
| 15 | 0.27 | 79.5 |
| tamoxifen | 26 | 58.8 |
| fulvestrant | 0.39 | 93.6 |

Example 56

Breast Cancer Cell ERa High Content Fluorescence Imaging Assay

MCF7 breast cancer cells were seeded on day 1 at a density of 10,000 cells per well in 384 well poly-lysine coated tissue culture plate (Greiner # T-3101-4), in 50 uL/well RPMI (phenol red free), 10% FBS (Charcoal stripped), containing L-glutamine. On day 2, compounds were serially diluted in DMSO spanning the concentrations 100 μM to 0.2 nM, in a Labcyte Echo Qualified 384-well polypropylene plate (P-05525). DMSO and 5 uM Fulvestrant (control compound) were added to designated wells. Compounds and controls were dispensed into the cell culture plate, using a Labcyte Echo acoustic dispenser (the final dispensed volume of each control and each compound was 50 nl and the final DMSO concentration was 0.1% v/v), ultimately producing a concentration range from 100 nM to 0.2 pM for serially diluted compounds and a concentration of 5 nM for the control compound Fulvestrant. Cell plates were incubated at 37° C., for 4 hours. Fixation and permeabilization were carried out using a Biotek EL406 plate washer and dispenser as follows. Cells were fixed by addition of 15 uL of 16% paraformaldehyde (Electron Microscopy Sciences #15710-S) directly to the 50 uL cell culture medium in each well using the peristaltic pump 5 uL cassette on a Biotek EL406 (final concentration of formaldehyde was 3.7% w/v). Samples were incubated 30 minutes. Well contents was aspirated and 50 uL/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 uL/well of PBS. Immunofluorescence staining of estrogen receptor alpha (ESR1) was carried out using a Biotek EL406 plate washer and dispenser as follows. The well supernatant was aspirated from the wells and 25 uL/well of anti-ESR1 mAb (F10) (Santa Cruz sc-8002) diluted 1:1000 in Antibody Dilution Buffer was dispensed. Samples were incubated for 2 hours at room temperature. Samples were washed 4 times with 100 uL/well of PBS. 25 uL/well of secondary antibody solution (Alexafluor 488 conjugate anti-mouse IgG (LifeTechnologies #A21202) diluted 1:1000 and Hoechst 33342 1 ug/ml diluted in Antibody Dilution Buffer) were dispensed into each well. Samples were incubated for 2 hours at room temperature. Samples were washed 3 times with 100 uL/well of PBS using a Biotek EL406. Quantitative fluorescence imaging of ESR1 was carried out using a Cellomics Arrayscan V (Thermo). Fluorescence images of the samples (Channel 1: XF53 Hoechst (DNA stain); Channel 2: XF53 FITC (ESR1 stain)) were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using Genedata Screener Software, with DMSO and 5 nM Fulvestrant treated samples being used to define the 0% and 100% changes in ESR1. The "Robust Fit" method was used to define the inflexion point of curve ($EC_{50}$) and the plateau of the maximal effect (Sinf).

TABLE 4

ER-alpha MCF7 Assay

| Example | ER-alpha MCF7 $EC_{50}$ (nM) | ER-alpha MCF7 Sinf (%) |
|---|---|---|
| 16 | 0.73 | 93.9 |
| 17 | 0.215 | 93.9 |
| 18 | 29.1 | 90.0 |
| 19 | 30.0 | 80 |
| 20 | 8.3 | 93.7 |
| 21 | 0.17 | 98.7 |
| 22 | 2.3 | 97.4 |
| 23 | 0.46 | 96.3 |
| 24 |  | 97.7 |
| 25 | 72.4 | 50 |
| 26 | 0.14 | 97.1 |
| 27 | 0.24 | 102 |
| 28 | 0.16 | 99.4 |
| 29 | 0.94 | 98.9 |
| 30 | 0.68 | 97.9 |
| 31 | 16 | 85.9 |
| 32 | 0.006 | 99.4 |
| 33 | 0.041 | 96.4 |
| 34 | 0.12 | 97.5 |
| 35 | 0.038 | 98.5 |
| 36 | 0.12 | 97.5 |
| 37 | 0.095 | 99.2 |
| 38 | 2.8 | 90.3 |
| 39 | 0.067 | 95.4 |
| 40 | 0.12 | 96 |
| 41 | 1.6 | 98.9 |
| 42 | 0.97 | 95.2 |

TABLE 4-continued

ER-alpha MCF7 Assay

| Example | ER-alpha MCF7 EC$_{50}$ (nM) | ER-alpha MCF7 Sinf (%) |
|---|---|---|
| 43 | 0.31 | 97.3 |
| 44 | 1.6 | 91.8 |
| 45 | 2.4 | 96.6 |
| 46 | 0.15 | 98.3 |
| 47 | 0.017 | 95.4 |
| 48 | 47 | 75 |
| 49 | 6.4 | 83.1 |
| 50 | 0.077 | 99.4 |
| 51 | 0.84 | 94.7 |
| 52 | 2.7 | 97.3 |

Example 57

ERa Co-activator Peptide Antagonist Assay

Test compounds were prepared at 1 mM in DMSO and serially diluted in a 12 point, 1 to 3-fold titration using a Biomek FX in 384 well clear V-bottom polypropylene plates (Greiner cat #781280). A 3× compound intermediate dilution was prepared by mixing 1 mL, of each concentration of the compound serial dilution with 32.3 mL of TR-FRET Coregulator Buffer E (Life Technologies PV4540). 2 mL of the 3× compound intermediate dilution was transferred to a 1536-well (Aurora Biotechnologies MaKO 1536 Black Plate, #00028905) using a Biomek FX. A Beckman Coulter Bioraptr Dispenser was used to dispense: 2 mL per well of "3×ERa solution": 22 nM ERa (human estrogen receptor alpha, GST-tagged ESR1 ligand binding domain, spanning residues S282-V595, either wild-type sequence or containing the mutations: Y537S or D538G) in TR-FRET Coregulator Buffer E containing 7.5 mM dithiothreitol (DTT); and 2 mL of 3× Assay mix (750 nM Fluorescein-PGC1a peptide (Life Technologies PV4421), 12 nM Estradiol, 15 nM Anti-GST Tb-labeled antibody in TR-FRET Coregulator Buffer E (with 7.5 mM DTT). "No receptor" control wells received buffer without GST-ERa protein. Plates were centrifuged at 1800 rpm for 20 seconds in V-spin centrifuge and incubated for 2 hours at room temperature with the plates covered. Measurements were made using a Perkin Elmer EnVision Fluorescence Reader using TR-FRET setting (Top mirror: Perkin Elmer Lance/DELFIA Dual emission (PE #2100-4160); Excitation filter: Perkin Elmer UV (TFR) 340 nm (PE #2100-5010); Emission filtes: Chromrna 495 nm10 nm and 520 nm/25 nm (Chroma#PV003 filters for LanthaScreen, 25 mm diameter for EnVision) Excitation light: 100%; Delay: 100 us; Window time: 200; Number of sequential windows: 1; Time between flashes: 2000 us; Number of flashes: 100; Number of flashes (2$^{nd}$ detector): 100. Percentage inhibition values were calculated relative to no compound (DMSO only) controls and a "no ERa controls". Curve fitting and IC$_{50}$ calculations were carried out using Genedata Screener software.

Example 58

Inhibition of MCF7 Proliferation Assay

MCF7 cells were washed with PBS and plated in RPMI 1640 (Gibco 11835-030 [−phenol +glutamine]) and 10% Charcoal Stripped FBS (Gibco 12676-029), in poly-lysine coated 384 well tissue culture plates (Greiner) at 25,000 cells/ml; 40 ul/well, and incubated overnight. Compounds were prepared in serial dilution in DMSO at 500-fold the final desired concentration using a Biomek-FX and diluted 50-fold in RPMI 1640. The control compound fulvestrant and negative control DMSO were also prepared in a similar manner. 5 uL of each individual compound concentration and each control compound was transferred to the cell plate. Fulvestrant was added to control wells at a final concentration of 100 nM). DMSO was added to negative control wells (0.2% v/v). 5 uL of 1 nM Estradiol (in phenol red free RPMI 1640 (Gibco 11835-030) was added to each well of the cell plate (except no estradiol control wells). Cells were incubated for 72 hours then lysed using Cell TiterGlo reagent (Promega #G7572) 40 uL/well and the luminescence was measured on an Envision (Perkin Elmer) plate reader. Data were analyzed using Genedata Screener software, using DMSO and Fulvestrant treated samples to define 0% and 100% inhibition and EC$_{50}$ values were calculated using curve fitting using Robust method.

Example 59

Ishikawa Uterine Cell Alkaline Phosphatase Assay

Subconfuent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 μL per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added (1 mg/mL final concentration) to a solution containing 2 mM MgCl$_2$, 1 M diethanolamine, and adjusted to pH 9.0. The substrate solution is added to the cell cultures (16 μL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17β-estradiol treated cells×100.

Example 60

PEO Cell Viability Assays

PEO-1, PEO-4 and PEO-6 ovarian cancer cell lines were adjusted to a concentration of 20,000 cells per mL in RPMI containing 10% FBS. 16 microliters of the cell suspension (320 cells) was added to each well of a 384 well plate, and the cells were incubated overnight to allow the cells to adhere. The following day a 10 point, serial 1:5 dilution of each compound was added to the cells in 16 μL at a final concentration ranging from 1-0.0000005 μM. After 7 days of compound exposure, 16 μL of CellTiter-GLo (Promega, Madison Wis.) was added to the cells the relative luminescence units (RLUs) of each well was determined. CellTiter-Glo added to 32 μL of medium without cells was used to obtain a background value. The percent viability of each sample was determined as follows: (RLU sample–RLU background/RLU untreated cells–RLU background)× 100=% viability.

Example 61

PEO ER Western Analysis

Cells are plated in RPMI 5% CSS for 48 hours, then treated with compound for 4 or 24 hours. Cells are lysed in modified radioimmunoprecipitation buffer (mRIPA; 10 mM Tris, 150 mM NaCl, 1% (v/v) NP-40, 0.5% deoxycholate, 0.1% SDS, 5 mM EDTA, pH 7.4) containing Halt Protease & Phosphatase Single-Use Inhibitor Cocktail (Thermo Scientific, Cat. No. 78442). Total protein of the clarified lysates is quantitated by Lowry Assay (Biorad DC protein assay). NuPAGE® LDS Sample Buffer and Sample Reducing Agent are added to the lysates and heated to 70° C. for 10 mins. 15 ug of total cell protein is separated electrophoretically in a NuPAGE 4-12% Bis Tris Gel in MOPS SDS running buffer, then transferred to a nitrocellulose membrane in transfer buffer using an XCell II blot module. Membranes are incubated in Blocking Buffer (LI-COR, Lincoln, Nebr.) for 30 minutes at room temperature, followed by 60 minute incubations with a rabbit antibody against ER alpha (SP-1, Thermo Fisher Scientific, Cat. No. RM-9101), ER beta (Cell Signaling Technology, Cat. No. 5513), or mouse antibody against alpha tubulin (Sigma, Cat. No. T6199). Following incubation with an IRDye® Conjugated Goat Anti Mouse or Anti Rabbit IgG (LI-COR), protein bands are quantified using an Odyssey® Infrared Imaging System. Graphing of data to determine ER levels is performed using Graphpad PRISM® software. % ER levels are calculated as follows:

% ER=(fluorescence ER band of sample–bkgrd/fluorescence Tubulin band of sample–bkgrd)/(fluorescence ER band of untreated cells–bkgrd/ fluorescence Tubulin of untreated cells–bkgrd)

Example 62

Breast Cancer Model; Xenograft Assay (MCF-7)

Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 µL/animal) on the right flank 2-3 days post pellet implantation. Tumor volume (length× width$^2$/2) is monitored bi-weekly. When tumors reach an average volume of ~200 mm$^3$ animals are randomized and treatment is started. Animals are treated with Vehicle or Compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 63

Breast Cancer Model; Xenograft Assay (MCF-7 Derivative)

Female nu/nu mice (with supplemental 17-β Estradiol pellets; 0.72 mg; 60 day slow release) bearing MCF-7 tumors (mean tumor volume 200 mm$^3$) are treated with Tamoxifen (citrate) by oral gavage. Tumor volume (length× width$^2$/2) and body weight are monitored twice weekly. Following a significant anti-tumor response in which tumor volume remained static, evident tumor growth is first observed at approximately 100 days of treatment. At 120 days of treatment, tamoxifen dose is increased. Rapidly growing tumors are deemed tamoxifen resistant and selected for in vivo passage into new host animals. Tumor Fragments (~100 mm$^3$/animal) from the tamoxifen resistant tumors are subcutaneously implanted into the right flank of female nu/nu mice (with 17-β Estradiol pellets (0.72 mg; 60 day slow release)). Passaged tumors are maintained under constant Tamoxifen selection, and Tumor volume (length× width$^2$/2) is monitored weekly. When tumor volume reached ~150-250 mm$^3$, animals are randomized into treatment groups (mean tumor volume 200 mm$^3$) and tamoxifen treatment is terminated (except for a tamoxifen control arm). Animals are treated with Vehicle or Compound daily for 4 weeks. Tumor volume and body weight are monitored twice weekly for the duration of the study. At the conclusion of the treatment period; plasma and tumor samples are taken for pharmacokinetic and pharmacodynamic analyses, respectively.

Example 64

Endometrial Cancer Model; Xenograft Assay (ECC-1)

ECC-1 cells are grown in DMEM (phenol red, 4.5 g/L glucose and L-glutamine) containing 10% FBS, 1% Non-Essential Amino Acids and 100 units Penicillin/Streptomycin at 10% $CO_2$, 37° C. Cells are spun down and re-suspended in 50% DMEM (serum free) and 50% Matrigel (BD, high concentration) at $5\times10^7$ cells/mL. Time release pellets (0.72 mg 17-β Estradiol/60 days) are subcutaneously implanted into female nu/nu mice. ECC-1 cells are subcutaneously injected (100 µL/animal) on the right flank 2-3 days post pellet implantation. Tumor volume is monitored and when tumors reach a suitable size for transplant they are excised. Excised tumors are cut into small pieces (~100 mm$^3$) and serially transplanted (10 G trocar, right flank) into female nu/nu containing estradiol pellets (0.72 mg 17-β Estradiol/60 days) for 2-3 days. Tumor volume (length× width×width/2) is monitored and when palpable tumors are observed, animals are randomized and treatment is started. Animals are treated with Vehicle or Compound daily for 4 weeks or until tumor volume reaches 2000 mm$^3$ (whichever comes first). Tumor volume and body weight are monitored bi-weekly throughout the study. At the conclusion of the treatment period; plasma and tumor samples are taken for pharmacokinetic and pharmacodynamic analyses, respectively.

Example 65

Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 66

Immature Uterine Wet Weight-Agonist Mode

Female immature CD-IGS rats (21 days old upon arrival) were treated for three days. Animals were dosed daily for three days. Vehicle or test compound was administered orally by gavage. On the fourth day 24 hours after dose, plasma was collected for pharmacokinetic analysis. Immediately following plasma collection, the animals were euthanized and the uterus was removed and weighed.

Example 67

Parenteral Pharmaceutical Composition

To prepare a parenteral pharmaceutical composition suitable for administration by injection (subcutaneous, intravenous), 100 mg of a water-soluble salt of a compound of Formulas (I)-(X) is dissolved in sterile water and then mixed with 10 mL of 0.9% sterile saline. The mixture is incorporated into a dosage unit form suitable for administration by injection.

In another embodiment, the following ingredients are mixed to form an injectable formulation: 1.2 g of a compound of Formulas (I)-(X), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 68

Oral Solution

To prepare a pharmaceutical composition for oral delivery, an aqueous 20% propylene glycol solution is prepared. To this is added a sufficient amount of compound of Formulas (I)-(X), or a pharmaceutically acceptable salt thereof, to provide a 20 mg/mL solution.

Example 69

Oral Capsule

To prepare a pharmaceutical composition for oral delivery, 100-500 mg of a compound of Formulas (I)-(X), or a pharmaceutically acceptable salt thereof, is mixed with starch. The mixture is incorporated into an oral dosage unit such as a hard gelatin capsule, which is suitable for oral administration.

In another embodiment, 100-500 mg of a compound of Formulas (I)-(X), or a pharmaceutically acceptable salt thereof, is placed into Size 4 capsule, or size 1 capsule (hypromellose or hard gelatin) and the capsule is closed.

Example 70

Oral Tablet

A tablet is prepared by mixing 48% by weigh of a compound of Formulas (I)-(X), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 71

Topical Gel Composition

To prepare a pharmaceutical topical gel composition, a compound of Formulas (I)-(X), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Although the foregoing invention has been described in some detail by way of illustration and example for purposes of clarity of understanding, the descriptions and examples should not be construed as limiting the scope of the invention. The examples and embodiments described herein are for illustrative purposes only and various modifications or changes suggested to persons skilled in the art are to be included within the spirit and purview of this application and scope of the appended claims. The disclosures of all patent and scientific literature cited herein are expressly incorporated in their entirety by reference.

What is claimed:

1. A compound of Formula (VII), or a pharmaceutically acceptable salt thereof:

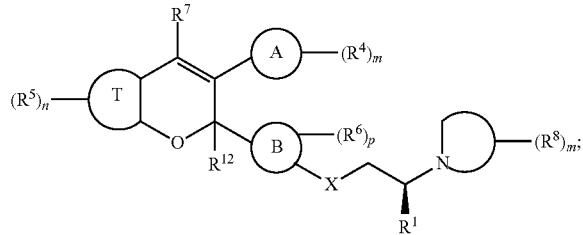

Formula (VII)

wherein:

X is —O—;

ring A is monocyclic heteroaryl or bicyclic heteroaryl;

ring B is phenyl or a monocyclic heteroaryl;

ring T is a fused phenyl, a fused monocyclic heteroaryl, or a fused bicyclic heteroaryl;

$R^1$ is H, F, $C_1$-$C_4$ alkyl, or $C_1$-$C_4$ fluoroalkyl;

each $R^4$ is independently, halogen, —CN, —OH, —$OR^9$, —$SR^9$, —S(=O)$R^{10}$, —S(=O)$_2R^{10}$, —NHS(=O)$_2R^{10}$, substituted or unsubstituted $C_1$-$C_6$ alkyl, substituted or unsubstituted $C_1$-$C_6$ fluoroalkyl, substituted or unsubstituted $C_1$-$C_6$ fluoroalkoxy, substituted or unsubstituted $C_1$-$C_6$ alkoxy, or substituted or unsubstituted $C_1$-$C_6$ heteroalkyl;

each $R^5$ is independently H, halogen, —CN, —OH, —$OR^9$, —$SR^9$, —S(=O)$R^{10}$, —S(=O)$_2R^{10}$, —NHS(=O)$_2R^{10}$, substituted or unsubstituted $C_1$-$C_6$alkyl, substituted or unsubstituted $C_1$-$C_6$ fluoroalkyl, substituted or unsubstituted $C_1$-$C_6$ fluoroalkoxy, substituted or unsubstituted $C_1$-$C_6$ alkoxy, or substituted or unsubstituted $C_1$-$C_6$ heteroalkyl;

each $R^6$ is independently H, halogen, —CN, —OH, —$OR^9$, —$SR^9$, —S(=O)$_2R^{10}$, —S(=O)$_2R^{10}$, —NHS(=O)$_2R^{10}$, substituted or unsubstituted $C_1$-$C_6$ alkyl, substituted or unsubstituted $C_1$-$C_6$ fluoroalkyl, substituted or unsubstituted $C_1$-$C_6$ fluoroalkoxy, substituted or unsubstituted $C_1$-$C_6$ alkoxy, or substituted or unsubstituted $C_1$-$C_6$ heteroalkyl;

$R^7$ is H, halogen, CN, substituted or unsubstituted $C_1$-$C_6$ alkyl, or substituted or unsubstituted $C_1$-$C_6$ fluoroalkyl;

each $R^9$ is independently H, —C(=O)$R^{10}$, —C(=O)O$R^{10}$, —C(=O)NH$R^{10}$, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_{10}$ cycloalkyl, substituted or unsubstituted $C_2$-$C_{10}$ heterocycloalkyl, substituted or unsubstituted aryl, substituted or unsubstituted heteroaryl, —$C_1$-$C_2$ alkylene-(substituted or unsubstituted $C_3$-$C_{10}$ cycloalkyl), -$C_1$-$C_2$ alkylene-(substituted or unsubstituted $C_2$-$C_{10}$ heterocycloalkyl), —$C_1$-$C_2$ alkylene-(substituted or unsubstituted aryl), or —$C_1$-$C_2$ alkylene-(substituted or unsubstituted heteroaryl); or each $R^{10}$ is independently substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_{10}$ cycloalkyl, substituted or unsubstituted $C_2$-$C_{10}$ heterocycloalkyl, substituted or unsubstituted aryl, substituted or unsubstituted heteroaryl, —$C_1$-$C_2$alkylene-(substituted or unsubstituted $C_3$-$C_{10}$ cycloalkyl), —$C_1$-$C_2$ alkylene-(substituted or unsubstituted $C_2$-$C_{10}$ heterocycloalkyl), —$C_1$-$C_2$ alkylene-(substituted or unsubstituted aryl), or —$C_1$-$C_2$ alkylene -(substituted or unsubstituted heteroaryl);

$R^{12}$ is H;
m is 0, 1, 2, 3, 4 or 5;
n is 0, 1, 2, 3 or 4;
p is 0, 1, 2, 3 or 4;

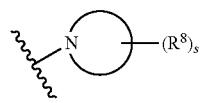

is

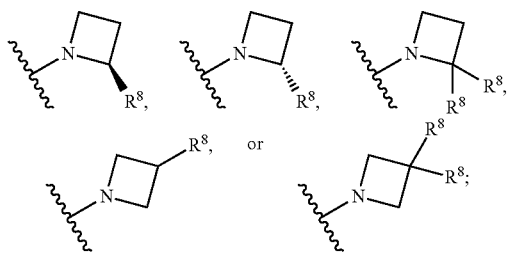

and
each $R^8$ is independently H, F, Cl, —OH, —CH$_3$, —CH$_2$CH$_3$, —CH(CH$_3$)$_2$, —CH$_2$F, —CHF$_2$, —CF$_3$, —CH$_2$CH$_2$F, —CH$_2$CHF$_2$, —CH$_2$CF$_3$, —OCF$_3$, —OCH$_2$CF$_3$, —OCH$_3$, —OCH$_2$CH$_3$, —CH$_2$OCH$_3$, —CH$_2$OCH$_2$CH$_3$, or —CH$_2$OH.

2. The compound of claim 1, or a pharmaceutically acceptable salt-thereof, wherein the compound has the structure of Formula (VIII):

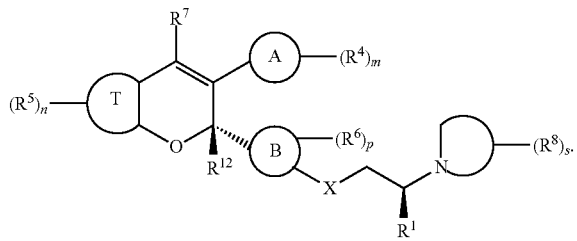

Formula (VIII)

3. The compound of claim 1, or a pharmaceutically acceptable salt-thereof, wherein:
ring A is pyrrolyl, imidazolyl, pyrazolyl, triazolyl, oxazolyl, thiazolyl, thiophenyl, furanyl, pyridinyl, pyridazinyl, pyrazinyl, pyrimidinyl, phenyl, indazolyl, benzimidazolyl, benzotriazolyl, or benzoxazolyl;

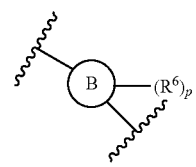

is

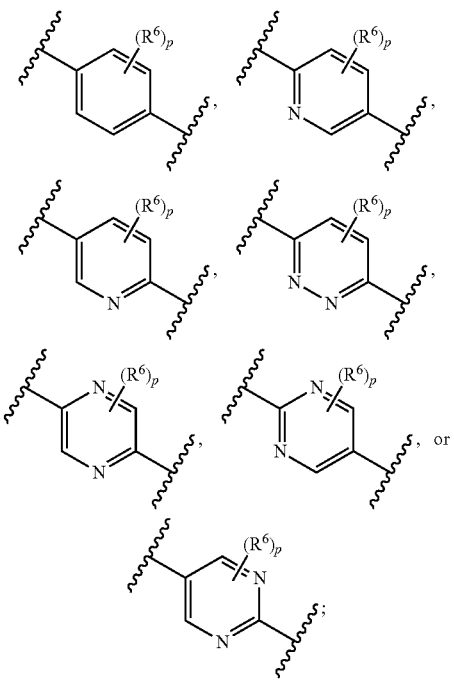

each $R^4$ is independently H, halogen, —CN, —OH, —O$R^9$, —S$R^9$, —S(=O)$_2R^{10}$, -S(=O)$_2R^{10}$, $C_1$-$C_4$ alkyl, $C_1$-$C_4$fluoroalkyl, $C_1$-$C_4$ fluoroalkoxy, $C_1$-$C_4$ alkoxy, or $C_1$-$C_4$heteroalkyl;

each $R^5$ is independently H, halogen, —OH, —O$R^9$, —S$R^9$, —S(=O)$R^{10}$, —S(=O)$_2R^{10}$, $C_1$-$C_4$ alkyl, $C_1$-$C_4$ fluoroalkyl, $C_1$-$C_4$ fluoroalkoxy, $C_1$-$C_4$ alkoxy, or $C_1$-$C_4$ heteroalkyl;

each R⁶ is independently H, halogen, —OH, $C_1$-$C_4$alkyl, $C_1$-$C_4$fluoroalkyl, $C_1$-$C_4$ fluoroalkoxy, or $C_1$-$C_4$ alkoxy;
R⁷ is $C_1$-$C_4$ alkyl or $C_1$-$C_4$ fluoroalkyl; and
p is 0, 1, or 2.
4. The compound of claim 1, or a pharmaceutically acceptable salt-thereof, wherein:
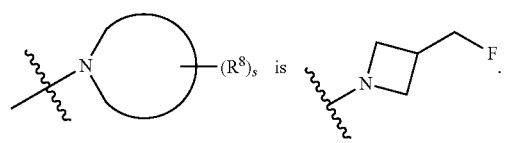
5. A compound having the formula:
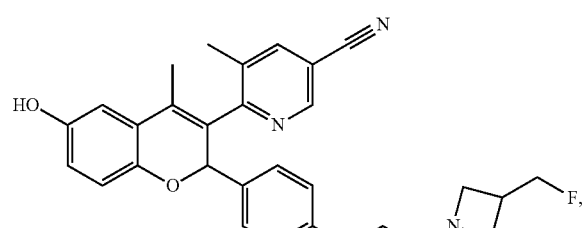
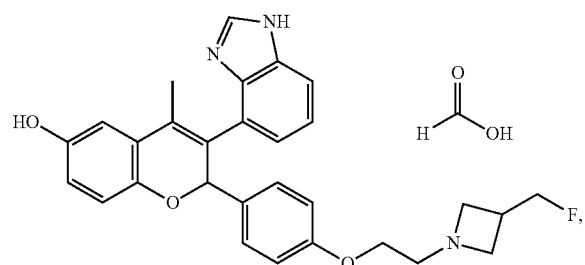
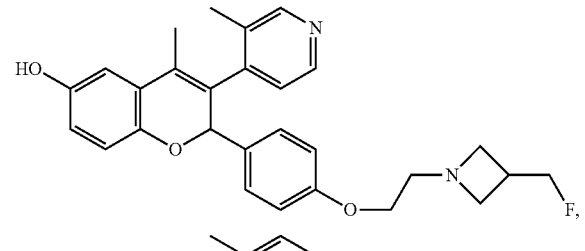
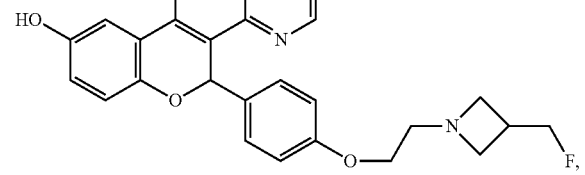
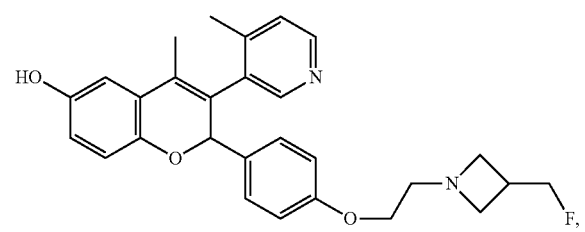
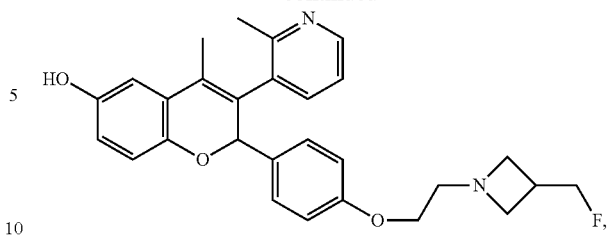
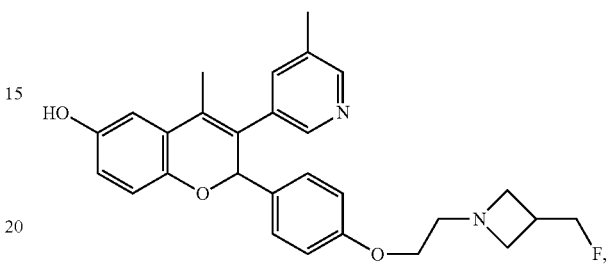
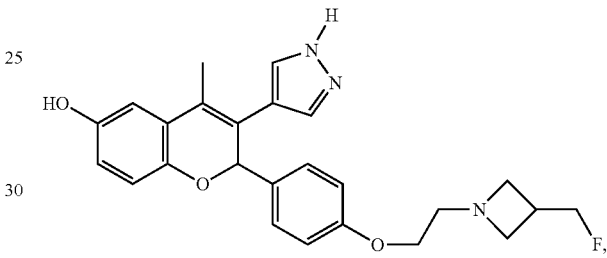
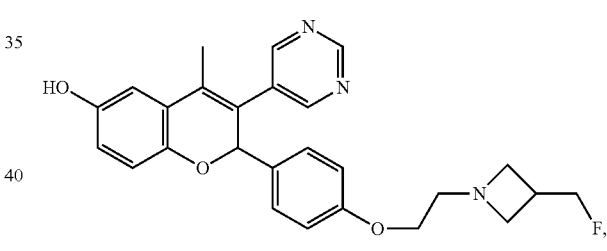
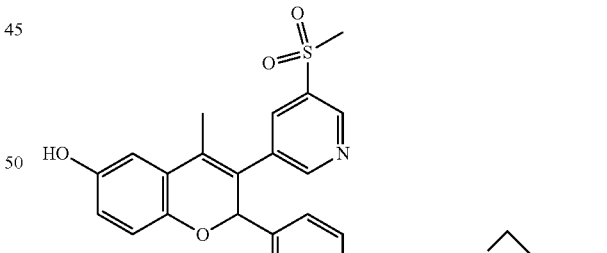
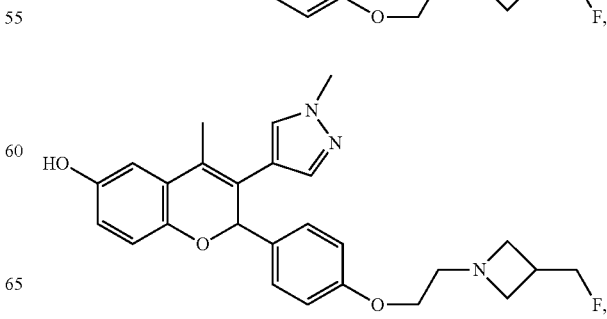

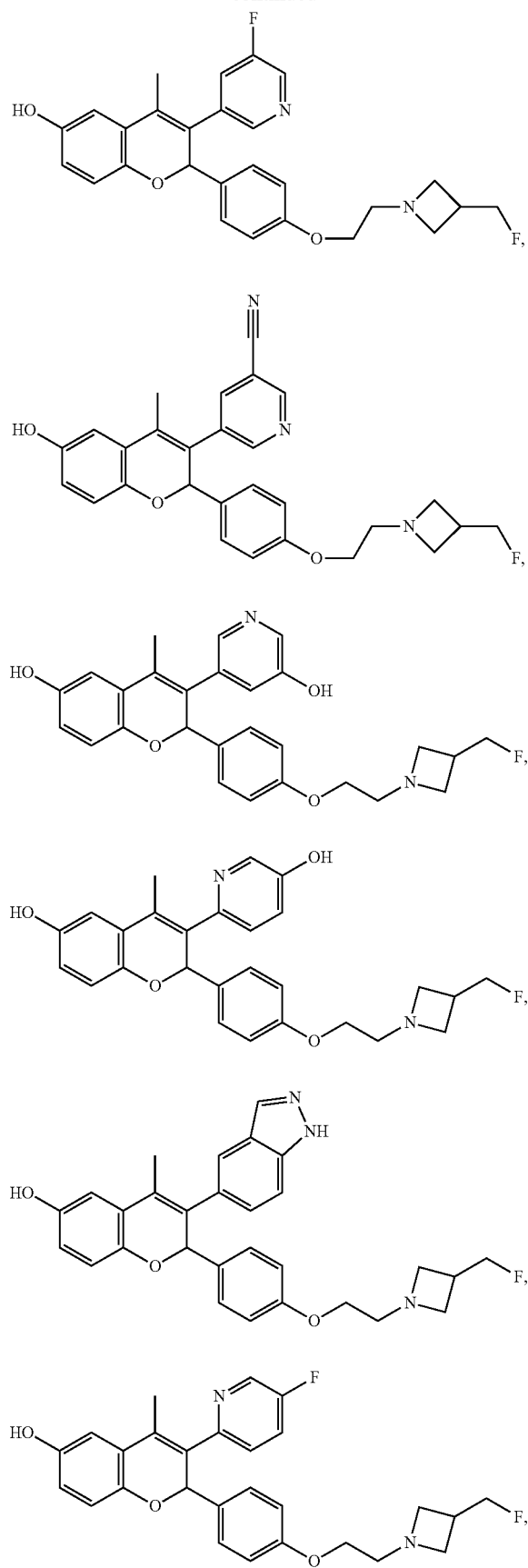
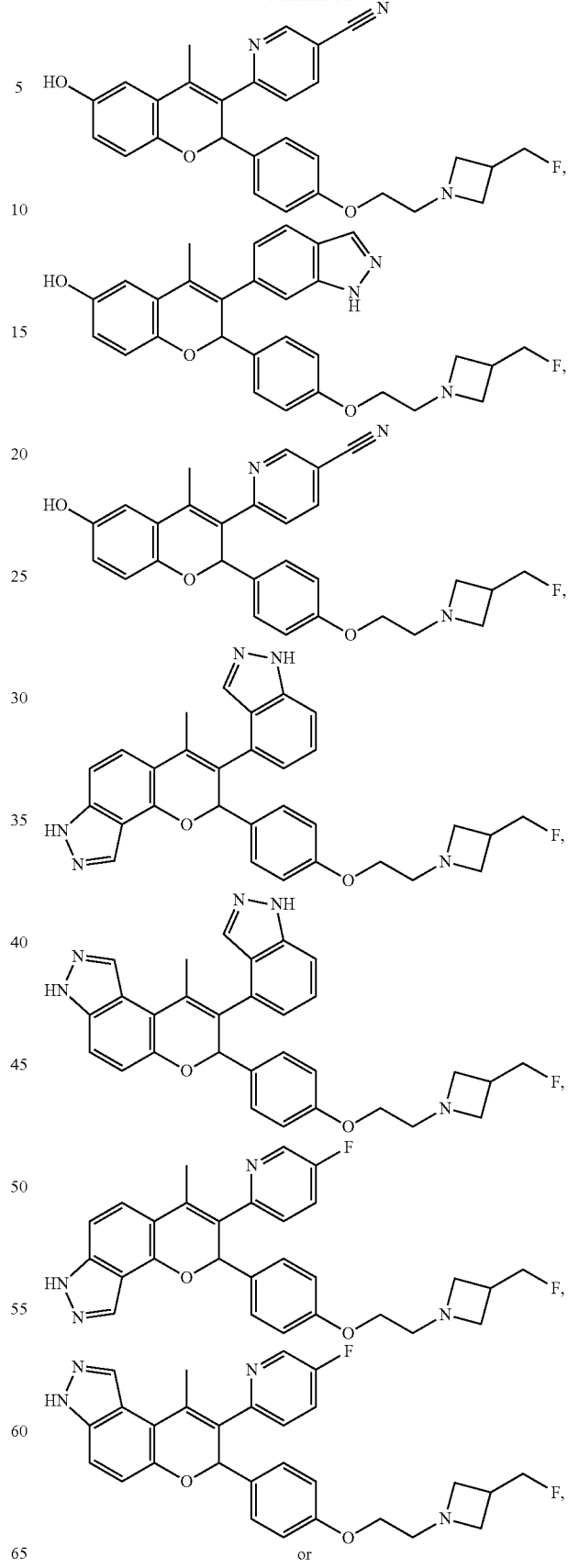

-continued

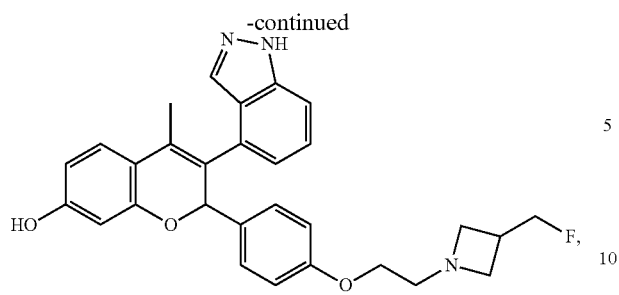

or a pharmaceutically acceptable salt thereof.

6. A pharmaceutical composition comprising a therapeutically effective amount of a compound of claim 1 or 5, or a pharmaceutically acceptable salt thereof.

7. The pharmaceutical composition of claim 6, wherein the pharmaceutical composition is formulated for intravenous injection, subcutaneous injection, oral administration, or topical administration.

8. The pharmaceutical composition of claim 6, wherein the pharmaceutical composition is a tablet, a pill, a capsule, a liquid, a suspension, a gel, a dispersion, a solution, an emulsion, an ointment, or a lotion.

9. The pharmaceutical composition of claim 6 wherein the pharmaceutical composition further comprises one or more additional therapeutically active agents.

10. The compound of claim 1, or a pharmaceutically acceptable salt thereof, wherein:
$R^1$ is H or —$CH_3$; and $R^7$ is $CH_3$.

* * * * *